United States Patent [19]
Klieman et al.

[11] Patent Number: 5,582,617
[45] Date of Patent: Dec. 10, 1996

[54] SURGICAL INSTRUMENT FOR ENDOSCOPIC AND GENERAL SURGERY

[75] Inventors: Charles H. Klieman, 79 Cypress Way, Rolling Hills Estates, Calif. 90274; Bruce M. Schena, Menlo Park; John M. Stiggelbout, Sausalito, both of Calif.

[73] Assignee: Charles H. Klieman, Rolling Hills Estates, Calif.

[21] Appl. No.: 320,941

[22] Filed: Oct. 11, 1994

Related U.S. Application Data

[63] Continuation-in-part of Ser. No. 295,352, Aug. 24, 1994, which is a continuation of Ser. No. 95,739, Jul. 21, 1993, abandoned.

[51] Int. Cl.$^6$ .............................. A61B 17/28; A61B 17/32
[52] U.S. Cl. ............... 606/170; 606/205; 606/174
[58] Field of Search ................................ 606/174, 170, 606/205, 206, 207; 128/751

[56] References Cited

U.S. PATENT DOCUMENTS

| | | |
|---|---|---|
| 4,258,716 | 3/1981 | Sutherland . |
| 4,672,964 | 6/1987 | Dee et al. . |
| 4,688,555 | 8/1987 | Wardle . |
| 4,763,669 | 8/1988 | Jaeger . |
| 4,872,456 | 10/1989 | Hasson ..................... 606/207 |
| 5,174,300 | 12/1992 | Bales et al. . |
| 5,282,826 | 2/1994 | Quadri ..................... 606/207 |
| 5,308,358 | 5/1994 | Bond et al. . |
| 5,314,445 | 5/1994 | Heidmueller née Degwitz et al. . |
| 5,318,589 | 6/1994 | Lichtman . |
| 5,330,502 | 7/1994 | Hassler et al. . |
| 5,350,355 | 9/1994 | Sklar . |
| 5,350,391 | 9/1994 | Iacovelli . |
| 5,374,277 | 12/1994 | Hassler . |
| 5,383,888 | 1/1995 | Zvenyatsky et al. . |
| 5,474,571 | 12/1995 | Lang . |

FOREIGN PATENT DOCUMENTS

| | | |
|---|---|---|
| 2681775 | 4/1993 | France ..................... 606/174 |
| 4300307A1 | 7/1994 | Germany . |
| 4307539A1 | 9/1994 | Germany . |
| 980703 | 12/1982 | U.S.S.R. ..................... 606/174 |
| PCT/WO91/02493 | 3/1991 | WIPO . |
| WO93/07816 | 4/1993 | WIPO . |
| PCT/WO94/20034 | 9/1994 | WIPO . |

*Primary Examiner*—Michael H. Thaler
*Attorney, Agent, or Firm*—Fish & Richardson P.C., P.A.

[57] ABSTRACT

A surgical instrument having a handle, barrel and working end effector tip is provided. The barrel is generally tubular, with one end being releasably connected to the handle. The end effector is movably attached to the other end of the barrel, and may be positioned and operated independently through multiple linkage members connected to a motive power source housed in or attached to the handle. The instrument is operated and controlled by a microprocessor and multidimensional controller or electrical contacts included in the handle. In the preferred embodiment, the end effector is scissor-like, but other end effectors such as graspers, clamps, dissectors or needle drivers, with appropriate operating and linkage members, may be attached to the handle.

48 Claims, 44 Drawing Sheets

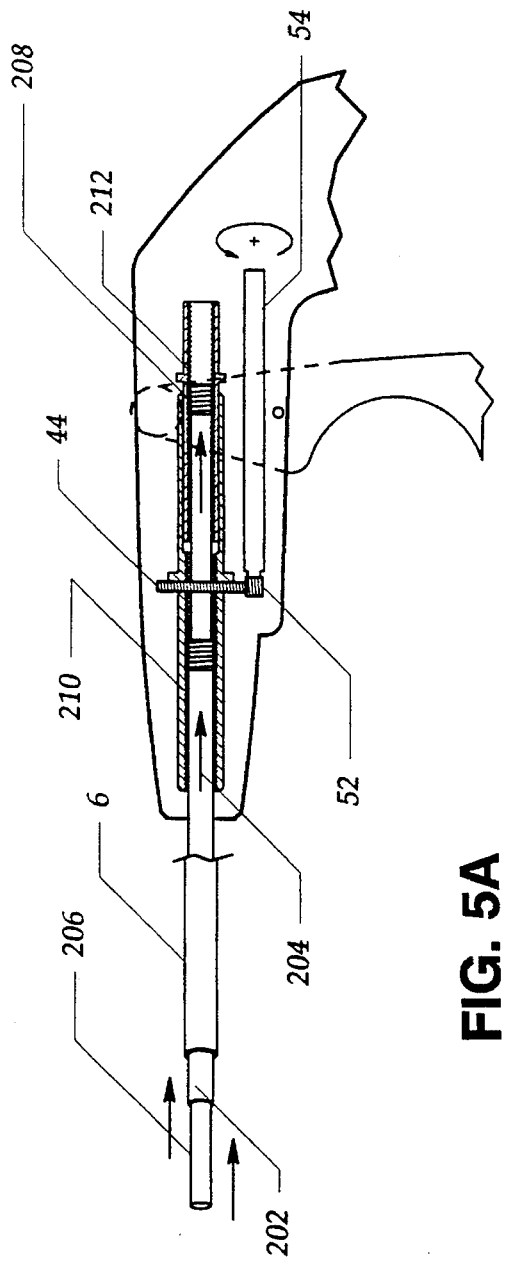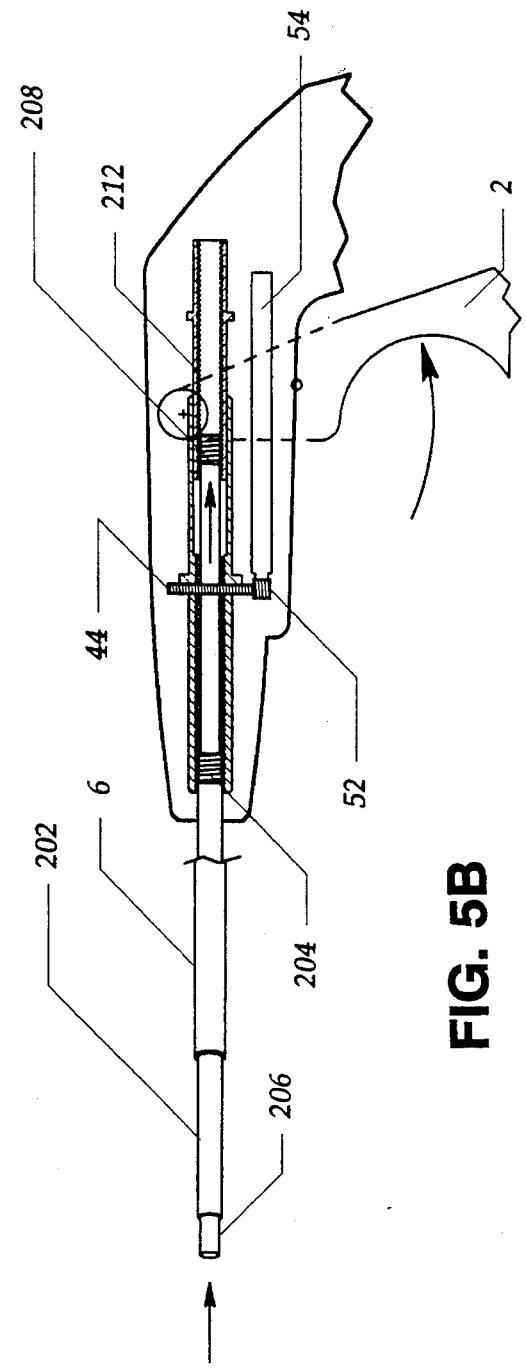
FIG. 5A
FIG. 5B

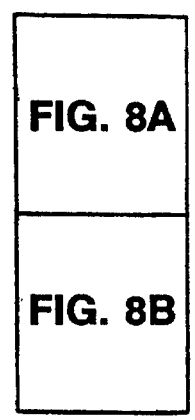
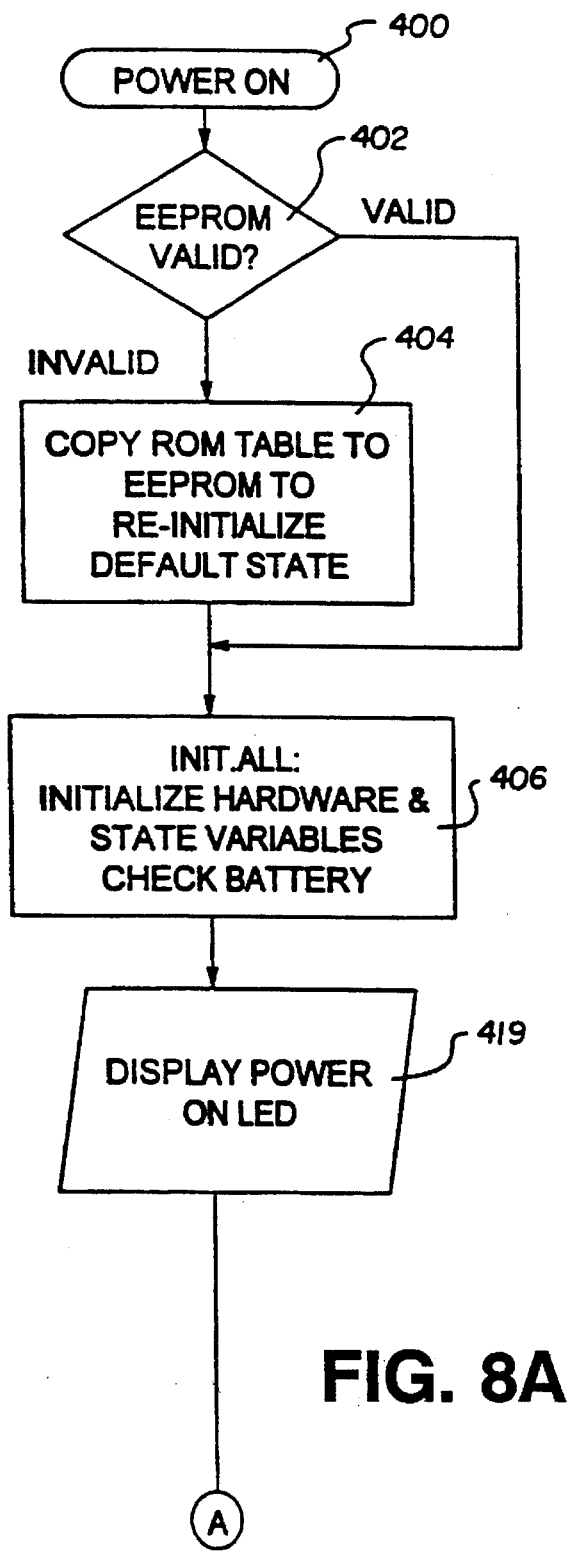
FIG. 8
FIG. 8A

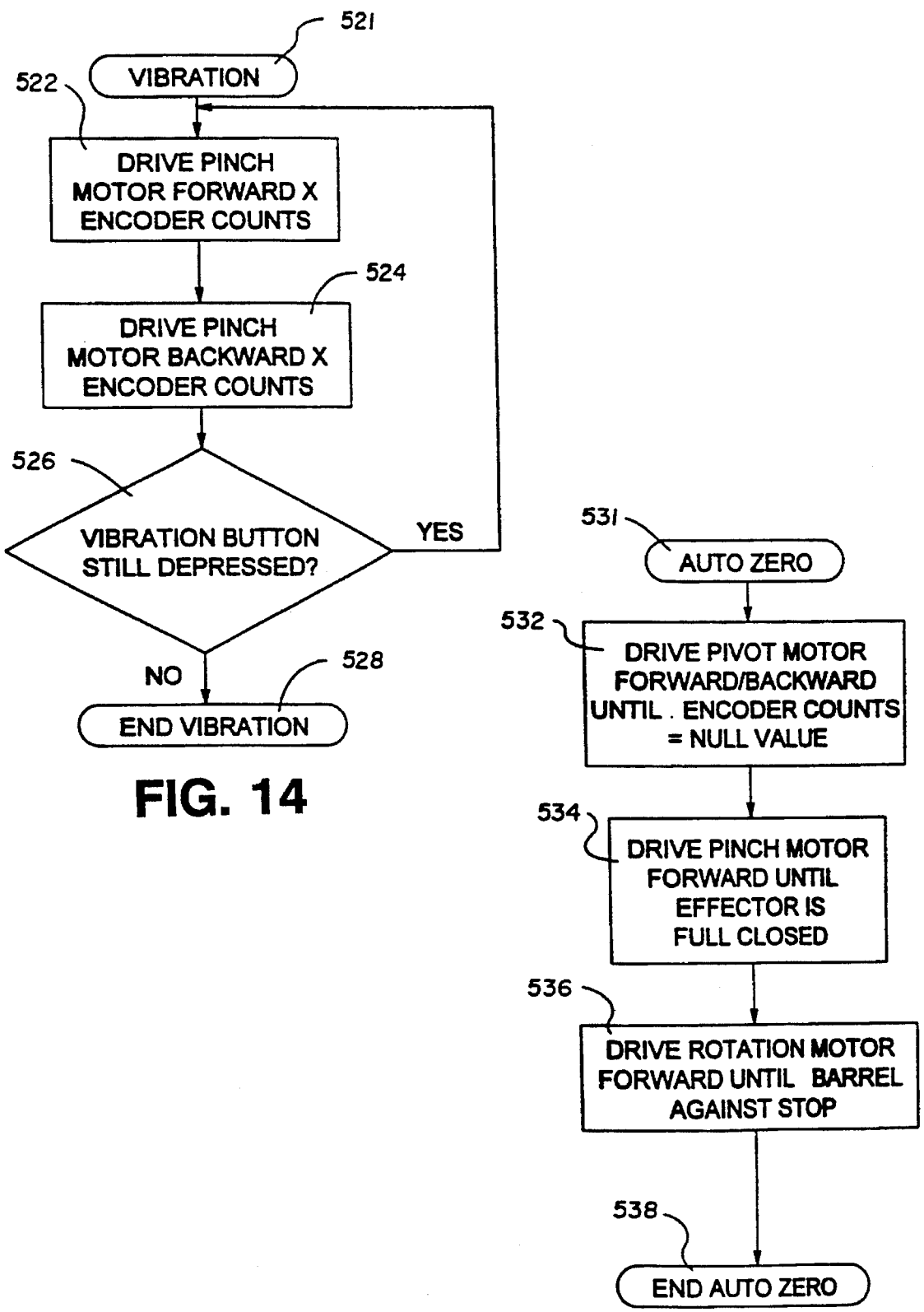

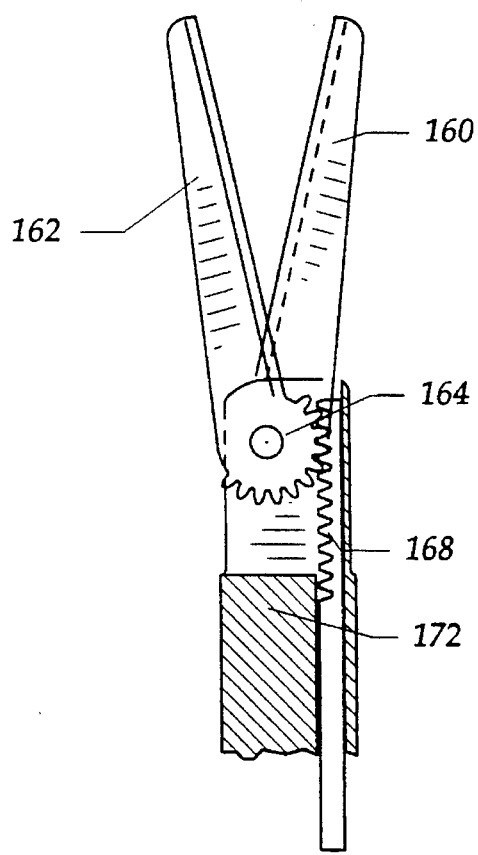
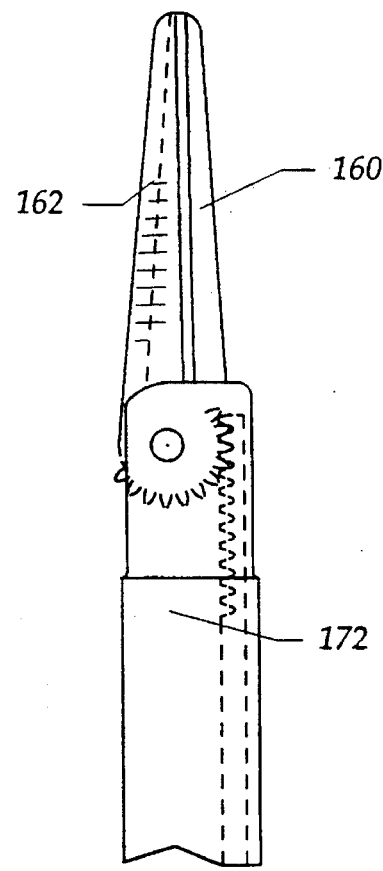
FIG. 22A  FIG. 22B
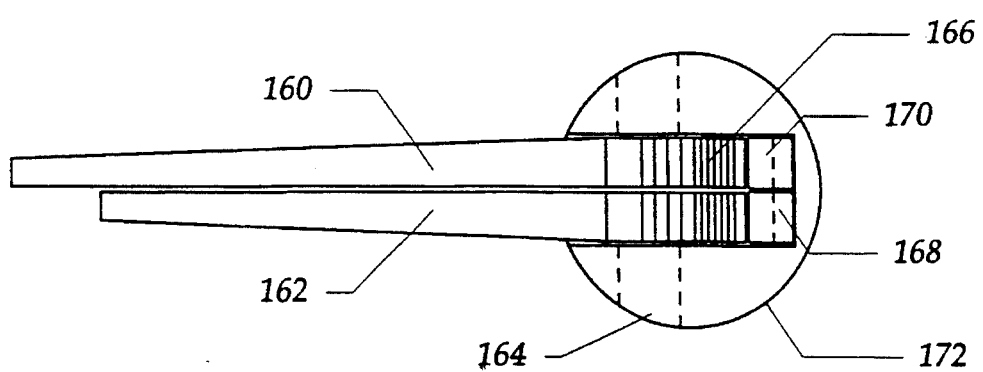
FIG. 22C

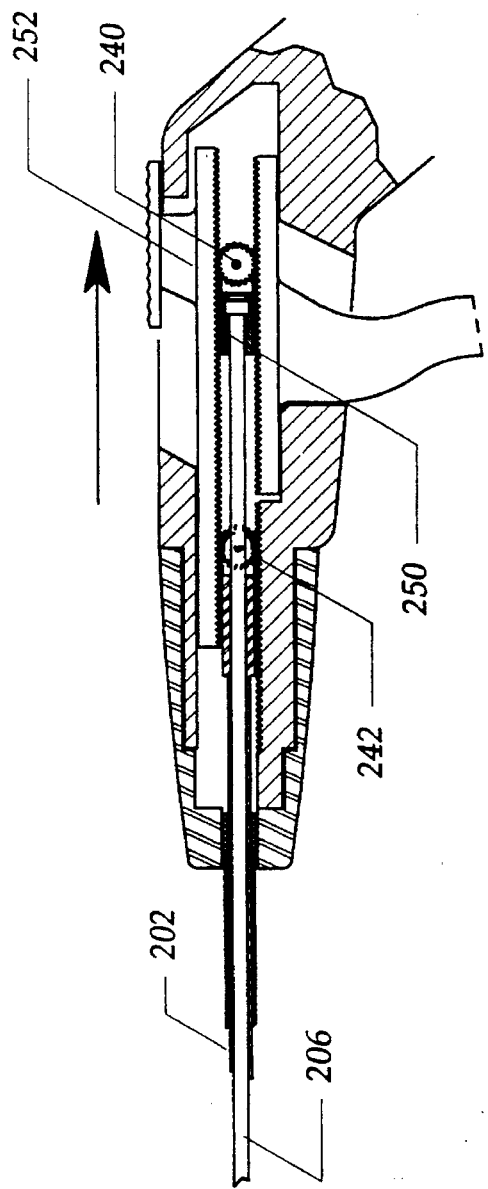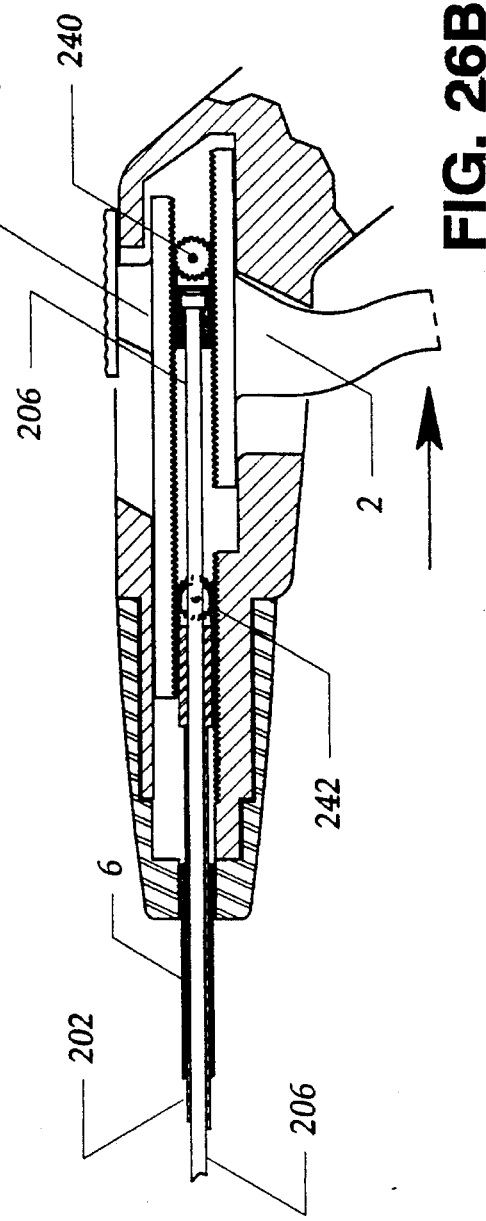

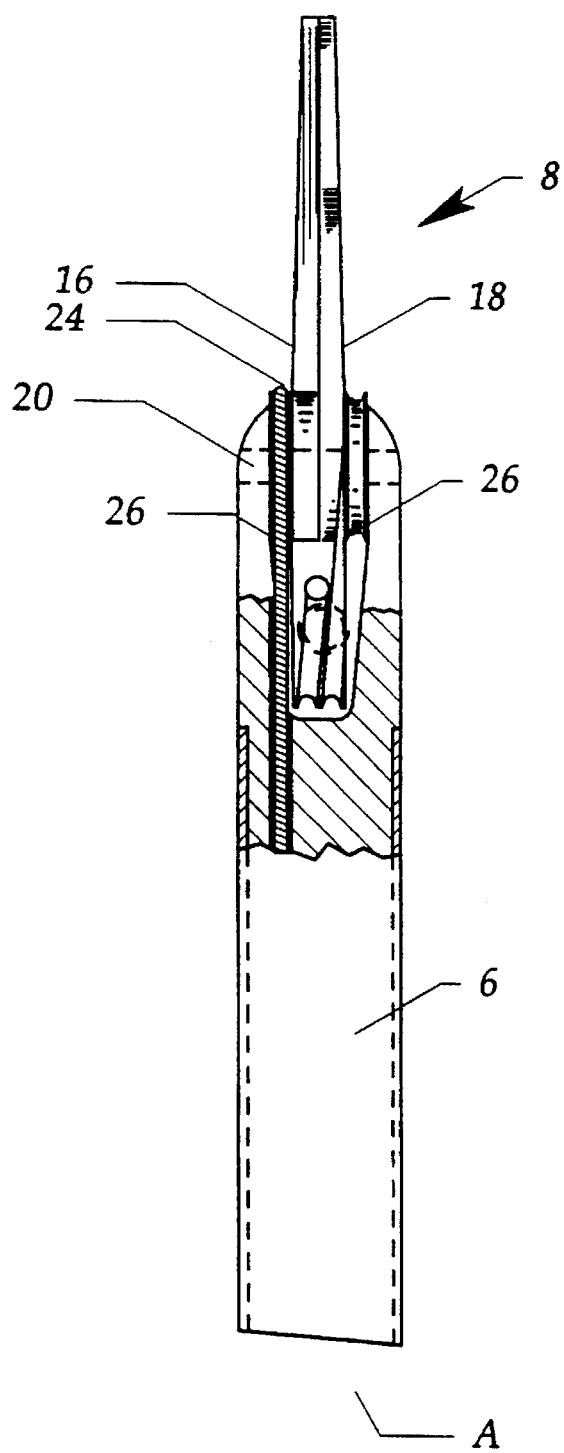
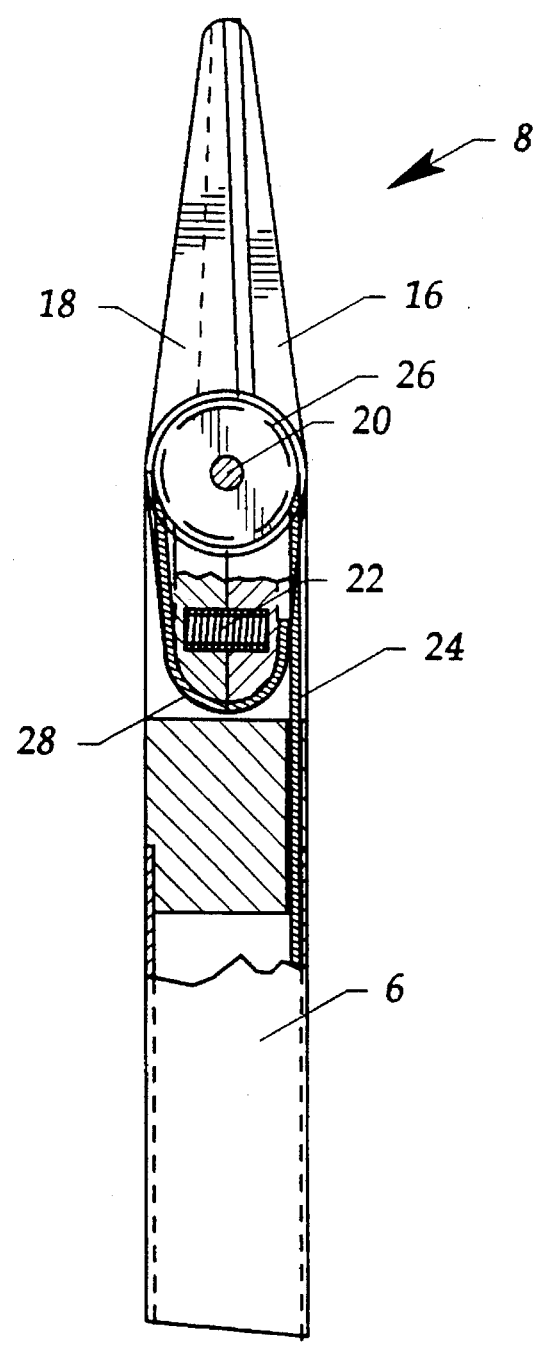
FIG. 27B  FIG. 27C

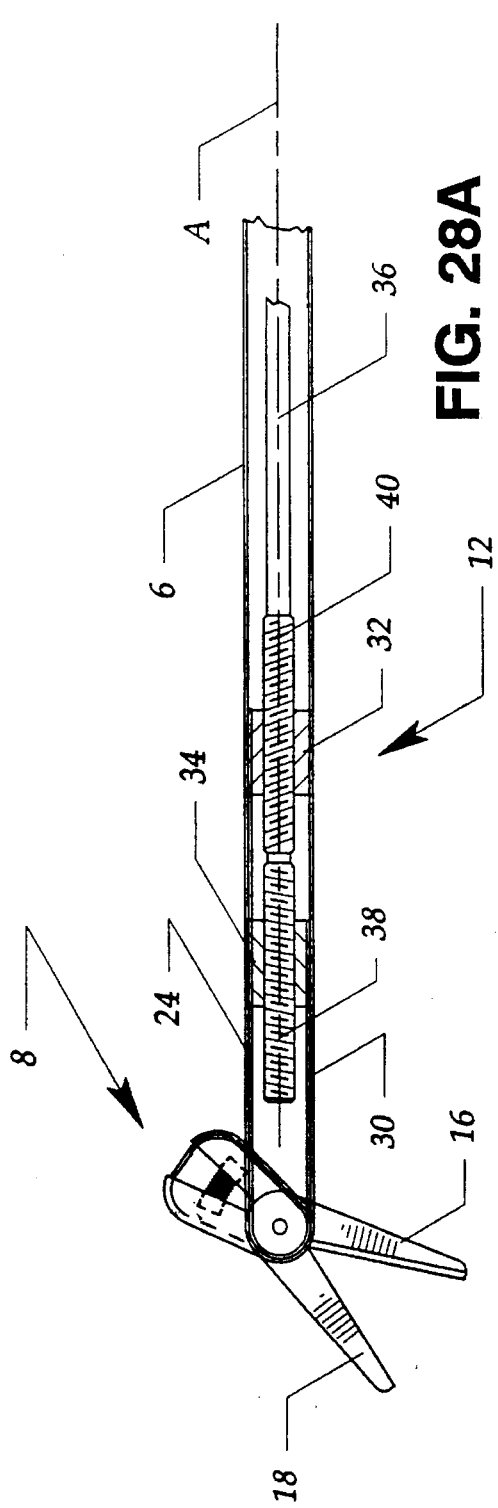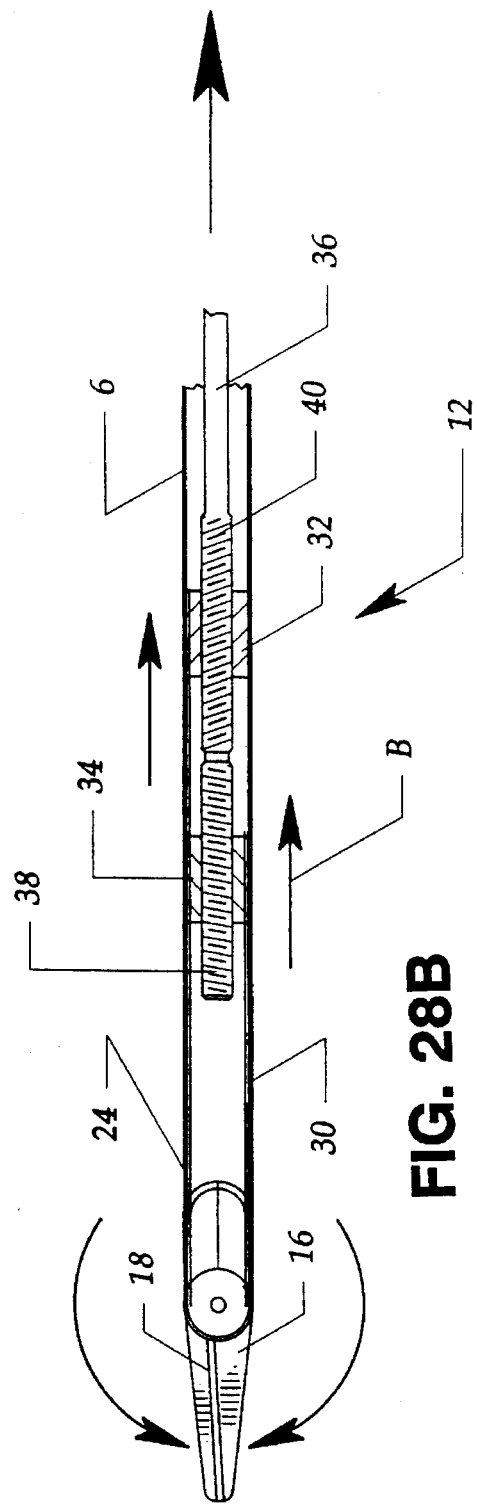

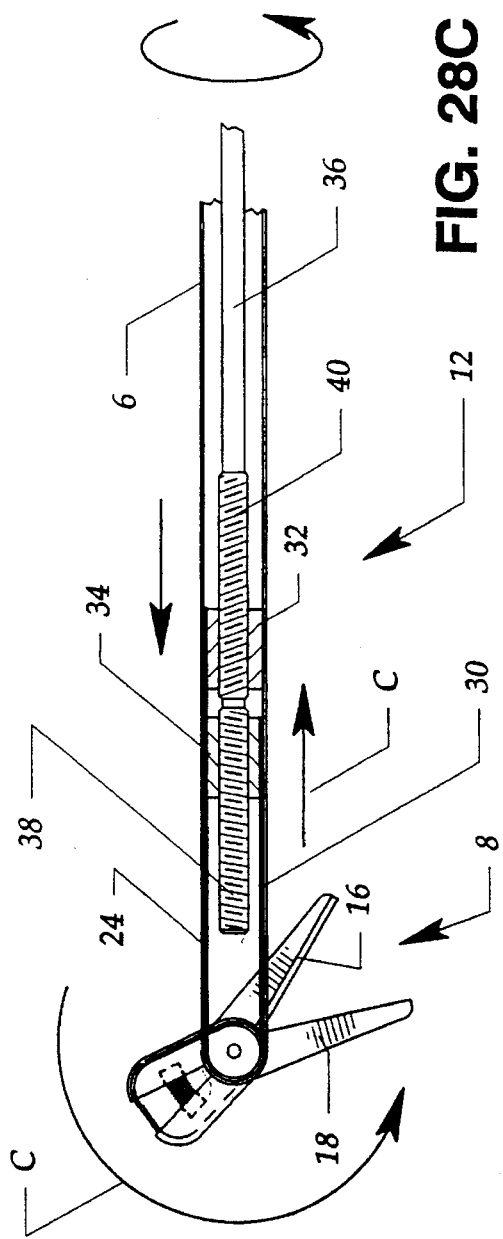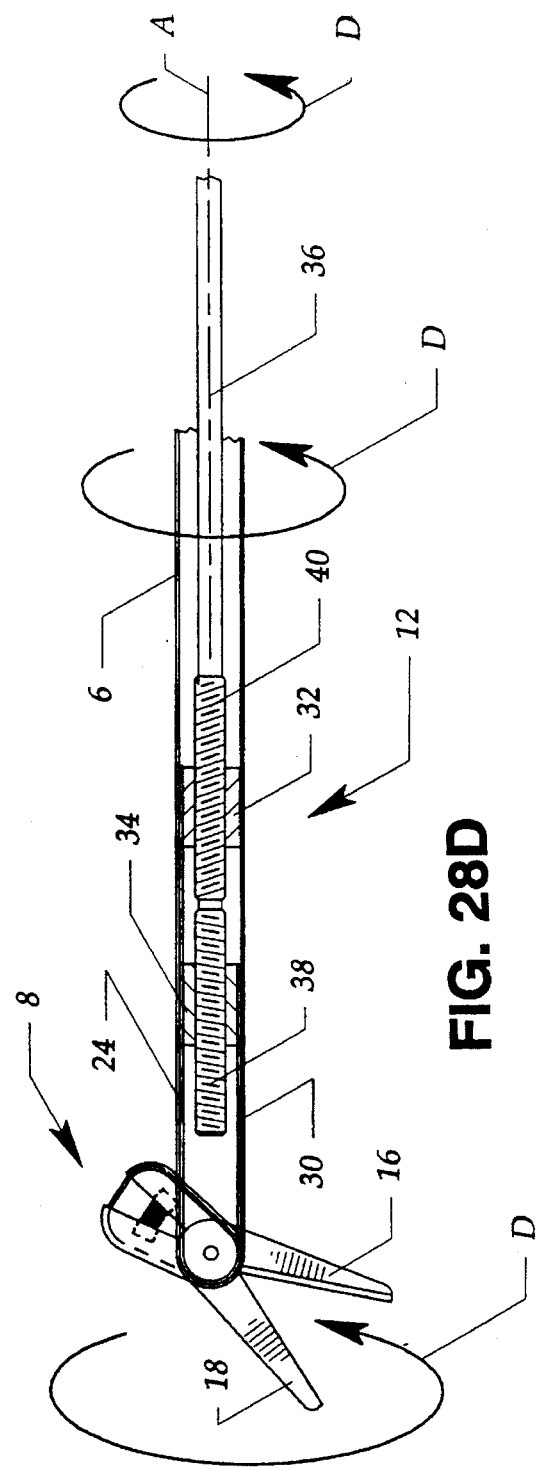

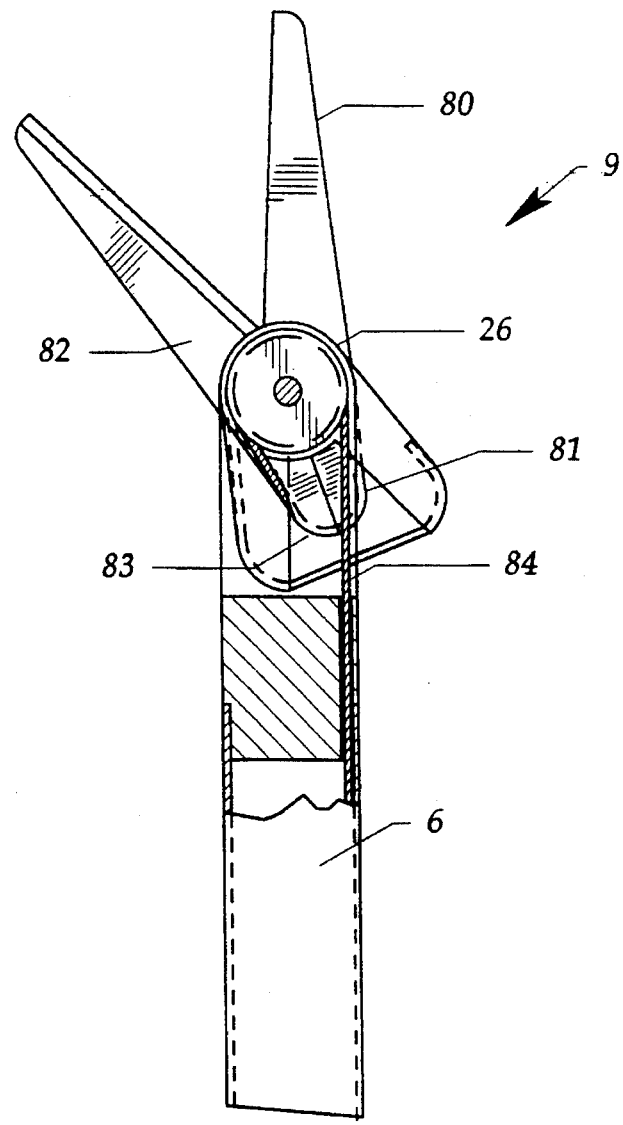
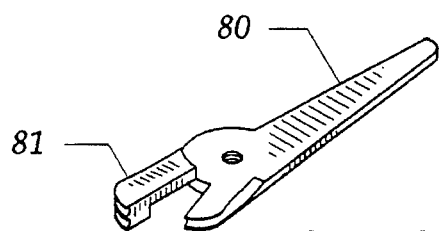
FIG. 31B
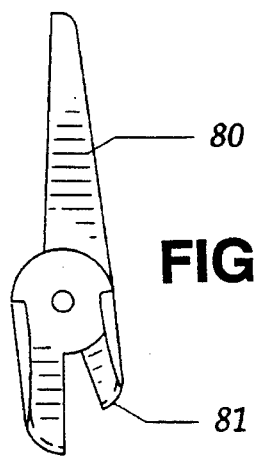
FIG. 31C
FIG. 31A

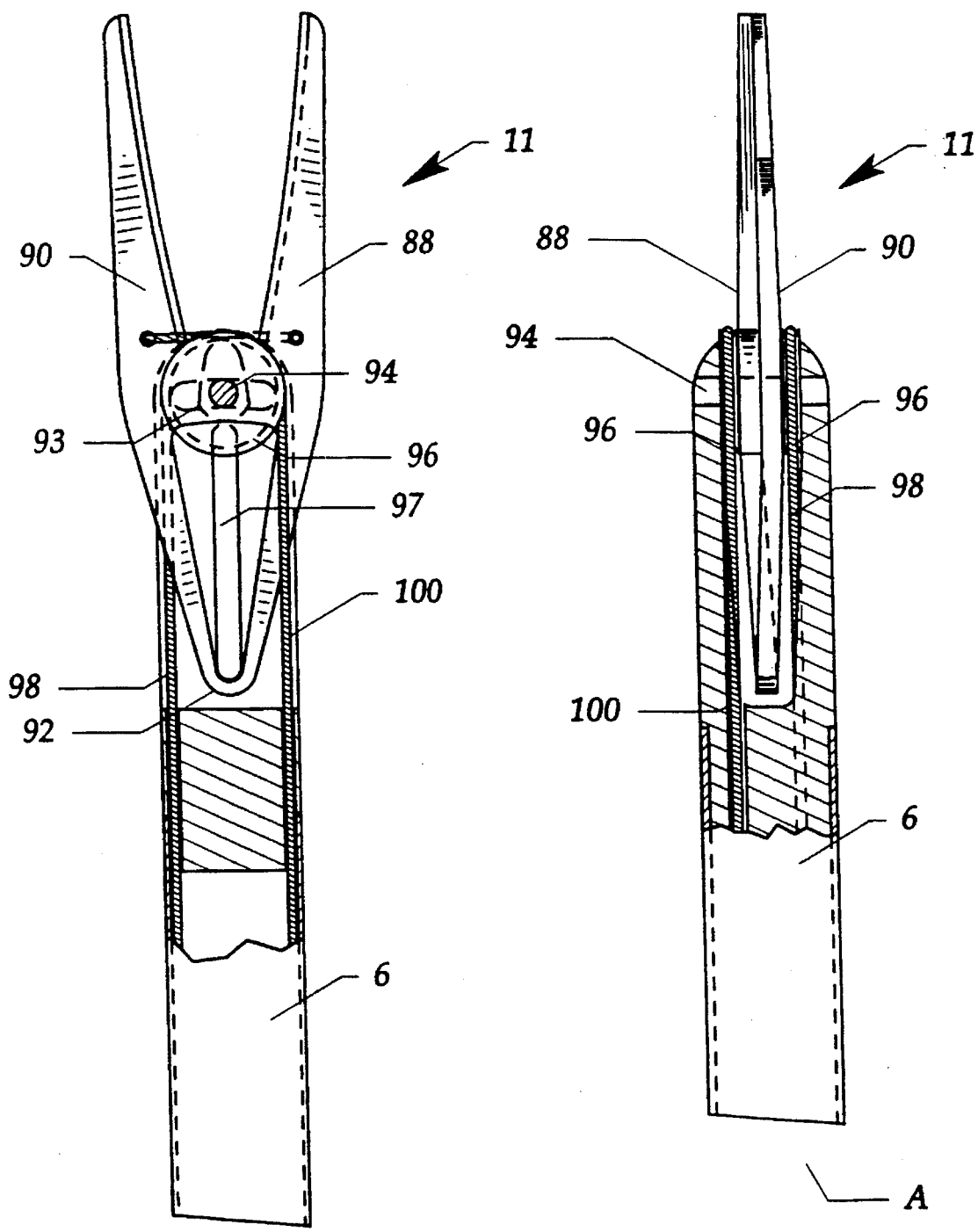
FIG. 32A  FIG. 32B

SURGICAL INSTRUMENT FOR ENDOSCOPIC AND GENERAL SURGERY

RELATED APPLICATIONS

This application is a continuation-in-part of application Ser. No. 08/295,352, filed Aug. 24, 1994 which is a continuation of Ser. No. 08/095,739 filed Jul. 21, 1993, now abandoned.

TECHNICAL FIELD

The present invention relates generally to the field of surgical instruments. In particular, it relates to a surgical instrument for use in endoscopic surgical procedures, wherein the instrument, especially the end effector carried thereby, may be positioned and operated with one hand.

BACKGROUND OF THE INVENTION

Endoscopy (e.g., laparoscopy, thoracoscopy, arthroscopy, etc.) is a form of surgery that involves visualizing the interior of the body using an illuminating optical instrument, an endoscope. The endoscope and other surgical instruments are introduced into the body through small puncture orifices.

Endoscopic procedures typically are commenced by using a device known as a trocar. The trocar comprises a cannula or trocar sleeve (a hollow sheath or sleeve with a central lumen) and a sharp obturator received in the cannula. The trocar is used to penetrate the abdominal wall or chest. The obturator is withdrawn from the cannula after the intra-abdominal end of the trocar is in the abdominal cavity, and the cannula remains in the abdominal wall throughout the surgical procedure, allowing the introduction of surgical instruments. Trocars are available in different sizes, as are cannulae, to accommodate various instruments.

Endoscopy, in the form of laparoscopy, traditionally has been used almost exclusively for gynecological surgery. However, physicians specializing in other fields have begun to recognize the diagnostic and operative value of endoscopy.

The advantages of endoscopic surgery include: procedures may be performed on an outpatient basis; surgeons are given the opportunity to view intra-abdominal viscera without performing a laparotomy, a large incision of the abdominal wall; small puncture ports or wounds are created rather than large incisions, lessening trauma; incision sites for laparotomies may be determined accurately; patient and insurer medical costs are reduced by shorter hospital stays; and postoperative patient discomfort, with recovery times measured in days as opposed to weeks, is lessened.

Thus, there is a substantial interest in and need for providing task specific surgical instruments particularly adapted to general surgical procedures now being performed endoscopically. Because endoscopy, particularly laparoscopy, is an evolving specialty within the field of general surgery, currently available instruments inadequately meet the needs of laparoscopic surgeons.

Heretofore, surgical instruments designed specifically for endoscopic procedures generally take the form of a specialized implement (hereinafter called an end effector) fixedly attached to the distal end of a rigid shaft, with an operating linkage mechanism internal or external to that shaft. A handle attached to the opposite, proximal end of the shaft usually has an associated manual mechanism for operating the end effector, and may have a second manual mechanism to rotate the shaft and end effector. Generally, in order to fit through the small diameter ports or incisions, an instrument is designed for a single, dedicated, specialized purpose. Ideally, a surgeon selects instruments according to his preferences and according to the procedure at hand. However, because of the costs involved with using additional instruments and the time associated with removing one and inserting another, a surgeon is inclined to make do with the instruments of initial use even though another instrument may be more suitable for the immediate task.

Another significant limitation in the design of current instruments is that to reposition the end effector, a surgeon must use both hands; one hand to manipulate manually a thumbwheel or knob to rotate the shaft (and end effector), and one to hold the instrument. This means that a second instrument in use has to be released, or the assisting physician or nurse has to provide help.

U.S. Pat. Nos. 4,986,825 (to Bays et al.) and 5,133,736 (to Bales, Jr. et al.) disclose surgical instruments including end effectors, e.g., scissors, dissectors, cutting jaws, etc., attached to tubular members. However, neither patent discloses or teaches how to conveniently reposition an end effector relative to the rest of an instrument while the instrument is in use.

An even greater limitation, and problem, stems from the fact that end effectors are fixedly attached to the distal end of the instrument shaft which passes through the endoscopic port. Because of this limitation in instrument design, correct placement of the port is crucial for direct access to the subject tissue or internal structure. Frequently, due to the fixed position of the end effector relative to the instrument shaft, additional laparoscopic pods or incisions must be created to allow a suitable instrument angle and access to the tissue of interest.

SUMMARY OF THE INVENTION

Accordingly, it is an object of the present invention to provide a surgical instrument which enhances surgeons' capability and dexterity, yet requires a minimum number of endoscopic ports.

Broadly, the surgical instrument of the present invention comprises a handle grip, barrel and a working end effector tip. The handle provides for holding the instrument, and is the source of or conduit for motive power for operating and controlling the end effector. The barrel is generally tubular, with one end being releasably and rotationally connected to the handle. The end effector is pivotally attached to the other end of the barrel, and the instrument includes linkage means for operably linking the end effector and motive power. Pivoting of the end effector pieces can be accomplished irrespective of the state of closure of the end effector pieces, thereby allowing independence between the pivoting, rotation and pinching movements.

In one embodiment of the present invention, the end effector may be scissor-like, including two blades pivotally attached to the distal end of the tubular barrel. The end effector blades cross over one another at a pivot point, and the opposite portions of each piece are configured as levers, extending in the proximal direction. The external sheath of a control cable, capable of acting in both tension and compression, is attached to the proximal end of one blade. The center core of the control cable, which is slidable within the external sheath, is attached to the opposite blade and is also capable of acting via both tension and compression.

The other end of the control cable, including both the sheath and core, leads inside the tubular barrel and is suitably coupled to a pair of elongated linkages which extend back into the handle. Pushing the sheath and core together in the distal direction, pushes a loop of sheath and core toward the end effector causing pivoting of both pieces of the end effector relative to the tube. Pushing and pulling the core relative to the sheath causes opening and closing of one end effector piece relative to the other. Pulling the cable (i.e., sheath and core together) causes straightening of the end effector and pulling the core causes "snipping" action of the end effector pieces. Axial rotation (i.e., rotational movement about the longitudinal axis of the barrel) is achieved by rotating the tubular barrel, including the linkages and the control cable, relative to the handle Coordinated movement of the core and sheath is via two long linkage rods which extend back into the handle. The linkage rods are coaxially configured within the barrel. The two rods are constrained from rotating within the tubular barrel, but can move lengthwise inside the barrel. Each control rod has a threaded portion on its proximal end. When attached to the handle, each threaded portion mates to its own elongated nut. The two nuts inside the handle rotate together, however one of them is restrained axially in position, while the second is attached to a trigger-like operator and can move proximally. Thus, when the trigger is moved, the center core moves relative to the external sheath and the end effector closes. The end effector pivots when the two nuts are driven as a pair and both linkages screw forward inside their respective nuts. The assembly comprising the end effector, barrel and linkages is detachable by disconnecting the tubular barrel and turning the pair of nuts, thereby unthreading the two linkage screw portions. Rotation of the nuts, and the resulting pivoting of the end effector pieces, may be done manually, or with small gearmotors.

The barrel and linkages can be removably attached to the handle by way of screw threads, a bayonet fitting, ball and detent or other mechanical restraint. Movement of the two linkages and resultant closure of the pieces of the end effector relative to each other is accomplished either manually or automatically. In the manual embodiment, a set of levers and linkages, is connected to a trigger-like arm attached to the pistol grip handle and is actuated by squeezing the hand closed. Manual closure offers direct tactile feedback to the user.

In the entirely electrically driven or powered embodiment, movement of the linkages is achieved with the aid of a geared motor or other source of motive power. The motor may be internal or external to the handle of the device, and an appropriately located power on/off switch, or switches, are associated with the handle.

In another embodiment of the present invention, the end effector may, as above, be scissor-like, having two blades pivotally connected to the distal end of the tubular barrel. One jaw end of each of the blades of the scissor end effector is sharpened to allow shearing between the two blades as they pivot against one another. The blades cross over one another at a pivot point, and the opposite portions of each blade are configured as levers extending a distance (depending on the leverage required) in the proximal direction. Between these levers is a spring biasing the levers apart, thereby opening the cutting jaws. On the outside edges of these levers are grooves which extend around a radius on the proximal end of the levers. The grooves are polished and wide enough to accommodate a high modulus tensile cord which is free to slide back and forth therein.

In this embodiment of the instrument, there are two tensile cords, each of which is attached to one blade and crosses around the proximal end of the opposite blade in its own groove. Each cord runs in the opposite direction around its own pulley on the opposite sides of the two blades. The free ends of the two cords lead inside the tubular barrel and are suitably coupled to an operating drive mechanism associated with the handle. These cords are kept in positive tension by the action of the spring between the lever end of the blades. Pulling one cord while releasing the other causes coordinated pivoting of the two blades. Pulling the two cords simultaneously causes coordinated closing of the blades. Rotating the tubular barrel causes axial rotation of the blades together with the pulleys and cords.

Coordinated movement of the two cords is achieved by the use of a threaded shaft mounted within the tubular barrel. The distal end of the internal shaft is threaded with a right-hand thread, followed by a left-hand thread. Two nuts (one threaded in right-hand orientation and the other in left-hand orientation) which are constrained from rotating, but can slide lengthwise inside the tube, are screwed onto the shaft. One of the above mentioned cords is attached to the first (distal end) nut while the second passes through a hole in the first nut and attaches to the second nut (proximal end). The threaded shaft, which can both rotate and slide axially inside the tubular barrel, is attached to a spline within the pistol grip handle. A cylindrical collar is also located within the handle and is attached to the shaft to allow engagement by a trigger mechanism to pull the shaft, together with the nuts and cords, in the proximal direction, thereby closing the scissor blades. Rotation of the shaft, by way of gears engaging the spline, allows coordinated movement of the nuts, and thereby the cords, pivoting the scissor blades in either direction.

A feature of the invention is interchangeability of end effector tips. In one embodiment, the tubular barrel and shaft(s) are splined to allow engagement with gearing means within the handle. The retraction linkages or levers (which close the two pieces of two-piece end effectors) are capable of being disconnected from the collar attached to the threaded shaft inside the tubular barrel. Replacement of the tip and barrel is accomplished by pressing a button or otherwise releasing a detent mechanism on the handle, releasing one tip so that another tip of the same or a different type may be inserted.

Another modified form of the present invention includes a pair of rack and pinion mechanisms actuating the end effector. In this invention, a gear pinion is machined into the proximal end of each of the two pieces of an end effector which are pivotally mounted in a fork on the distal end of the tubular barrel. A pair of linear racks are slidably mounted within the fork, each of which engages its respective pinion. Because each rack/pinion mating pair is independent, moving one rack in the distal direction causes pivoting of that end effector piece relative to its neighbor while pulling it in the proximal direction causes pivoting of that end effector piece in the straight direction. Pushing both racks in the distal direction causes pivoting of the end effector (i.e., both pieces thereof) and pulling both racks together causes straightening of the end effector. Elongated linkages are attached to the two racks which in turn connect to the handle. Attachment to the handle is through a pair of threaded sections and elongated nuts as described above or may be done with other connections such a bayonet fittings.

Yet another embodiment of the present invention utilizes a pair of long, sliding linkages, each of which directly engages one of the two pieces of the end effector. As with the first embodiment, the pieces (e.g., blades) cross over one another at a pivot point, and extend in the proximal direction, the opposite portions of each piece are configured as levers with elongated diagonal slots. The distal end of each linkage has an integral clevis pin which engages in the slot of its respective end effector piece. The two linkage/piece pairs work identically. Pushing one linkage in the distal direction causes the pin to slide up its slot toward the pivot, causing rotation of the piece. Pushing the linkage further in the distal direction causes continued rotation as the pin now progresses down the slot away from the pivot. In this way, pushing both linkages in the distal direction causes pivoting while pushing one and pulling the other causes scissoring.

One object of the present invention is to provide an improved surgical device having an articulated end effector or instrument head enabling the surgeon to reach areas difficult to access during a general endoscopic procedure, particularly a laparoscopic or thoracoscopic procedure, quickly and conveniently without having to move or reposition the instrument as a whole.

Still another object of the present invention is to provide an instrument adapted to accept various working end effector tips, and to provide means, incorporating elongated, tension and/or compression control and linkage members, for positionally rotating, pivoting and operating the selected end effector. Generally, the different interchangeable end effector tips include those providing all cutting and pinching or grasping actions, tips providing other movements at the distal end of the instrument, and single-piece, probe-like tips.

Yet another object of the present invention is to provide an endoscopic instrument designed to pass through trocar sleeves or endoscopic ports of various sizes, including 5 mm trocar sleeves, thereby permitting its use in minimally invasive procedures.

The instrument of the present invention advantageously provides flexibility by including a family of instruments, through the use of a common handle and actuating drive mechanism, and different, replaceable end effector tips, each connectable quickly and conveniently to the drive mechanism according to need. This inter-changeability gives the user the ability to change from one functional device to another quickly and easily while continuing to use a common handle with its associated motors, gears and controls. It also permits parts of the device to be disposable while making the most expensive parts reusable. A major advantage is that the working end effector portion of the device which penetrates the patient's body cavity will be new, sharp, and guaranteed sterile, while the rest of the device can be cleaned, sterilized, and reused. Of course, if justified by cost factors, the entire instrument may be disposable.

Still another object of the present invention is to provide an endoscopic instrument with an integrated microprocessor. An advantage of incorporating a microprocessor into the instrument of the present invention is that the logic can maintain accurate and repeatable positional control of drive motors or other motive, operational mechanisms.

The present invention has several additional important advantages over existing endoscopic surgical instruments beyond the capability to incorporate various end effector tips and articulate the selected end effector. Incorporation of electronically controlled motors and clutches gives additional flexibility to the user interface a surgeon uses to move the device in the desired directions. This interface may take the form of small slide switches, joysticks, knobs or buttons and electronic logic integrated into the handle or a remote interface controlled by a computer or other external device.

The above and other features, objects and advantages of the present invention will become more fully apparent and understood upon consideration of the following detailed description, in conjunction with the accompanying drawings and claims. It should be understood that the descriptions and drawings are for purposes of description and illustration only and are not intended as a definition of the limits of the invention.

BRIEF DESCRIPTION OF THE DRAWINGS

FIG. 5A is similar to that of FIG. 4 and depicts the pivoting movement of the end effector.

FIG. 5B is a view similar to that of FIG. 4 and depicts the movement of the barrel and shaft resulting in the pinching of closing of the end effector.

FIG. 8–17 are flow diagrams depicting the operating of the microprocessor controlled embodiment of the present invention, FIG. 8 (including FIGS. 8A and 8B) depicting the overall main operation and FIGS. 9–17 depicting subroutines.

FIG. 22A is similar to that of FIG. 21, but with the jaws aligned longitudinally with the barrel and open.

FIG. 22B is a view similar to that of FIG. 22A, but with the jaws closed.

FIG. 22C is an end elevational view of the end effector of FIGS. 21, 22A and 22B, with the jaws pivoted 45°.

FIG. 26A is similar to FIG. 25 depicting movement of the shaft, resulting in pivoting of the end effector.

FIG. 26B depicts movement of the trigger resulting in closing of the end effector.

FIG. 27B is a view similar to that of FIG. 27A and depicts the side view of the end effector.

FIG. 27C is a view similar to that of FIG. 27 and depicts the end effector in the closed position.

FIG. 28A is an elevational view of the shaft, barrel, nuts and end effector similar to FIG. 27.

FIG. 28B is a view similar to that of FIG. 28A depicting closing the blades of an end effector by moving the shaft.

FIG. 28C is a view similar to that of FIG. 28A depicting the pivoting of the end effector by rotation of the shaft.

FIG. 28D is a view similar to that of FIG. 28A, depicting the rotation of the end effector and barrel.

FIG. 31A is an elevational view of the distal end of an alternate form of the end effector of the present invention with parts broken away for clarity.

FIG. 31B is a perspective view of one jaw.

FIG. 31C is an elevational view of the jaw also depicted in FIG. 31 B.

FIG. 32A is an elevational view of the end effector of another form of the invention, partially in section and with parts for clarity.

FIG. 32B is an elevational side view of the distal end of the form of the invention shown in FIG. 32A, partially in section and with parts for clarity.

DETAILED DESCRIPTION OF THE PREFERRED EMBODIMENT

Figure 1:
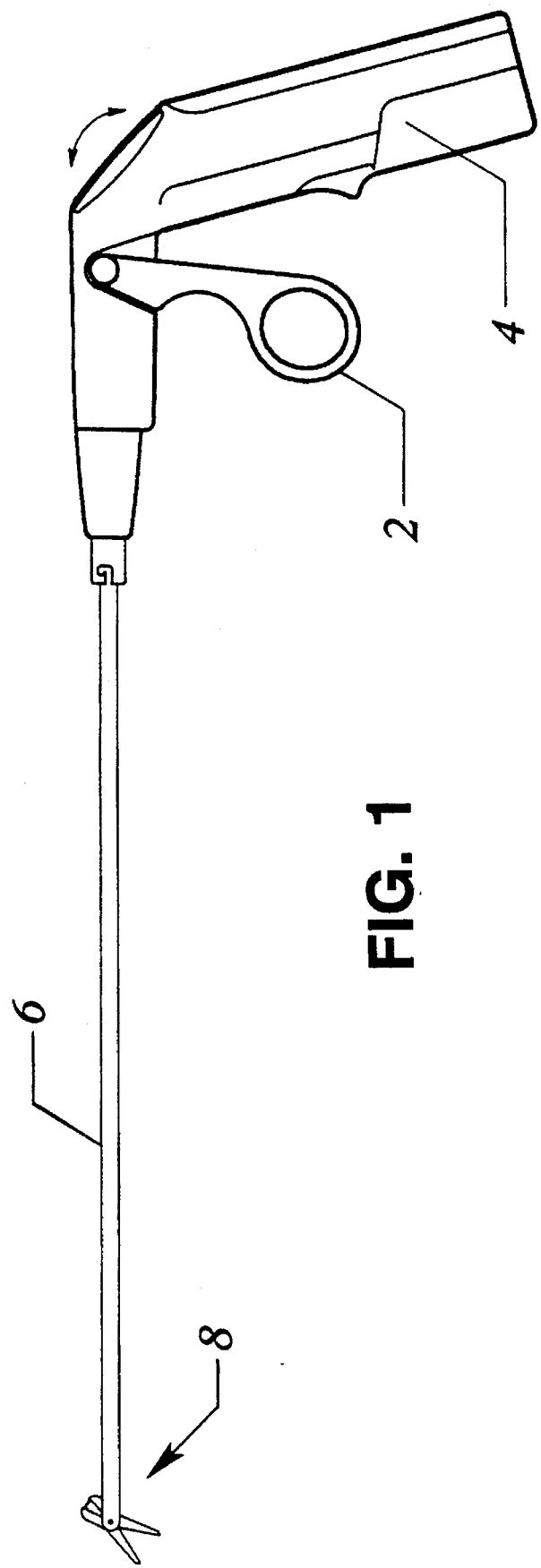
FIG. 1 is an elevational view of the present invention.

Referring to FIG. 1, the surgical instrument of the present invention includes a handle 4, an operating trigger 2, a tubular barrel 6 and end effector 8. As set forth in more detail herein below, the handle 4 houses an actuating means, including the drive and control mechanisms 10, motor(s) and associated gearing, batteries, control electronics, actuator switches and necessary wiring.

With regard to means for fastening, mounting, attaching or connecting the components of the present invention to form the surgical instrument as a whole, unless specifically described as otherwise, such means are intended to encompass conventional fasteners such as machine screws, rivets, nuts and bolts, toggles, pins, or the like. Other fastening or attachment means appropriate for connecting components include adhesives, welding and soldering, the latter particularly with regard to the electrical system.

All components of the electrical system and wiring harness of the present invention are conventional, commercially available components unless otherwise indicated. This is intended to include electrical components and circuitry, wires, fuses, soldered connections, circuit boards and microprocessor components.

Generally, unless specifically otherwise disclosed or taught, the materials from which the metallic parts (e.g., the barrel, end effector, etc.) of the present invention are formed are selected from appropriate materials such as aluminum, steel, metallic alloys. The handle may be formed of various plastics or the like.

Despite the foregoing indication that components and materials for use in and for forming or fabricating the surgical instrument of the present invention may be selected from commercially available, appropriate items, the following detailed description sets forth specific items and steps for use in the present invention, although it is possible that those skilled in the state of the art will be able to recognize and select equivalent items.

Figure 3:
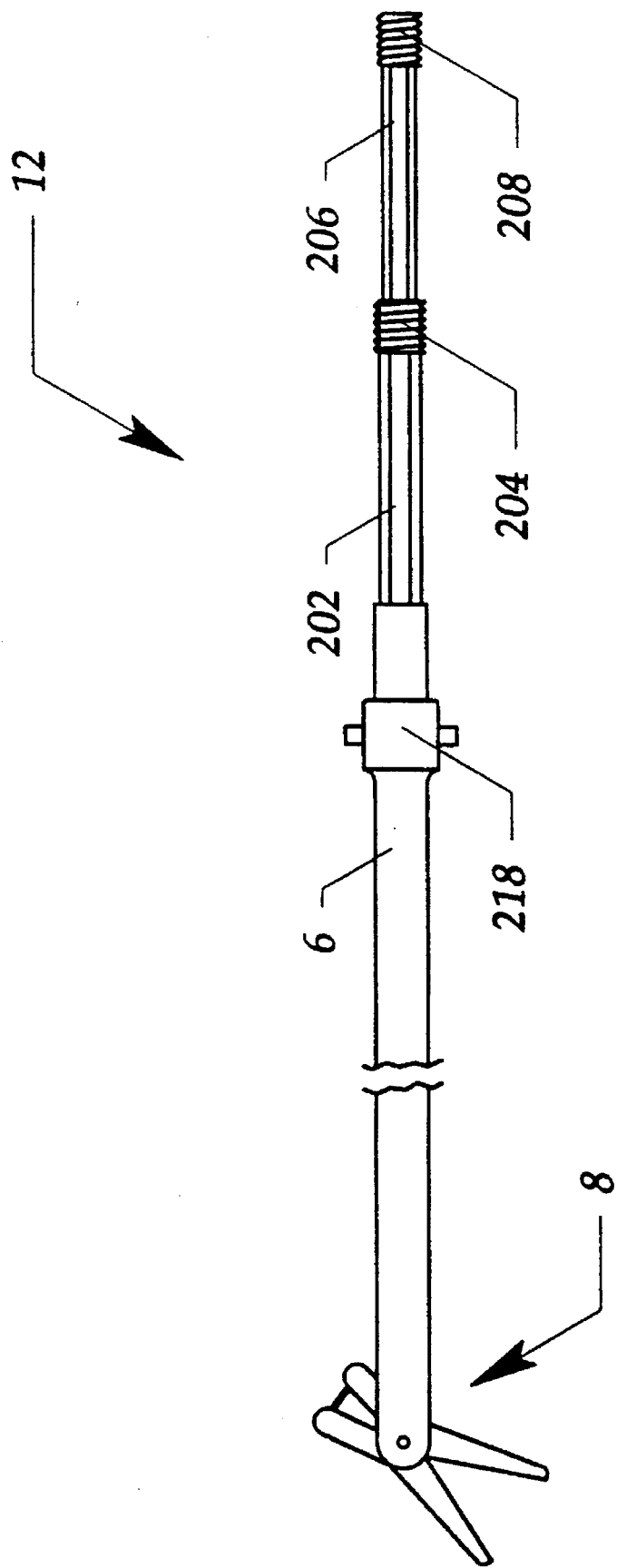
FIG. 3 is an elevational view of one embodiment of the barrel and end effector of the present invention.
Figure 4:
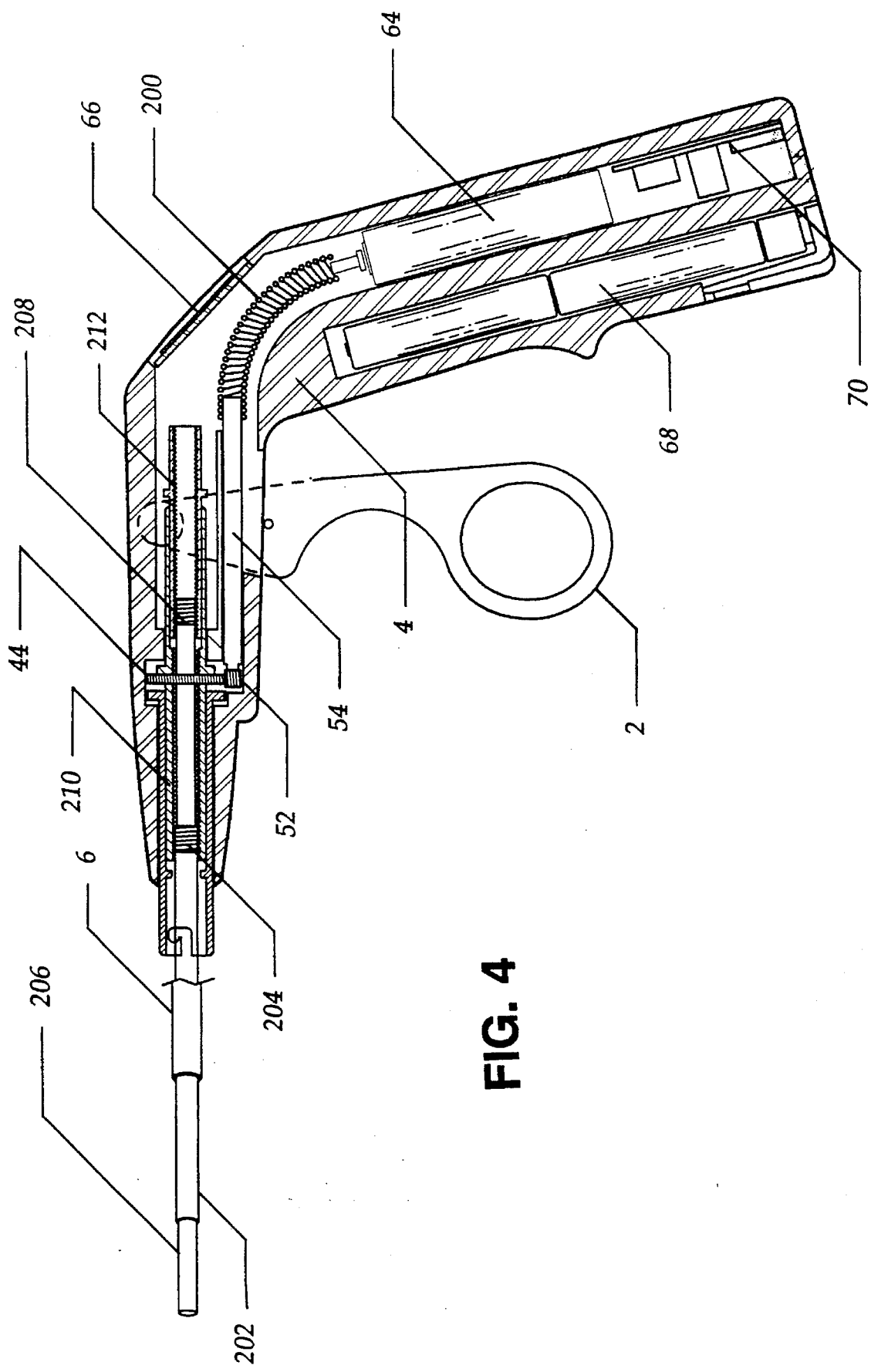
FIG. 4 is an elevational view of the handle of the present invention, partially in section, depicting the motors and actuation mechanisms with portions of the barrel connection and rotation mechanism removed for clarity.
Figure 5C:
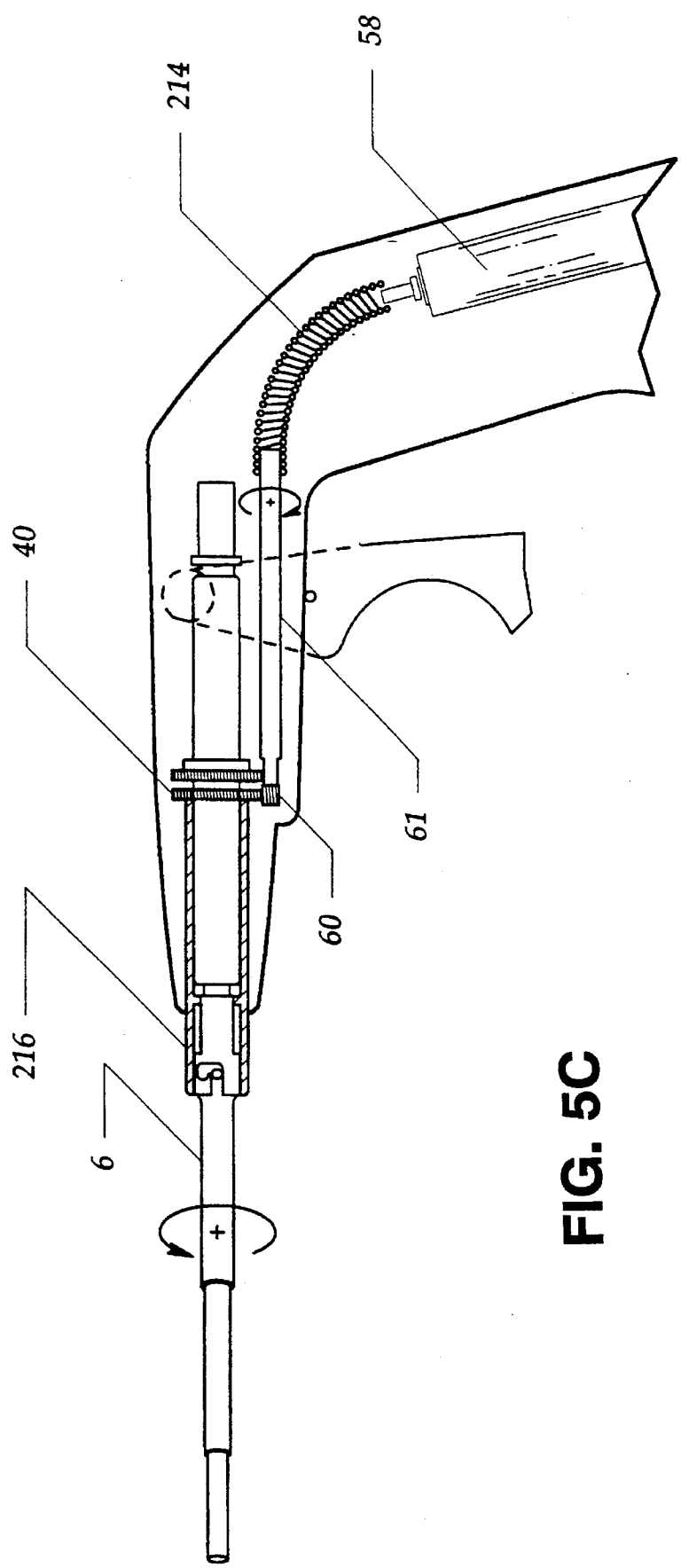
FIG. 5C is a view similar to that of FIG. 4 and depicts the axial rotation of the barrel.

The tubular member or barrel 6 of the instrument houses linkage means 12 (see, for example, FIG. 3) for closing and rotating the end effector 8, rotating the barrel 6 and, referring to FIGS. 4 and 5, includes a disengagement mechanism to allow removal of the barrel 6 from the handle 4. In FIG. 1, the end effector 8 is illustrated as a scissor-like working tip. However, the end effector 8 may be graspers, extractors, clamps, forceps, retractor, biopsy and other devices useful during surgery. The barrel 6 and/or end effector 8 may be disposable or reusable.

Figure 2A:
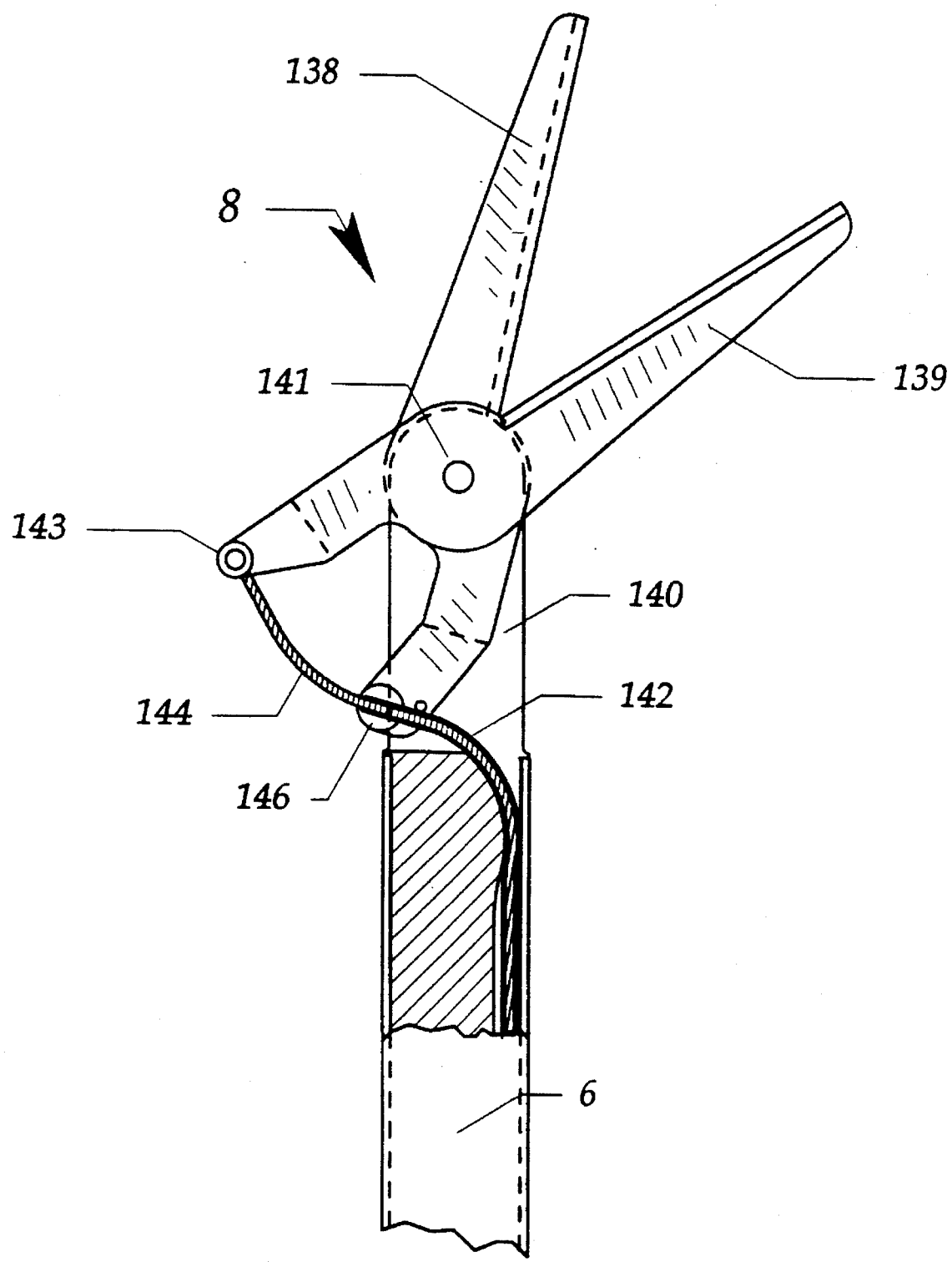
FIGS. 2A–D are elevational views, partially in section, depicting an embodiment of the end effector utilizing solid tubing as the sheath of a control cable.
Figure 2B:
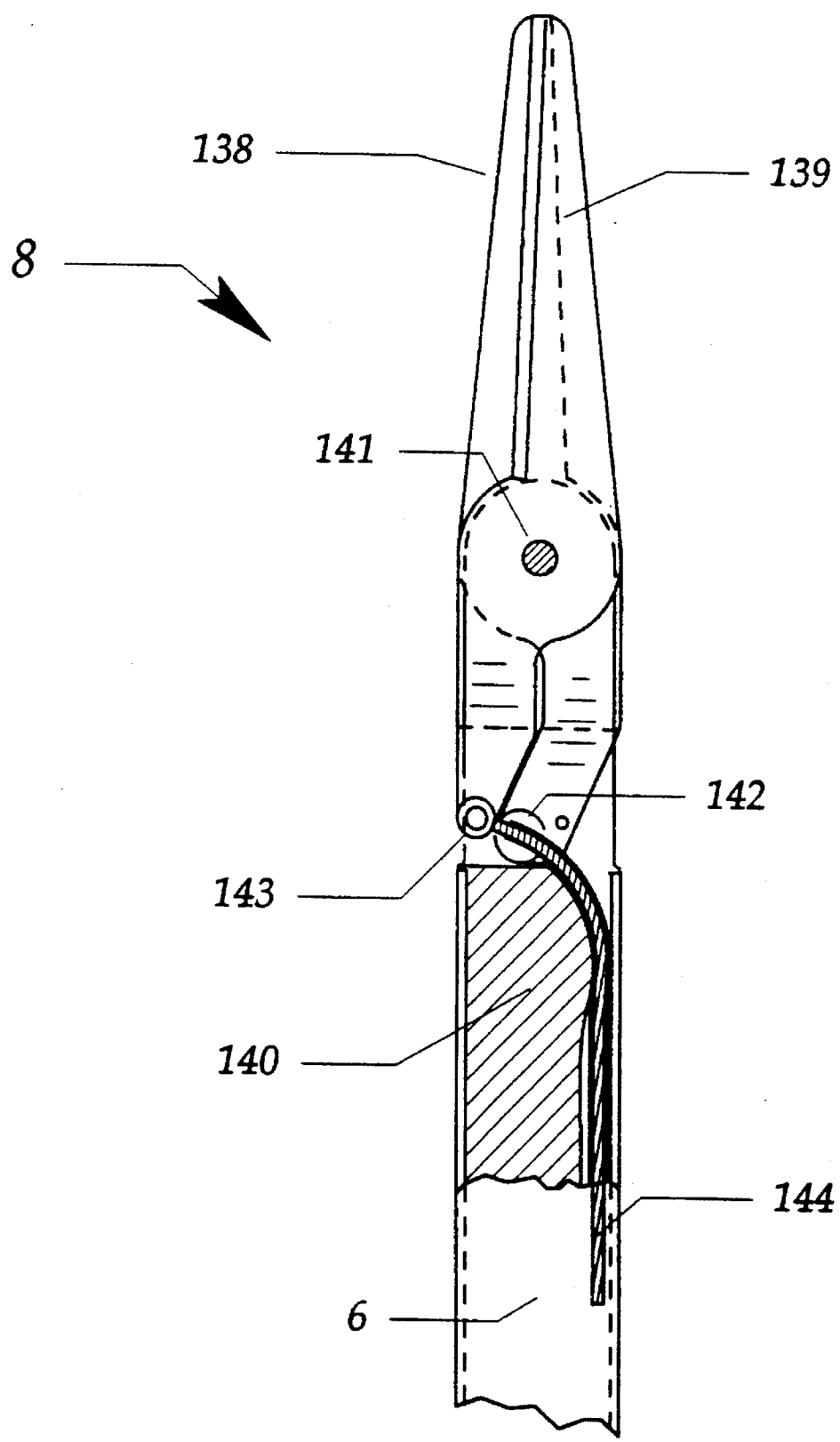
Figure 2C:
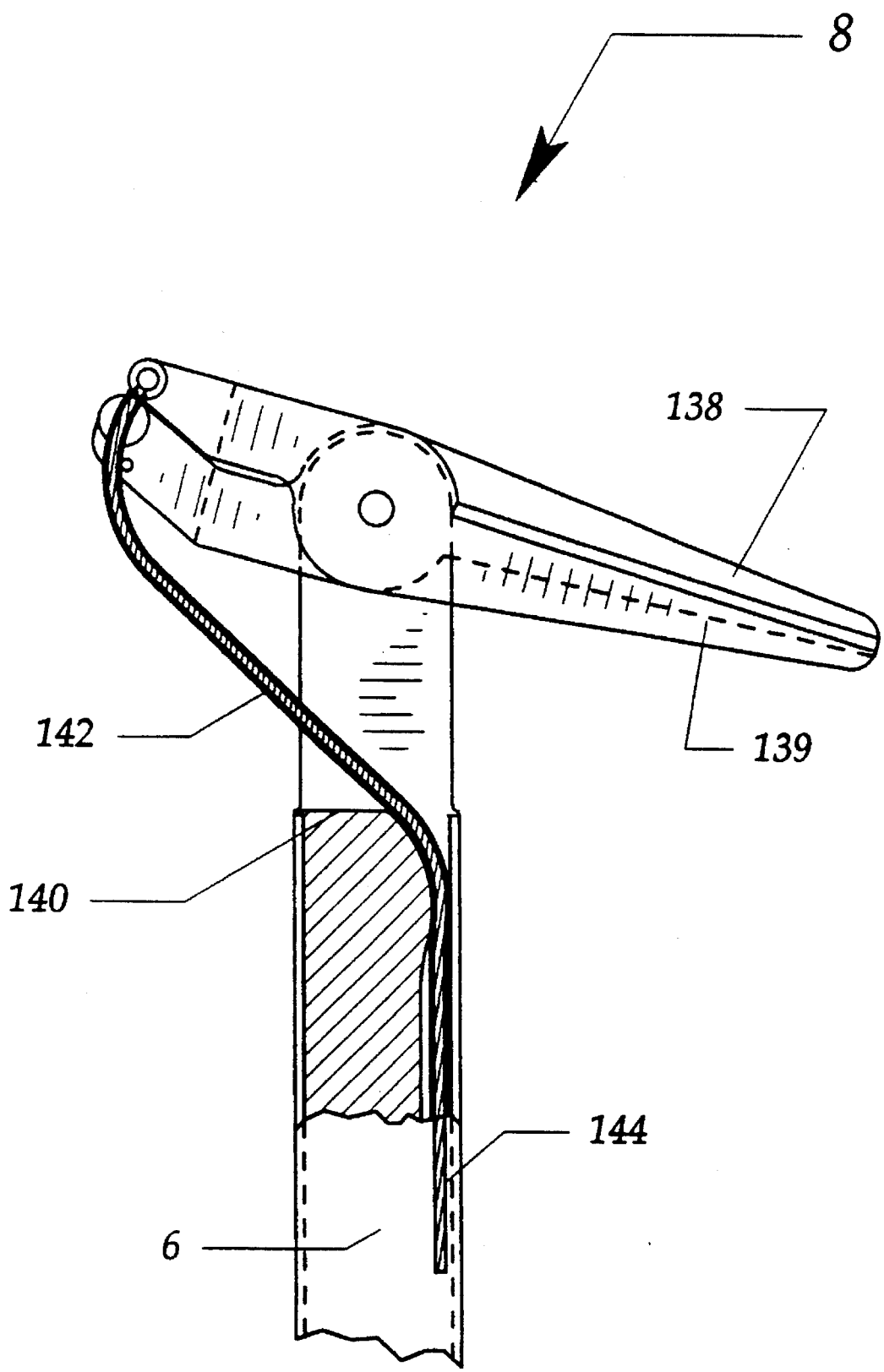
Figure 2D:
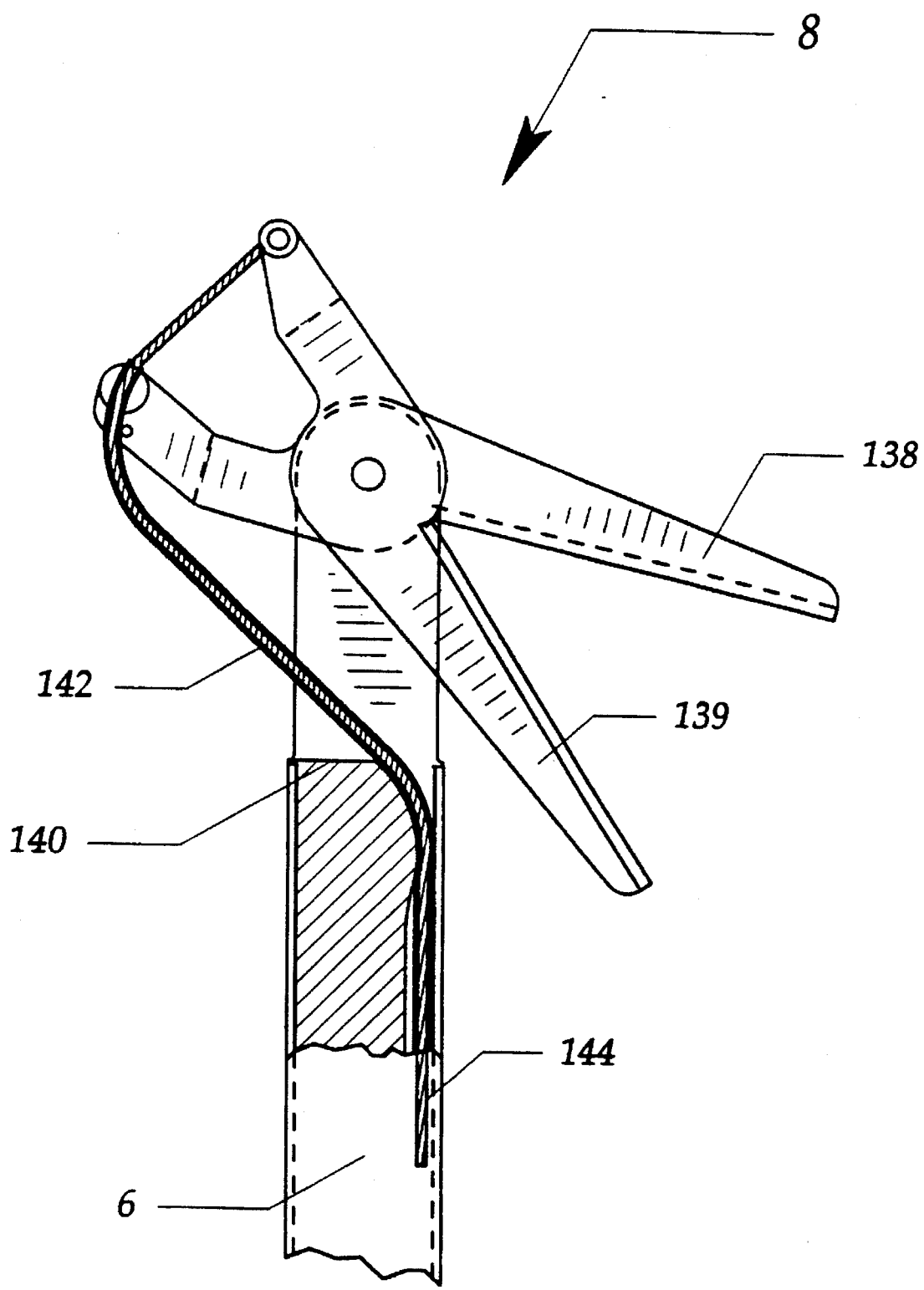

Referring to FIGS. 2A–D, a preferred embodiment of an end effector 8 is depicted. Two cutter end effector pieces 138, 139 are mounted pivotally in a fork 140 by a pivot pin 141. One elongated member, a super elastic metal tube (e.g., drawn nickel-titanium) 142 is attached to the proximal end of the end effector piece 138 via pivot 146. The sheath 142 depicted is an extruded tube, but a wound-wire or a suitable functional equivalent will work as well. The sheath 142 functions as a tension and compression member. A slot is formed within the barrel 6 so as to confine and guide the sheath 142; the slot is configured so as to define a radius which curves the tube approximately normal to the blade 138. Inside the sheath 142 is another elongated member which is a small diameter wire core 144 which is free to slide longitudinally within the sheath 142. The wire 144 is attached to the end effector piece 139 via pivot 143, and functions as a tension and compression member such that extension or retraction of the wire 144 causes opening and closing of the end effector pieces 138, 139 relative to each other as depicted in FIGS. 2A and B. Pivoting of the end effector pieces 138, 139 in unison while open or closed is accomplished by pushing the sheath 142 and wire 144 together in the distal direction, i.e., toward the end effector 8. This pushing causes the sheath and wire to extend or "snake" laterally relative to the end effector 8 as depicted in FIGS. 2C and D. Once positioned at an angle, up to and exceeding 90 degrees relative to the barrel 6 as depicted in FIG. 2D, opening and closing the end effector pieces 138, 139 is accomplished by pushing or pulling the wire core 144 relative to the sheath 142. Pulling the external sheath 142 would cause the end effector pieces 138, 139 to resume a straight ahead position with respect to the barrel 6 of the instrument as depicted in FIG. 2B.

Still referring to FIG. 2A, the point of attachment of the sheath 142 and the wire core 144 to the end effector pieces 138, 139 may be a single point as shown or may take the shape of elongated slots with the point of cable connection being slidable within the slots in the proximal ends of the end effector pieces (not shown). The slots and the end effector pieces may be straight or curved in order to obtain a direct and fair lead of the sheath core 144, thereby minimizing bending and friction of the core 144 in its sheath 142. Additionally, the slots may be angled or oriented to provide increased leverage or mechanical advantage for the core 144 upon either opening or retraction.

FIG. 3 shows additional details of the preferred embodiment of the removable end effector, including the tubular barrel 6 and end effector 8 of the present invention. The end effector 8 is attached to the distal end of the tubular barrel 6 and a bayonet fitting 218 is attached to the proximal end of the tube. The attachments 218, 204, 208 may be a threaded section or other torsional and axial engagement. A means for pivoting and moving the end effector is located within the barrel 6. More specifically, internal to the tube 6 and slidable within it are a pair of shafts. One shaft, first control rod 202, has a threaded fitting 204 attached to its proximal end. However, fitting 204 may be a bayonet fitting or other connection. Internal to the first control rod 202 is a second shaft, control rod 206, also with a fitting 208 attached to its proximal end. The fitting shown is a threaded section 208, but it may also be a bayonet fitting. The two sliding elements of the end effector, 202 and 206 may be slid longitudinally within one another and within the tubular barrel 6, however they are restrained from rotating to allow engagement of the screws or bayonet fittings. In the embodiment shown in FIG. 3, the two control rods are hexagonal telescoping tubes which can slide easily but not rotate except as a unit.

Figure 3A:
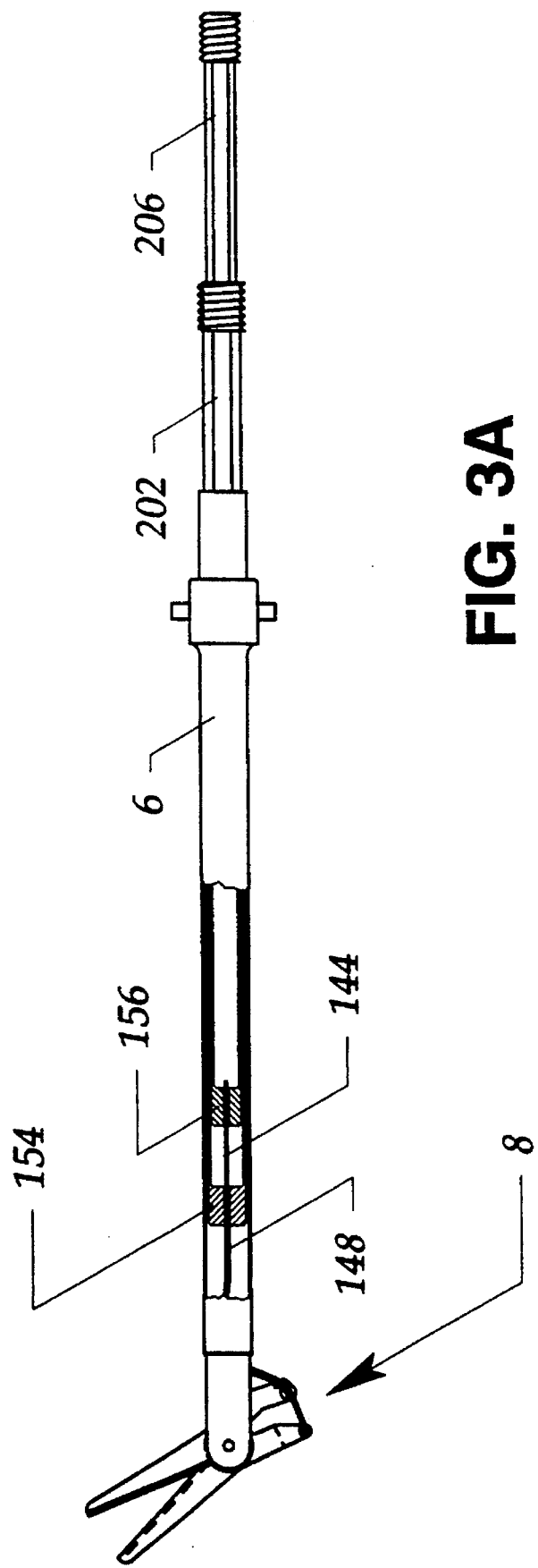
FIG. 3A is an elevational view similar to that of FIG. 3 and depicting one embodiment of the connection between an end effector and the linkage to the actuation mechanism of the present invention.

Now referring to FIG. 3A, details of the interconnection of the wire core 144 and sheath 148 to the control rods 202 and 206 are illustrated. The proximal end of wire core 144 is attached to control rod 206 at junction 156. Similarly, the proximal end of sheath 148 is connected to control rod 202 at junction 154.

Referring to FIGS. 4 and 5, the handle 4 houses the actuating means or operating mechanism. In this preferred embodiment of the present invention, closing the end effector is performed manually by retraction of finger trigger member 2. The barrel 6, which is an integral part of the end effector assembly shown in FIG. 3, is inserted into the distal end of the handle 4, and is connected to a pair of elongated rotatable nuts 210, 212 which are concentric with the centerline of the end effector barrel 6. The two control rods 202 and 206 are constrained from rotating within the barrel tube 6, but can slide lengthwise inside the tube, and each control rod has a threaded section 204, 208 on the proximal end. When attached to the handle, each threaded section 204, 208 mates to its own elongated nut 210, 212; screw 204 engages nut 210 and screw 208 engages nut 212. The two nuts 210, 212 inside the handle rotate together, however nut 210 is restrained axially in position, while the proximal nut 212 is attached to the trigger by way of a sliding yoke and can move proximally.

Thus, when the trigger 2 is pulled, as shown in FIG. 5B, the proximal nut 212 pulls the internal control rod 206, pulling in turn the center core 144 (FIG. 2A) which moves relative to the external sheath 142 (FIG. 2A). Despite movement of trigger 2, internal control rod 202 is held stationary in the barrel 6. Therefore, the continued action closes one end effector piece 139 against its neighbor 138, resulting in a pinching action. The end effectors pivot when the two nuts 210 and 212 are turned as a pair and both control rods 202, 206 screw forward inside their respective nuts, shown in FIG. 5A. In this preferred embodiment, nut 212 has a hexagonal or spline shape on its exterior which engages a mating profile on the proximal interior end of nut 210. The mating shapes allow the two nuts to slide relative to one another, yet rotate together. Elongated nut 210 is driven by a spur gear 44 which meshes with a pinion 52 on the distal end of shaft 54 which is in turn driven by flex coupling 200, driven by the small gearmotor 64 shown in FIG. 4.

The thread pitch of the two screw/nut pairs 204/210 and 208/212 are identical in order to fully decouple end effector pivoting and closing. However, because the end effector barrel 6 and control rods 202, 206 should be easily detachable, it is desirable to utilize two different thread diameters so that the inside control rod 206 and screw 208 can reach through nut 210 and engage nut 212 without having to thread the rod the entire length of nut 210. Attachment of the end effector assembly is straightforward (see FIG. 5A): The barrel assembly is inserted into the distal end of the handle 4 and the "pivot straight" button 66 is depressed to drive the nuts 210, 212 forward, threading the two screws 204 and 208 in a proximal position. When the tubular barrel 6 is drawn fully into the handle, the bayonet fitting 218 (see FIG. 3) can then be locked into the axially rotatable element 216 (see FIG. 5C). Disconnecting the end effector is accomplished by unlocking the bayonet fitting, holding the tubular barrel 6 to restrain rotation and pushing the button 66 marked "back" to unscrew the two control rod screws 202, 206. In this preferred embodiment, rotation of the nuts 210, 212 is accomplished preferentially with small gearmotors, resulting in much improved utility, and easier operation. It may however be done manually with small knobs or levers.

Referring to FIG., 5C, a separate gearmotor 58, through flexible drive 214, turns shaft 61 and pinion 60 which engages gear 40. Gear 40 is in turn coupled to tube 216 and the female part of the bayonet fitting which engages the tubular barrel 6 on the end effector. This in turn rotates the entire barrel 6, including control rods 202, 206 and end effector 8. The two motors 58, 64 (see FIG. 4) are located side by side in the handle and incorporate parallel and independent drive trains, one shown in FIG. 4, the other in FIG. 5C. There are significant advantages to the surgeon to have the rotation feature motor driven. However, rotation of the end effector may alternatively be accomplished manually quite simply by incorporating a knob on the distal end of the handle which allows direct rotation of the tubular barrel 6.

Figure 6:
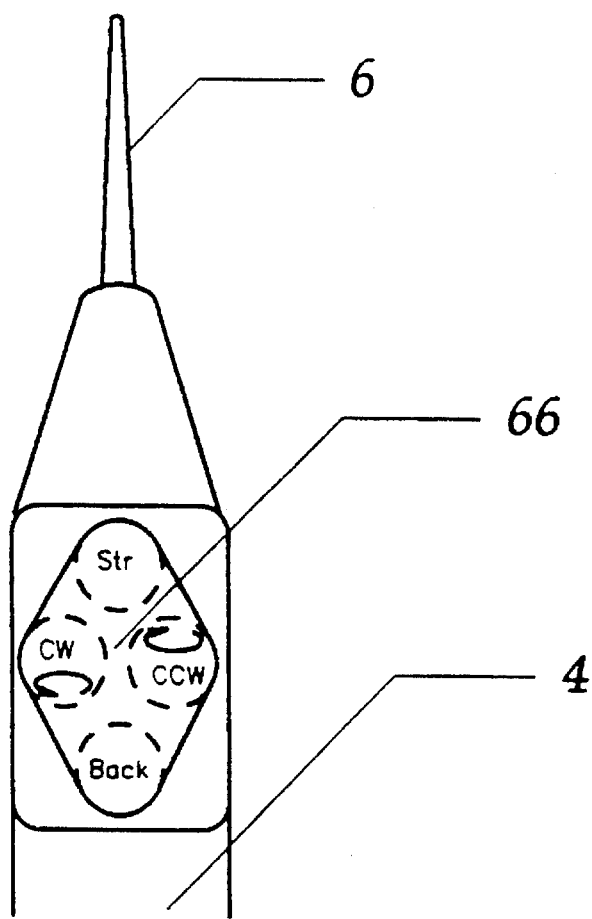
FIG. 6 is a rear elevational view of a portion of the handle.

FIG. 6 shows one of the controllers for operating the instrument, in this case, the control switch 66 mounted on the handle 4. A small label covering switch 66 shows the effect of moving the control switch 66 in each respective direction. The switch 66 may be controlled easily with the thumb of one hand, and has the following effects: (i) pushing the switch 66 label "str" causes the end effector to pivot to the straight ahead position (shown in FIG. 2B); (ii) pushing the label "back" causes the end effector to pivot backward (shown in FIG. 2C); (iii) pushing the label "CVV" causes simultaneous counterclockwise rotation of shaft 36, barrel 6 and end effector 8; and (iv) pushing the label "CCW" causes simultaneous counterclockwise rotation of shaft 36, barrel 6 and end effector 8. Movement in this embodiment is discrete and not proportional, although minor modification of control electronics 70 (FIG. 7) could enable such proportional control.

Figure 7:
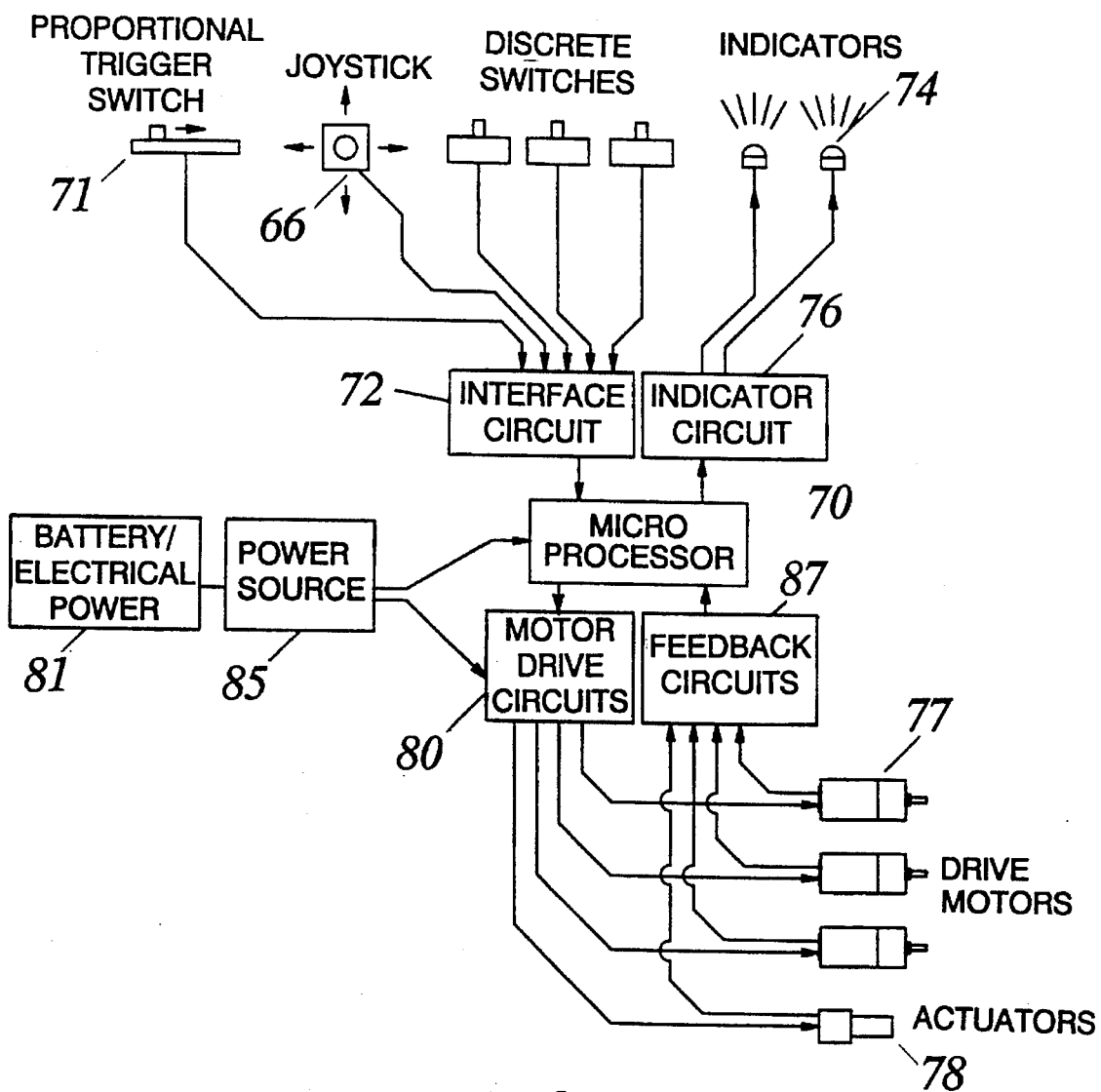
FIG. 7 is a schematic diagram depicting the integration of a microprocessor into the electronic embodiment of the instrument of the present invention.

FIG. 7 is a schematic diagram of a microprocessor controller and associated circuitry for use with the surgical instrument of the present invention. Each of the functional blocks may or may not be a discreet functional circuit. Input into the microprocessor 70 from the operator is through switches, variable resistors, encoders, or other devices (indicated generally at 66, 71 ). Depending on the type of component used, the microprocessor 70 may require an interface circuit 72. Similarly, the status indicator lamps 74 may also require some external drive circuitry 76. The motors or other actuators 78, of course, cannot be driven directly from the microprocessor 70; each requires a drive circuit 80 to regulate the power supply 81 to them. Feedback from the motors or actuators 77, 78 is provided by encoders or limit switches (not shown), controlled by and conditioned by a feedback circuit 87. In some instances, it may be desirable to avoid feedback control, relying instead on a feed forward system (not shown) utilizing, for example, stepper motors instead of servo motors. Electrical power may be removed from the device via an electrical switch 85, providing on-off battery connection.

The present invention may incorporate a single board computer with microprocessor functionality equivalent to a Motorola 68HC11 processor with a programming language in internal ROM. The control software may be contained in EPROM. The 68HC11 processor contains a section of EEPROM which is used to store set points, etc., while the instrument of the present invention is turned off. The single board computer is operationally coupled to a servo drive control module 80 containing motion control IC's (for example, Hewlett-Packard HCTL-1000) which control the multiple drive motors 77. The selected microprocessor itself may be programmed to perform the servo control functions of the separate motion control IC's. Interfaces 72 also may be provided to decode the output of the joystick 66 and proportional switches 71 used by an operator.

Now referring to FIGS. 8–17, the software for the instrument of the present invention is composed of a main loop 390 (FIG. 8b) which executes continuously while the instrument is switched on, and several secondary loops (FIGS. 9–17) which control special functions such as reciprocating, cutting or vibration and the like. One primary purpose of the main loop 390 is to query the joystick and other control switches to determine whether an operation is desired. If so, the appropriate subroutine is called. The main loop 390 runs every 20 milliseconds while the instrument is on and may be adapted to check continuously system operating parameters and update the displays, represented in FIGS. 9 and 17, respectively. The only way to exit the main loop 390 is to remove power from the instrument.

Motor movement is accomplished by the motor control chips which are run in the positional error mode. Relative and absolute positions are always maintained to assure repeatable movement and an absolute zero reference. The absolute positions are established during the initialization routines (FIG. 9), wherein motors are driven from limit to limit to establish the absolute zero reference point. Each motor movement is measured relative to a target position for that encoder, the position calculated by the microprocessor 70. The speed is multiplied by a gain factor used to allow a user to control distance sensitivity. If a position error ever exceeds an error limit, which is determined by motor limits during initialization (FIG. 9), then the main control loop 390 infers a component failure, declares an error and lights the appropriate lamp. Special functions such as reciprocating, cutting, vibration, autozero and barrel disengagement are handled in separate routines FIGS. 12–16.

The handling of switch closure and joystick movement is straight forward. Because the movement routines are separate and distinct, the logic for each motor move is separate from another. However, because the main loop 390 executes so rapidly, the motion control ICs will accept destination positions and rates, and because the motors have mechanical inertia, the resulting motor movement is functionally concurrent. This allows simultaneous movement in all three axes. Other operator setable functions such as speed, force, and joystick sensitivity may be programmed by a suitable set of soft keys or dedicated buttons. Information may be displayed through the indicator lights or a display such as an LCD.

Operation of the instrument 2 of the present invention is broadly depicted by the flow diagram of the main program loop for the microprocessor depicted in FIG. 8. Power is provided to the instrument at block 400. The program proceeds through the EEPROM block 402 and reinitializes at block 404 if there is a default state. Initializing the hardware and stating the variables, as well as checking the battery occurs next at block 406. This operation is set forth in more detail in FIG. 9, beginning with initialize all block 407 and proceeding to the check battery block 408, the barrel rotation controller 410, pivot controller 412, and end effector closing controller 413. The running state flags are reset at block 414 and any error is cleared at block 416. Initializing ends at block 418, at which point the program flows to the display power on block 419 (FIG. 8a).

Figure 17:
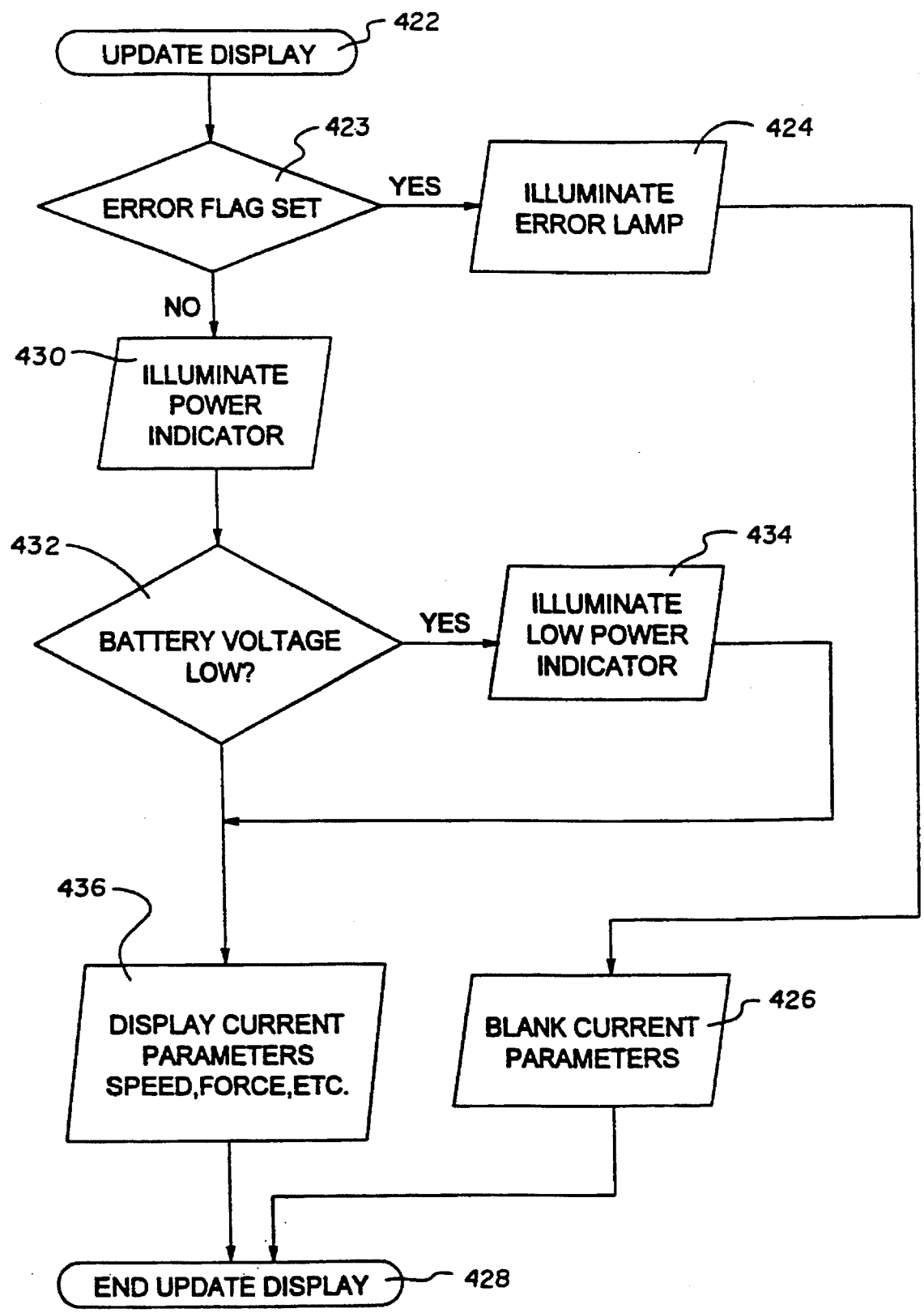

After error query block 420, at block 421 the displays are updated, as shown in FIG. 17, beginning at update display block 422. Initially, the error flag set query is made at block 423 and, if the answer is yes, the error lamp is illuminated as represented at block 424, current parameters are blanked, block 426, and the update display ends at block 428. If there is no error detected at block 423, the power indicators are illuminated, block 430, and a battery voltage query is made, block 432. If voltage is low, the low power indicator is lighted at block 434 and the flow proceeds to display current parameters (including operational parameters such as speed, force, etc.), block 436. At that point, the end display update program is reached at block 428.

Figure 8B:
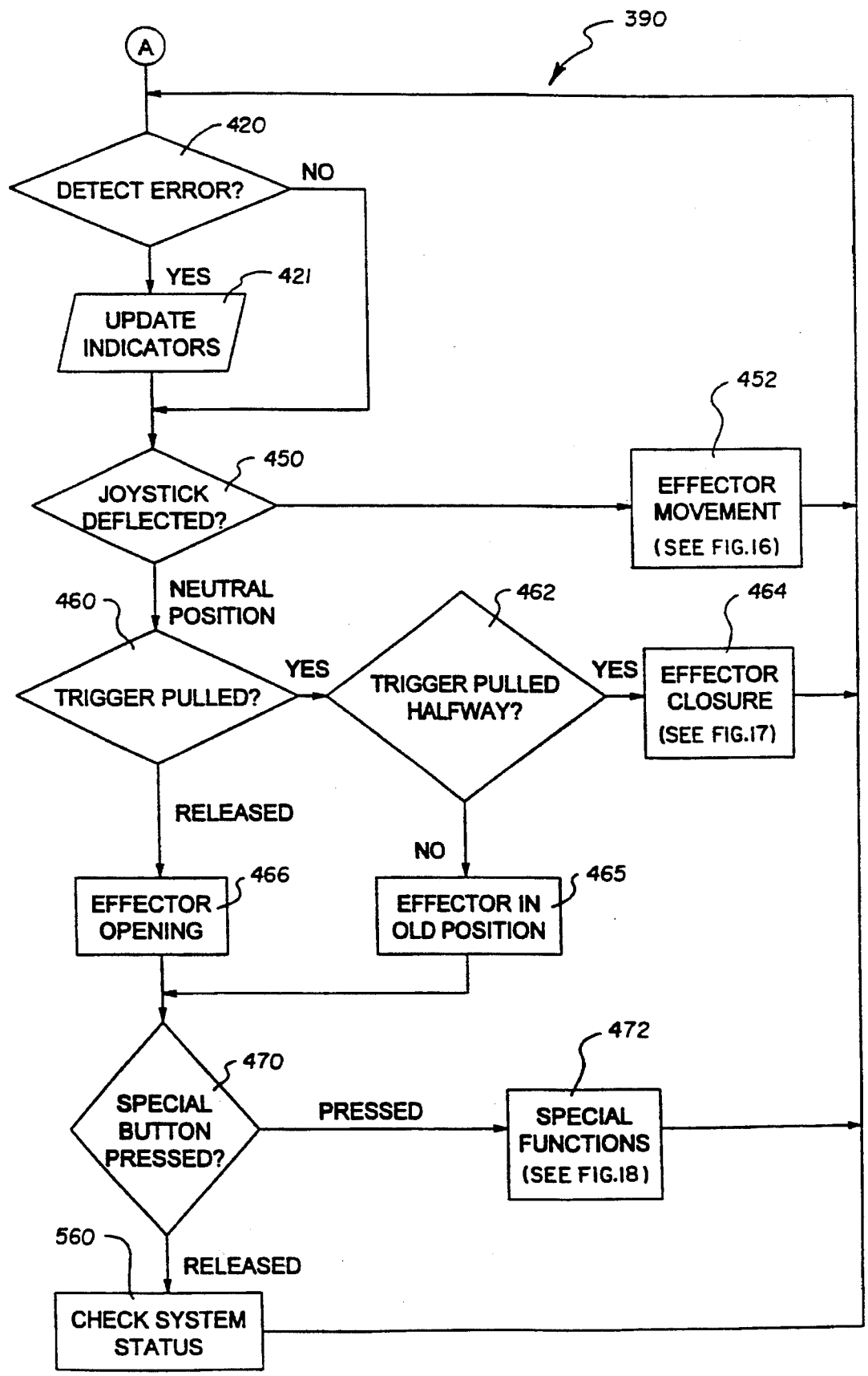
Figure 9:
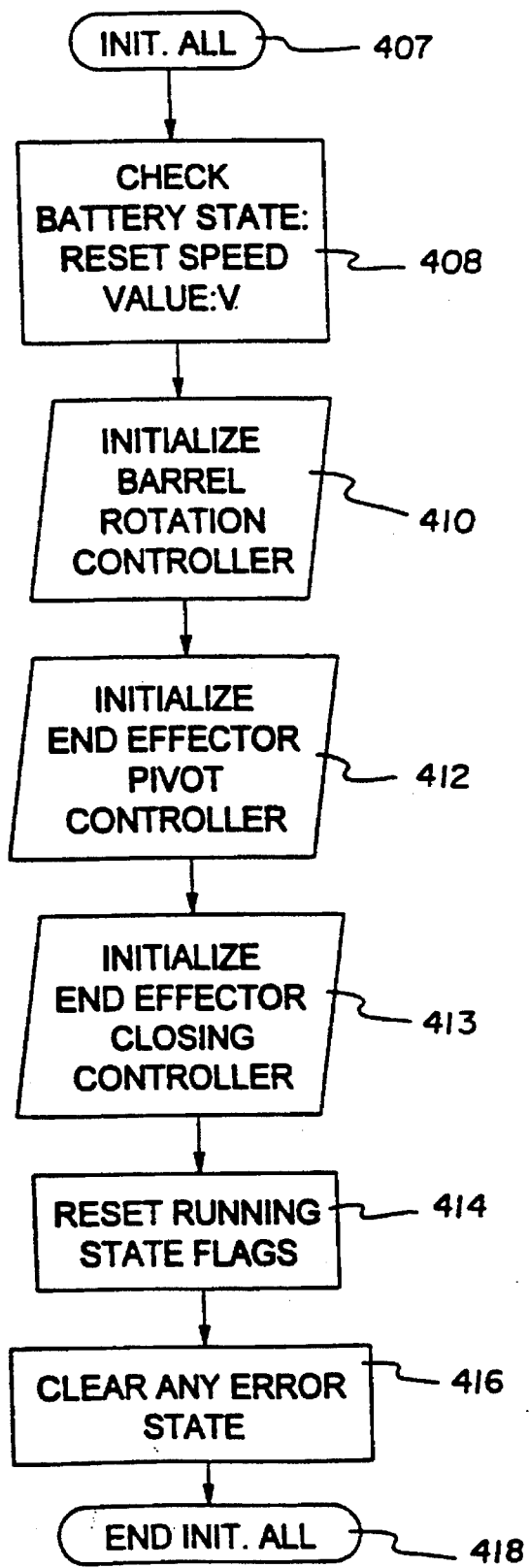
Figure 10:
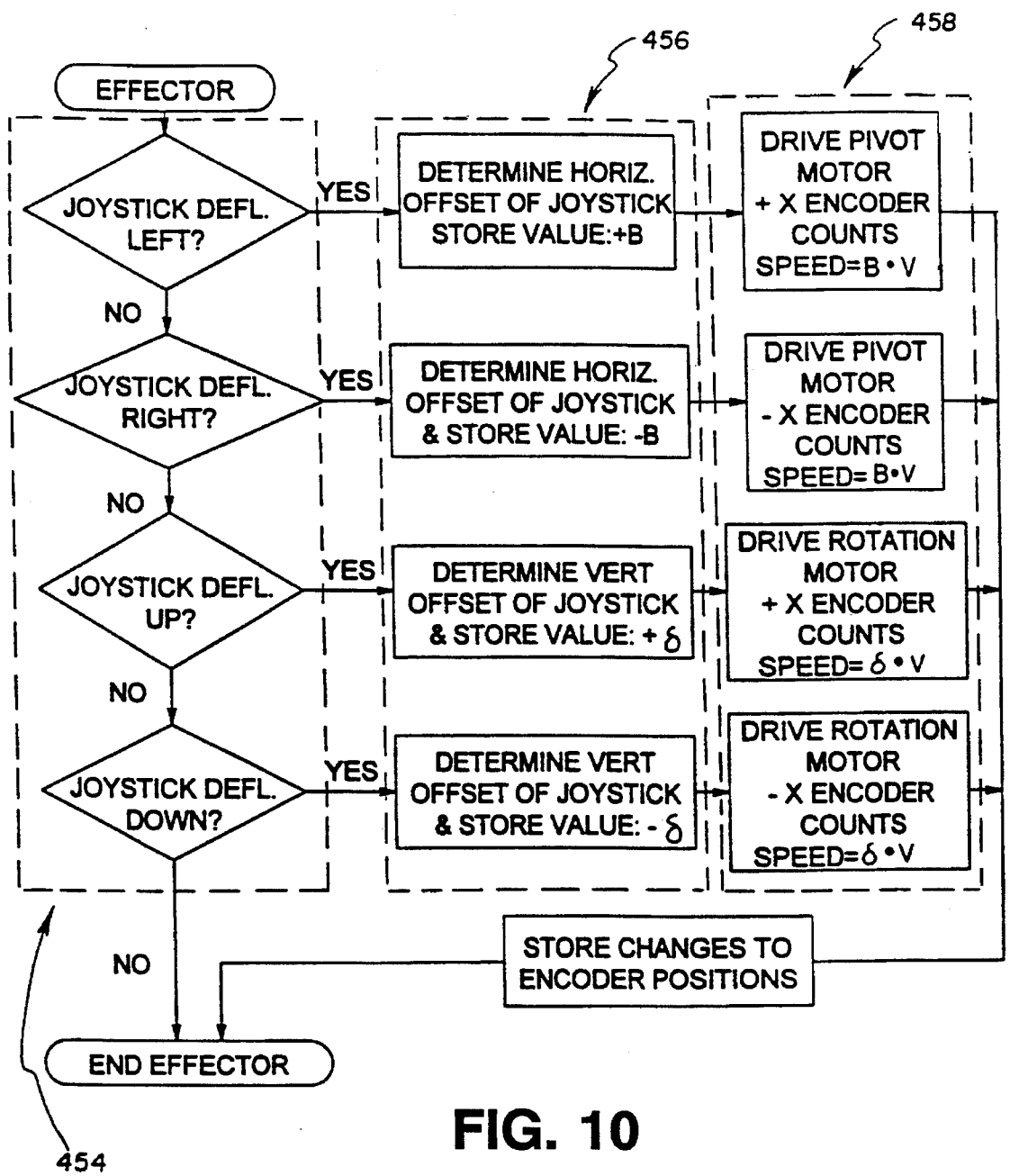

With further reference to FIG. 8b, if no errors are detected, use of the instrument may proceed to a specific inputs by the operator and queries by the program, such as the joystick query and movement blocks 450, 452, respectively. Referring to FIG. 10, the program flow controlling effector movement is set forth in more detail as a series of queries and comparisons indicated generally at blocks 454, 456, respectively, and input operational commands indicated generally at block 458.

Figure 11:
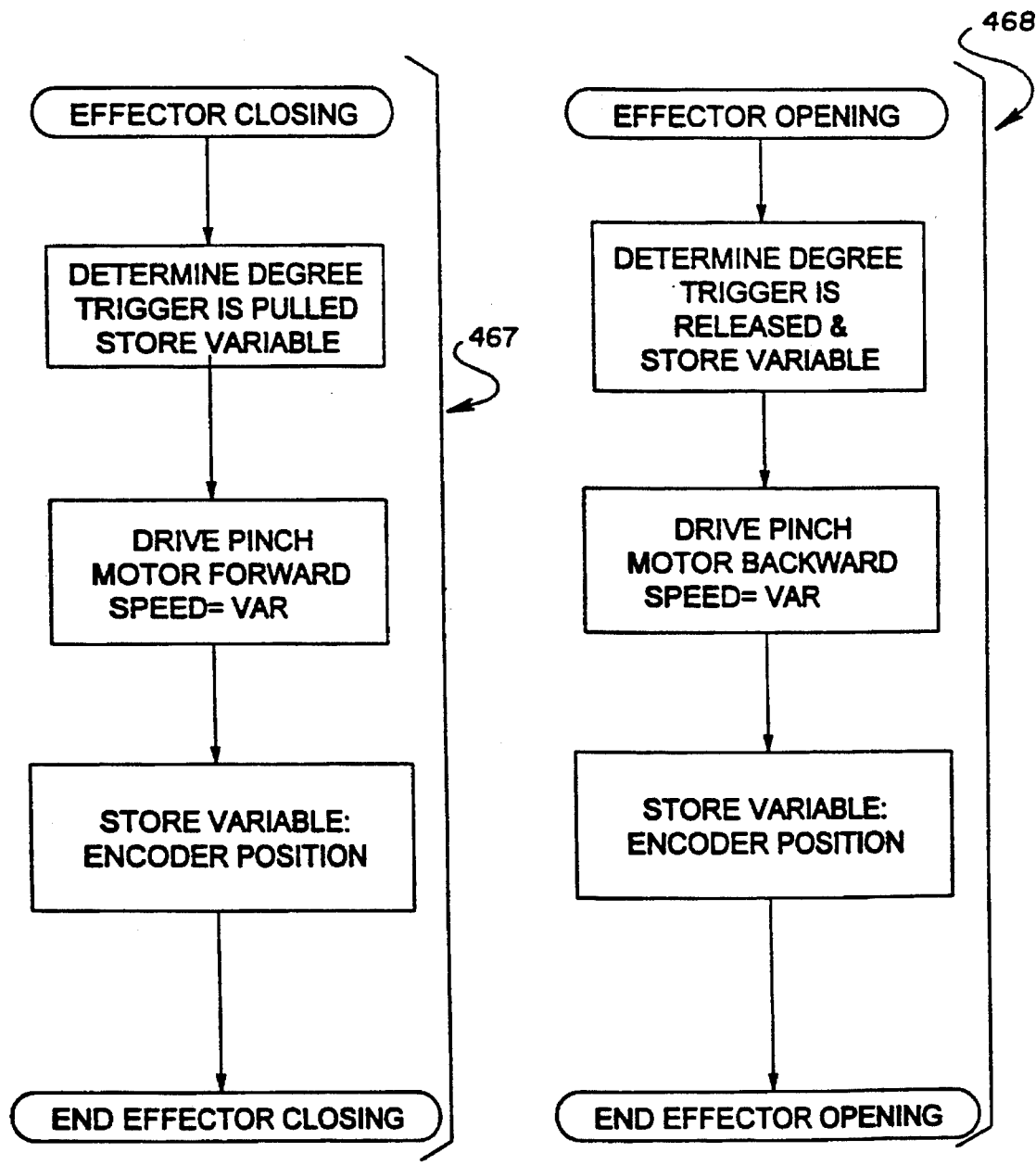

Similarly, the trigger 71 (FIG. 7) is monitored at the trigger query blocks 460, 462, (shown in FIG. 8b) resulting in effector closure function blocks 464, 465 and 466. FIG. 11 depicts the effector closing and opening sequence in exploded views at blocks 467 and effector opening likewise as exploder block 468, respectively.

Figure 12:
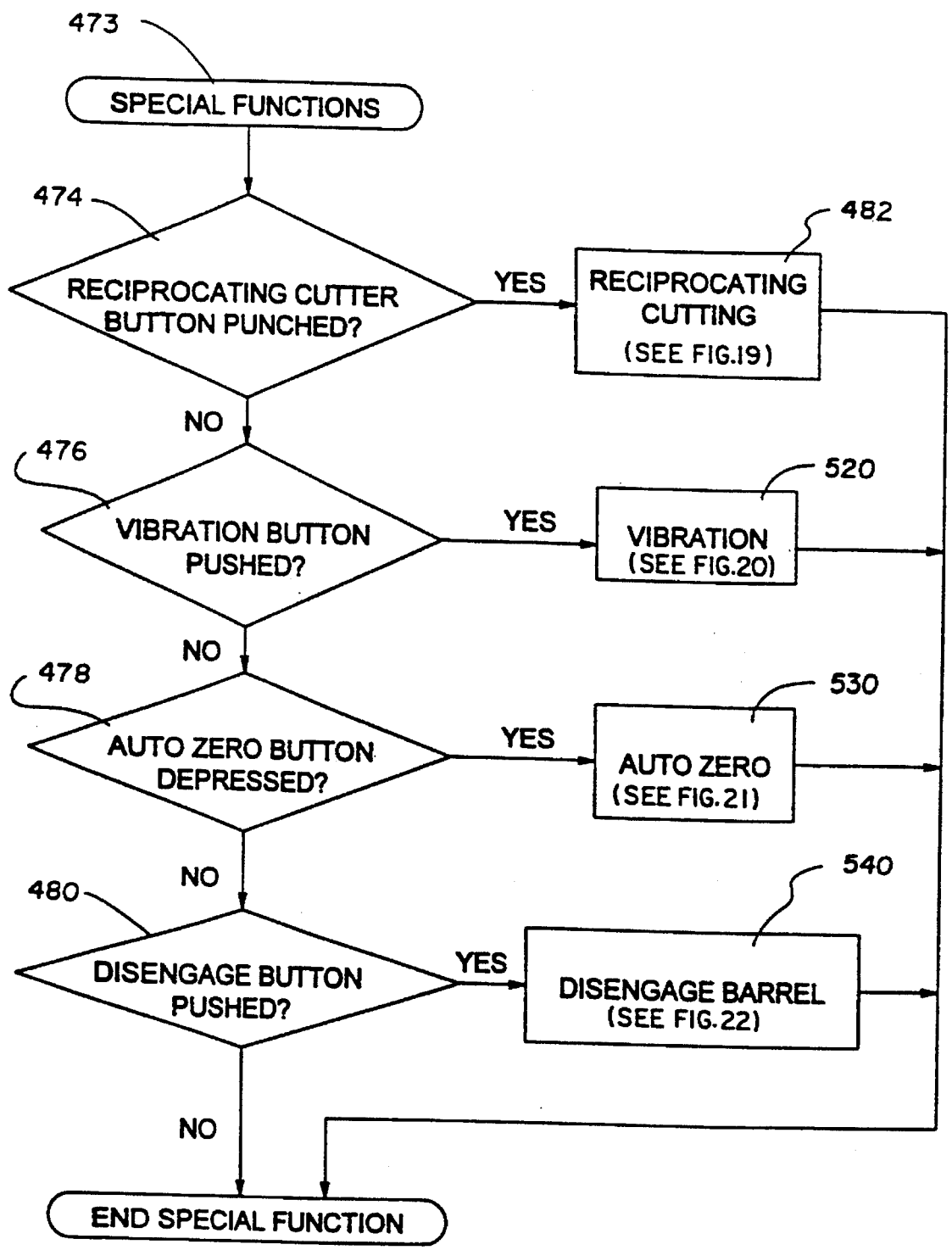

FIG. 8b reflects that the program includes a special function query, block 470, which, if a special function is required and actuated, directs the flow to block 472, set forth in further detail in FIG. 12. Block 473 begins the special functions flow then proceeds to query each of the special functions including reciprocating cutting, block 474, vibration, block 476, autozero, block 478, or the disengage function, block 480. With respect to the reciprocating query, if the answer is positive, flow proceeds to operational reciprocating cutting block 482, shown in more detail in FIG. 13.

Figure 13:
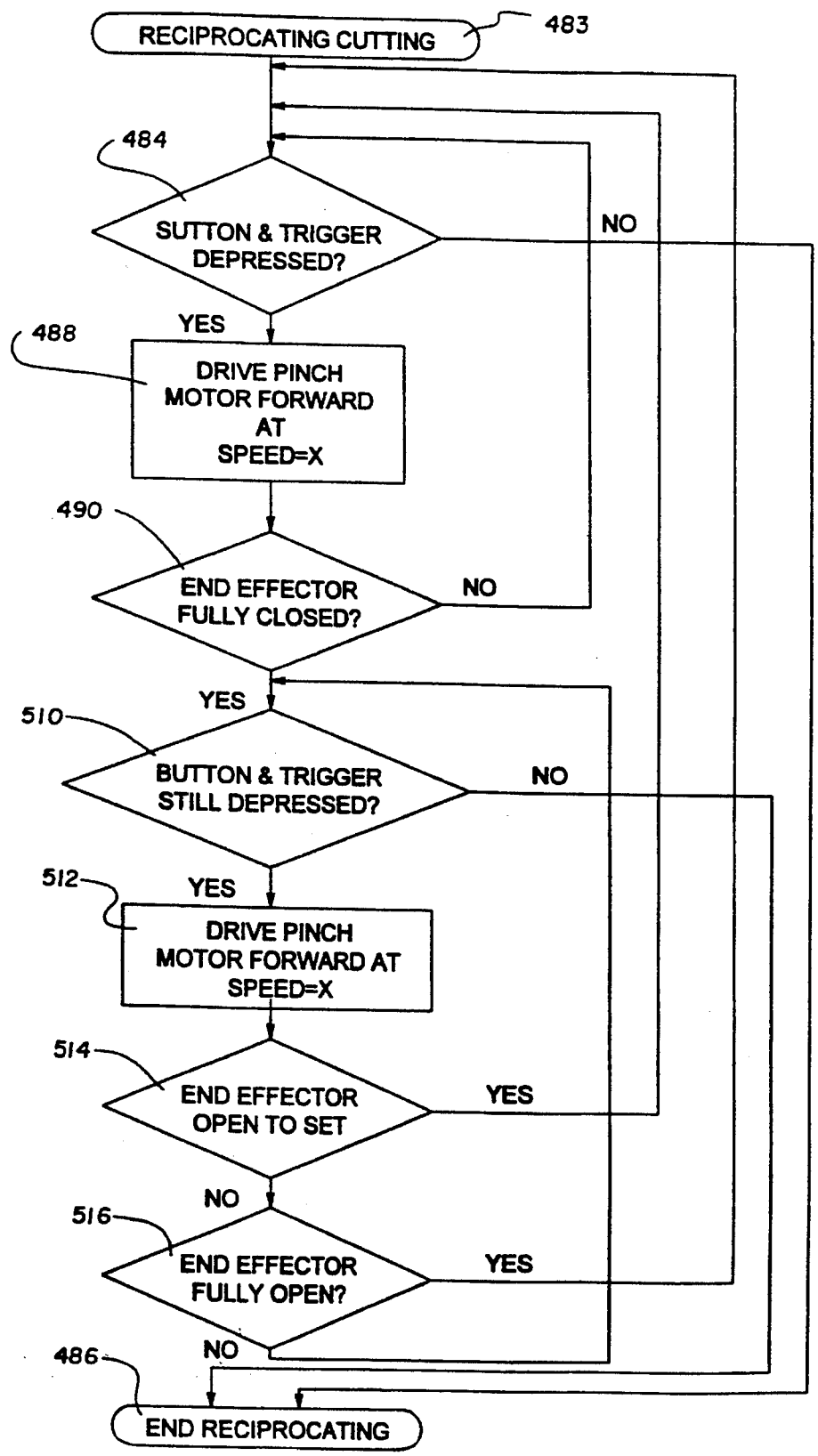
Figure 16:
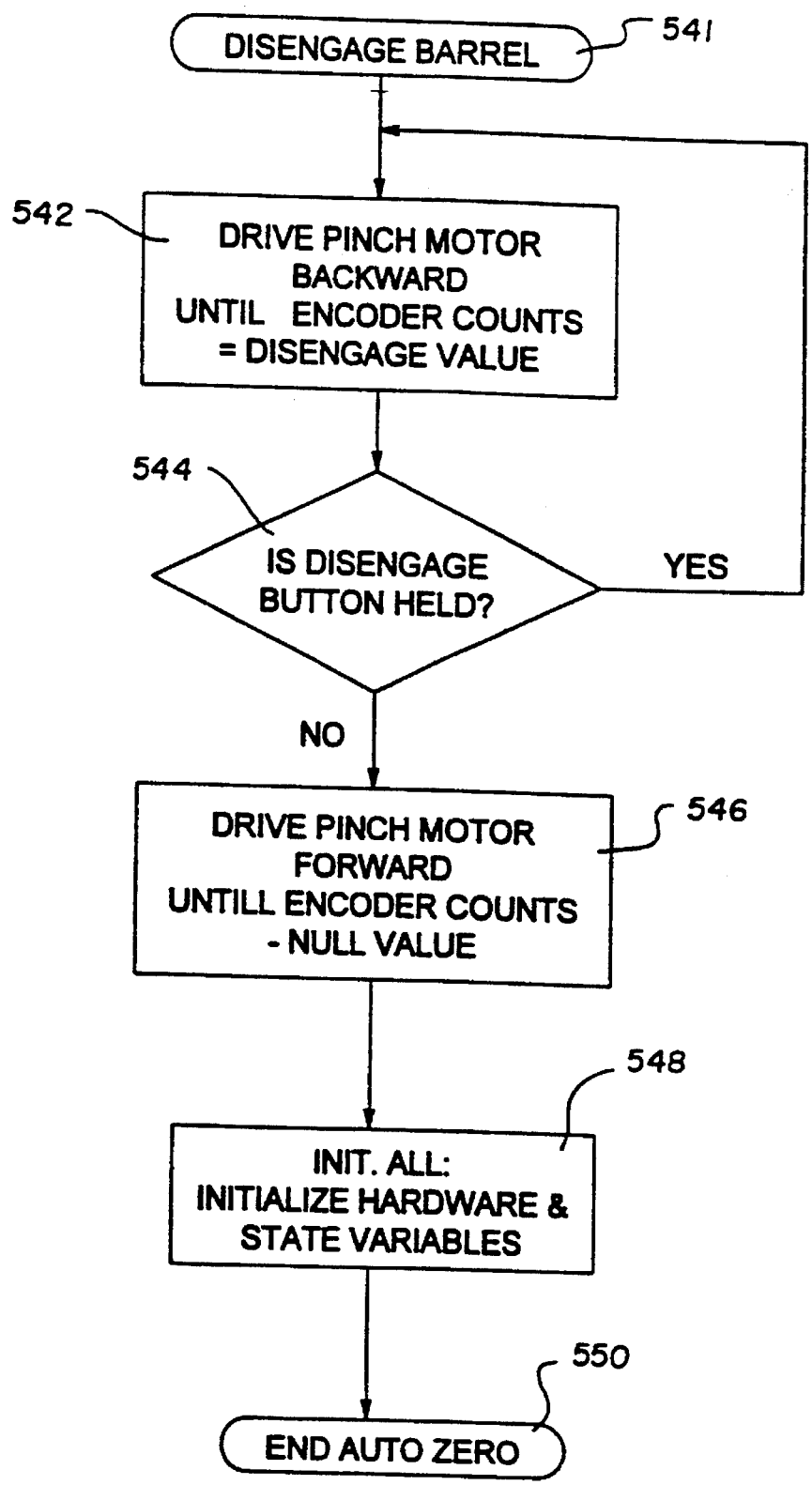

Referring to FIG. 13, the reciprocating cutting flow begins at block 483 and first queries whether the function has been requested at block 484. If the answer is no, the flow proceeds to end reciprocating, block 486. If the answer is yes, the motor is driven fully forward, block 488. The flow then proceeds to query whether the end effector is fully closed, block 490. If the answer is no, the program returns to the beginning, and if the answer is yes, a query is made as to whether the request button is still depressed, block 510. A negative response directs the flow to end reciprocating, block 486. If the answer is yes, the motor is operated, block 512, and the end effector is queried, block 514. If the answer is yes, the program returns to the beginning and, if the answer is no, a query is made as to whether the end effector is fully opened, block 516. If the answer is no, the program returns to the start point until the fully open state is reached.

Referring back to FIG. 12, the vibration query at block 476 leads to the vibration function, block 520, shown in further detail in FIG. 14. Upon actuation of the vibration request, block 521, the flow proceeds to drive the pinch motor, either forward, block 522, or backward, block 524. The program then queries whether the operating request button is still depressed, block 526; if the answer is yes, flow returns to the start, and if no, the vibration flow ends, block 528.

Again referring back to FIG. 12, the special functions include the autozero query, block 478. If answered positively, the flow proceeds to autozero function, block 530, set forth in further detail in FIG. 15. Flow at block 531 and, if actuated, the program drives the pivot motor forward/backward until a null value is reached, block 532. Similarly, the pinch motor and rotational motor are driven until null values are reached respectively, blocks 534, 536, and autozero ends, block 538.

Returning to FIG. 12, another query in the special function begins at the disengaged query block 480. If the answer is yes, the flow proceeds to block 540, to disengage the barrel as set forth in FIG. 16. This function flow begins at block 541. Next, the pinch motor is operated to equal the disengage value, block 542. At that point, the program queries whether the disengage button is still depressed, block 544, and if the answer is yes, the program returns to drive block 542. If the answer is no, the pinch motor is driven forward until a null value is reached, block 546, and the program flows to an initial all block 548 wherein the hardware is reinitialized and variables stated, reaching the end of the autozero program, block 550. The main program flow (FIG. 8) also includes a periodic check system function, block 560.

Figure 18:
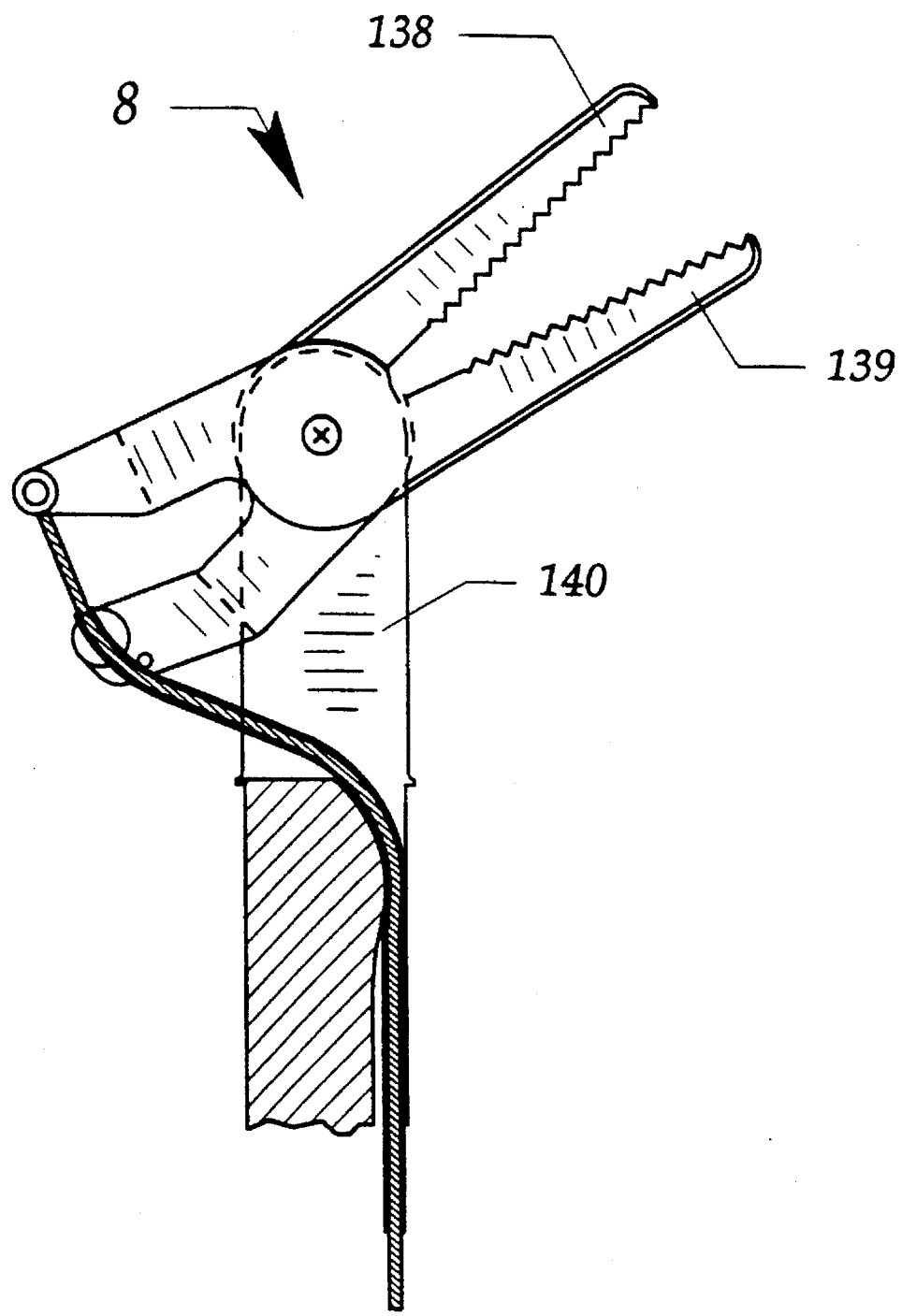
FIG. 18 is an elevational view substantially similar to that of FIG. 2, but depicting an end effector with dissection jaws.
Figure 19:
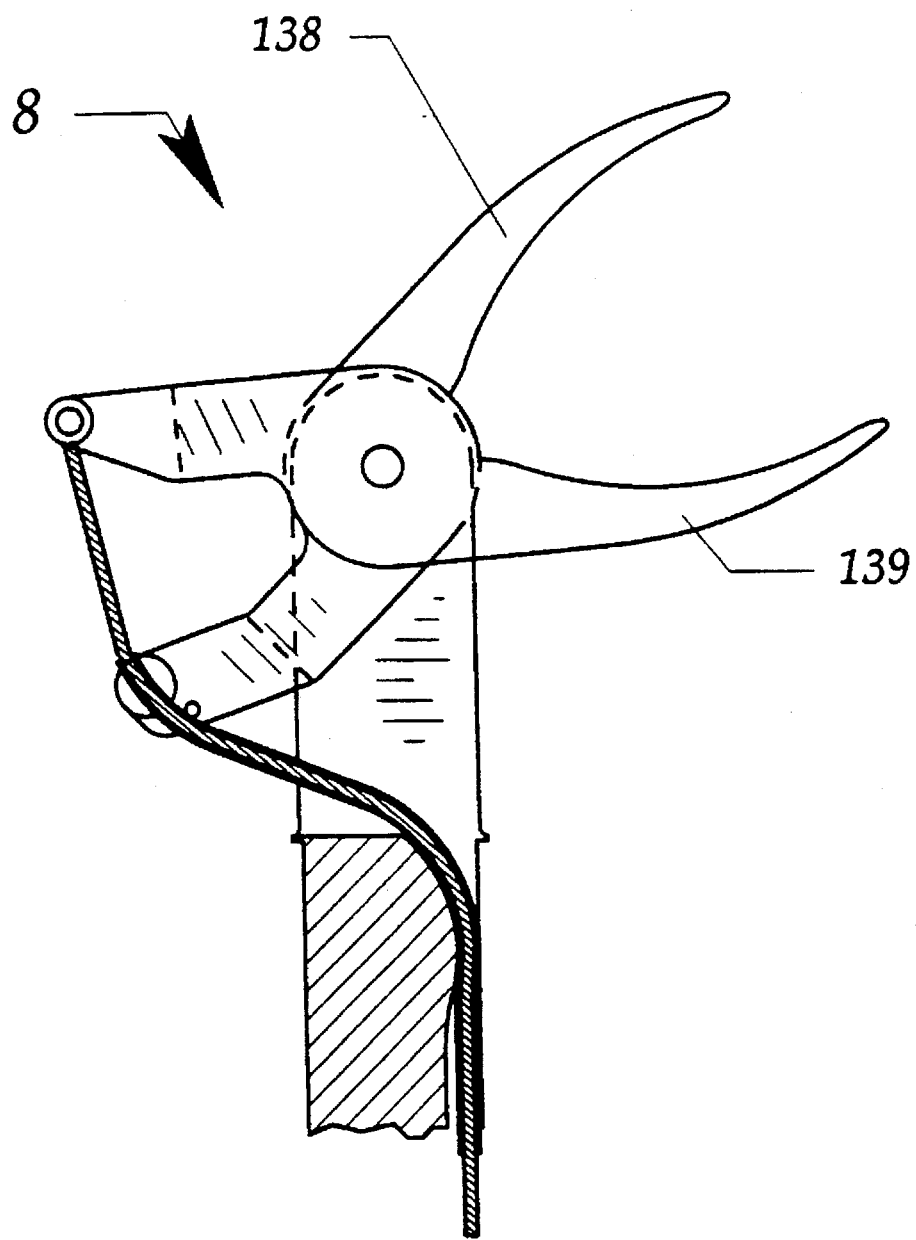
FIG. 19 is similar to FIG. 18, but depicting duckbill grasper jaws.

FIGS. 18 and 19 depict alternative embodiments of the present invention wherein the end effector 8, particularly the jaws or end effector pieces 138, 139 thereof, have a different shape. FIG. 18 shows a dissector end effector and FIG. 19 shows an atraumatic grasper. These are representative of the various kinds of end effector pieces which may be attached to the end effector, and their operational aspects are substantially similar to the end effector depicted in FIG. 2A.

Figure 20:
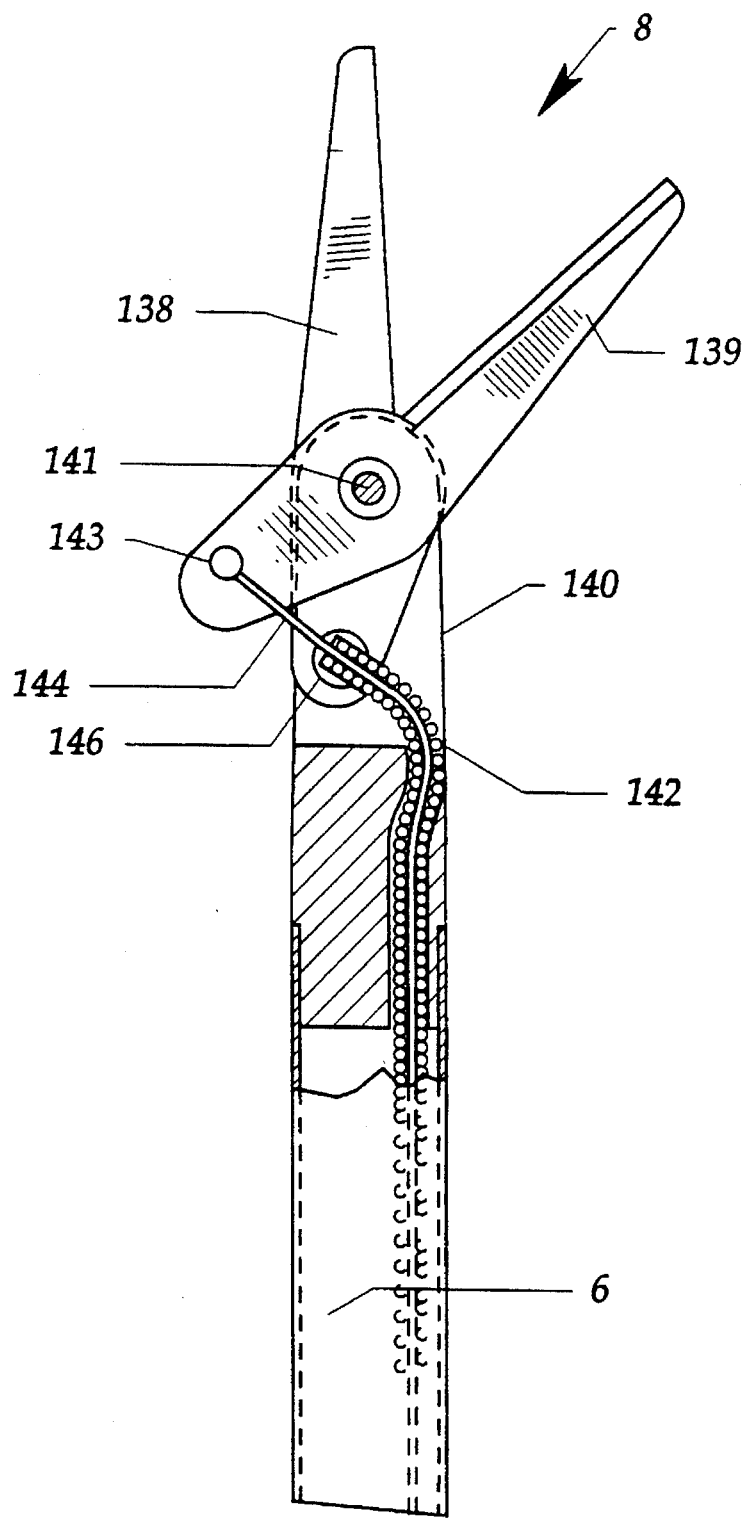
FIG. 20 is similar to FIGS. 2A–D, but depicting coiled sheath used as a control cable.

FIG. 20 shows an alternate embodiment of a control-cable technique for actuating the end effector 8. A flexible sheath 148 is used in place of the drawn nickel-titanium metal tube depicted in FIGS. 2A–D. A further refinement of this invention is the utilization of a slot, the bottom of which is curved with a defined radius in which the control cable sheath slides longitudinally. A further simplification of the invention, shown in FIG. 20, is elimination of the pivot 143 which attaches the control cable core 144 to end effector piece 139 and of the pivot 146 which attaches the sheath 148 to end effector piece 138. The wire core 144 may be fabricated as drawn metal wire, stranded wire or super-elastic alloy such as nickel-titanium. Suitable composite materials may be used as well. Similarly, the flexible sheath 148 of FIG. 20 may be formed by wound wire, polymeric material or a super-elastic metallic alloy.

Figure 21:
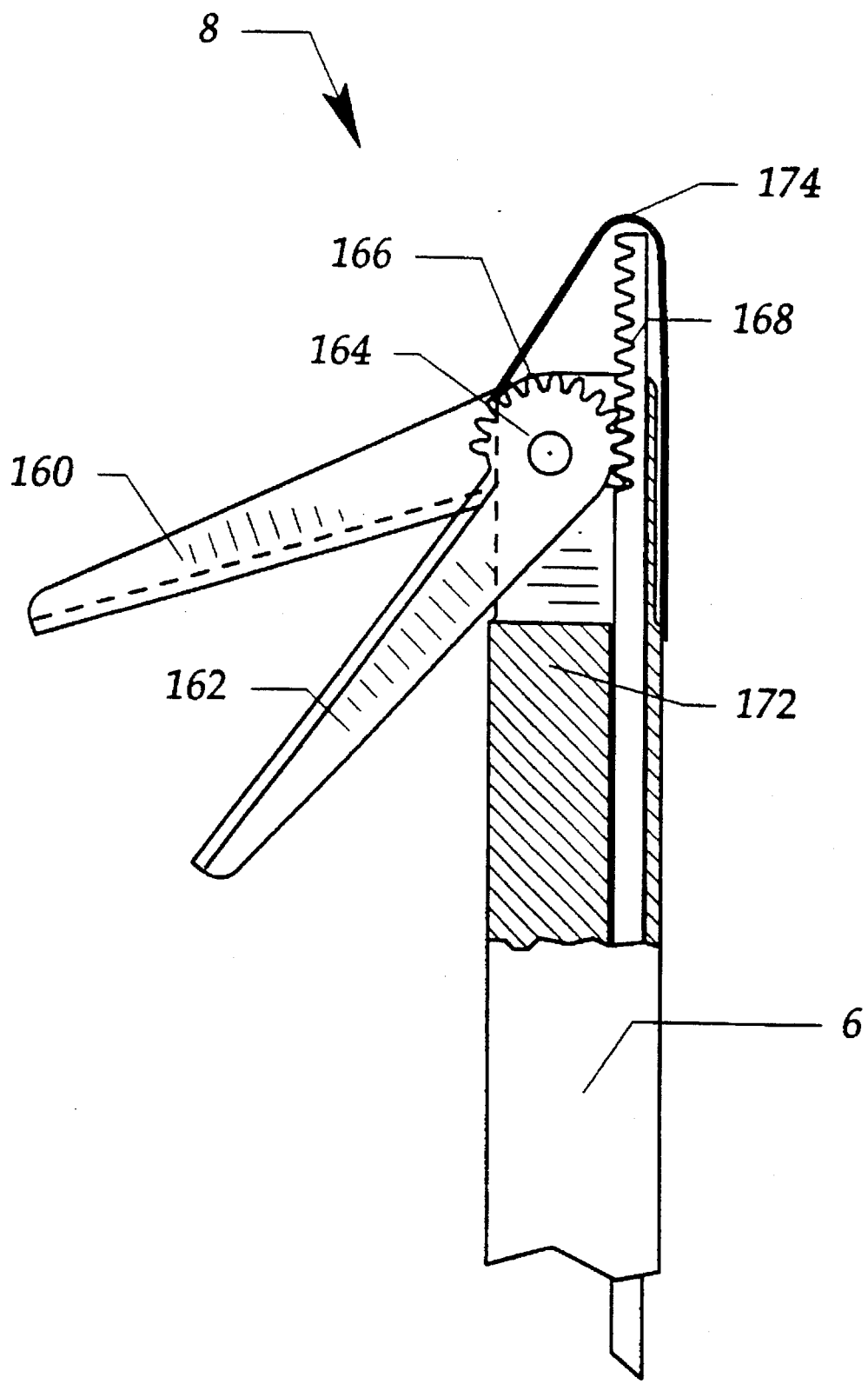
FIG. 21 is an elevational view of yet another embodiment of the present invention, wherein the end effector incorporates, partially in section, a pair of rack & pinion operating mechanisms.

FIGS. 21 and 22A–C illustrate another embodiment of the end effector mechanism utilizing a rack and pinion design. In FIG. 21, the end effector pieces 160,162 are pivotally attached to the fork 172 by pin 164 such that both end effector pieces may pivot freely. On the proximal end of each end effector piece 160, 162 are gear teeth 166 (shown at the proximal end of end effector piece 162). These gear teeth engage mating teeth of the rack 168, the tail of which is elongated to extend the length of the tubular barrel 6. End effector piece 160 has its own proximal gear teeth 166 and rack 170 (seen in FIG. 22C) which are independent of end effector piece 162 and rack 168. The racks are free to slide longitudinally and are held in engagement with the gears by part of the fork 172 which encloses the back of the rack. Pushing the rack 168 in the distal direction causes pivoting of the end effector piece 162 and pulling causes straightening. The rack is protected from fouling with tissue or injuring organs by an elastic sleeve 174 which stretches as the rack protrudes as shown in FIG. 21.

Figure 22D:
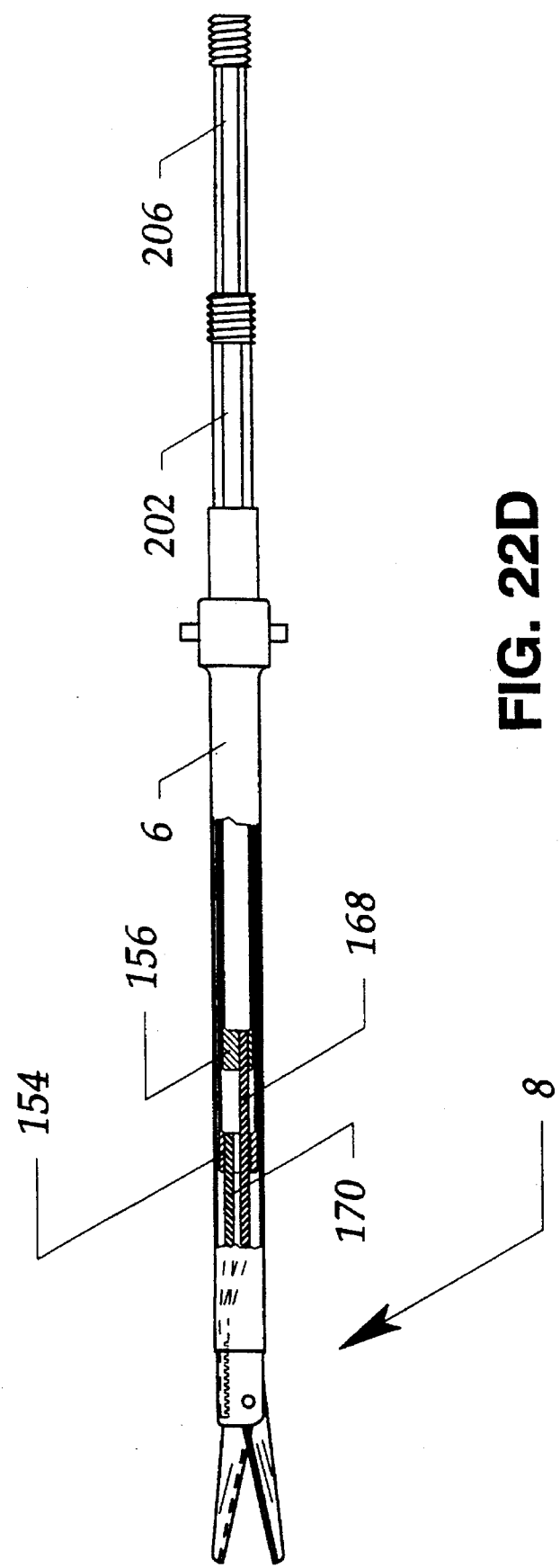
FIG. 22D is an elevational view similar to that of FIG. 3A and depicting another embodiment of the connection between an end effector and the linkage to the actuation mechanism of the present invention.

Referring to FIG. 22A, the end effector is pivoted straight, but the end effector pieces are open slightly. "Snipping" action is performed by pulling on rack 168 causing end effector piece 162 to pivot clockwise, and pushing on rack 170 (not shown) causing end effector piece 160 to pivot counterclockwise. FIG. 22B shows the two end effector pieces 160, 162 closed and straight. FIG. 22C is an end view of the end effector with end effector pieces 160, 162 pivoted 60° over and open slightly. In this view, the two racks, 168,170 can be seen clearly as can the two gears. FIG. 22D illustrates the coupling of the end effector with the first control rod 202 and second control rod 206 via attachment points 154 and 156.

Figure 23:
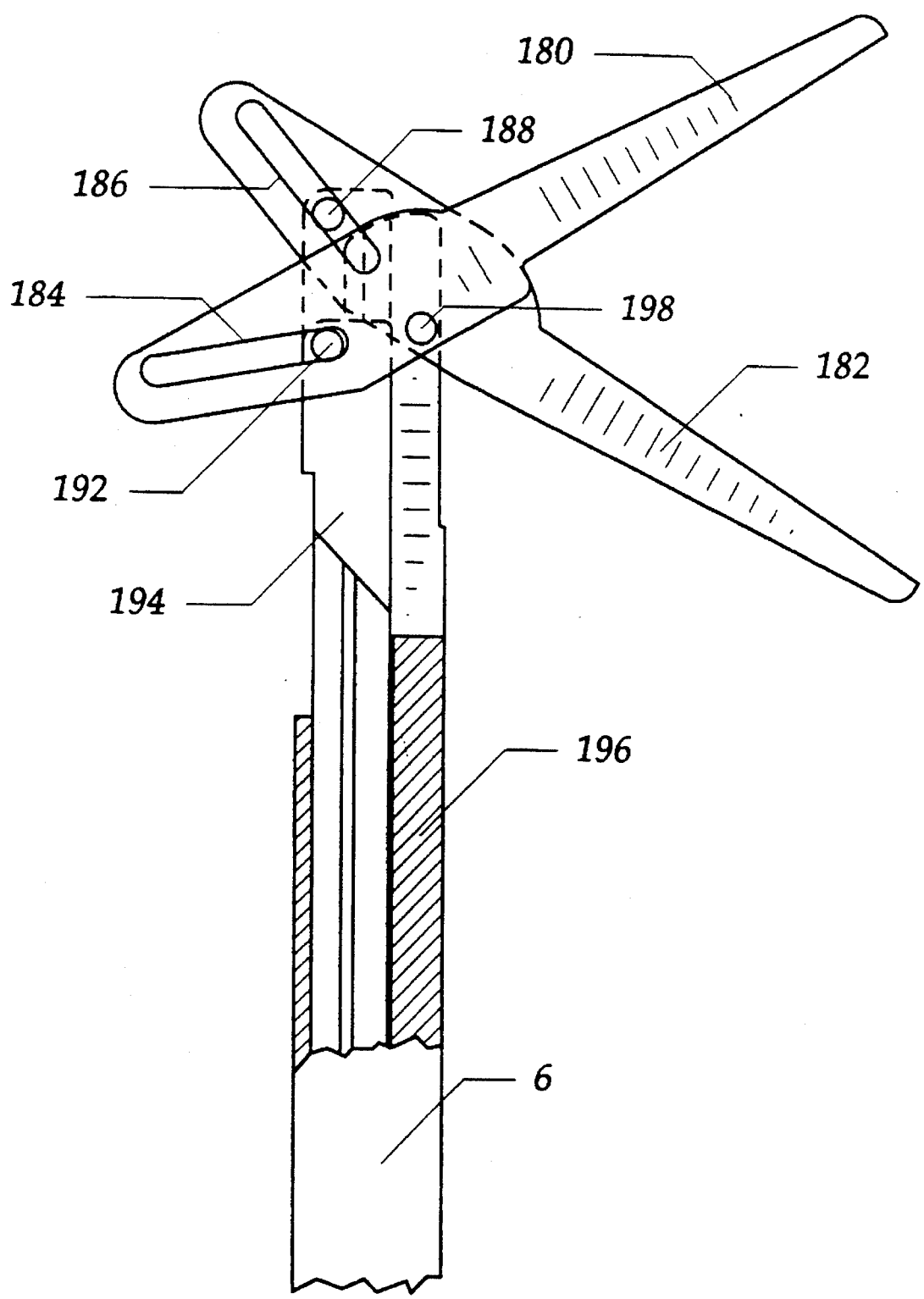
FIG. 23 is an elevational view, partially in section, of another embodiment of the present invention, wherein the end effector incorporates a pair of longitudinal sliding operational linkages.
Figures 24A, 24B:
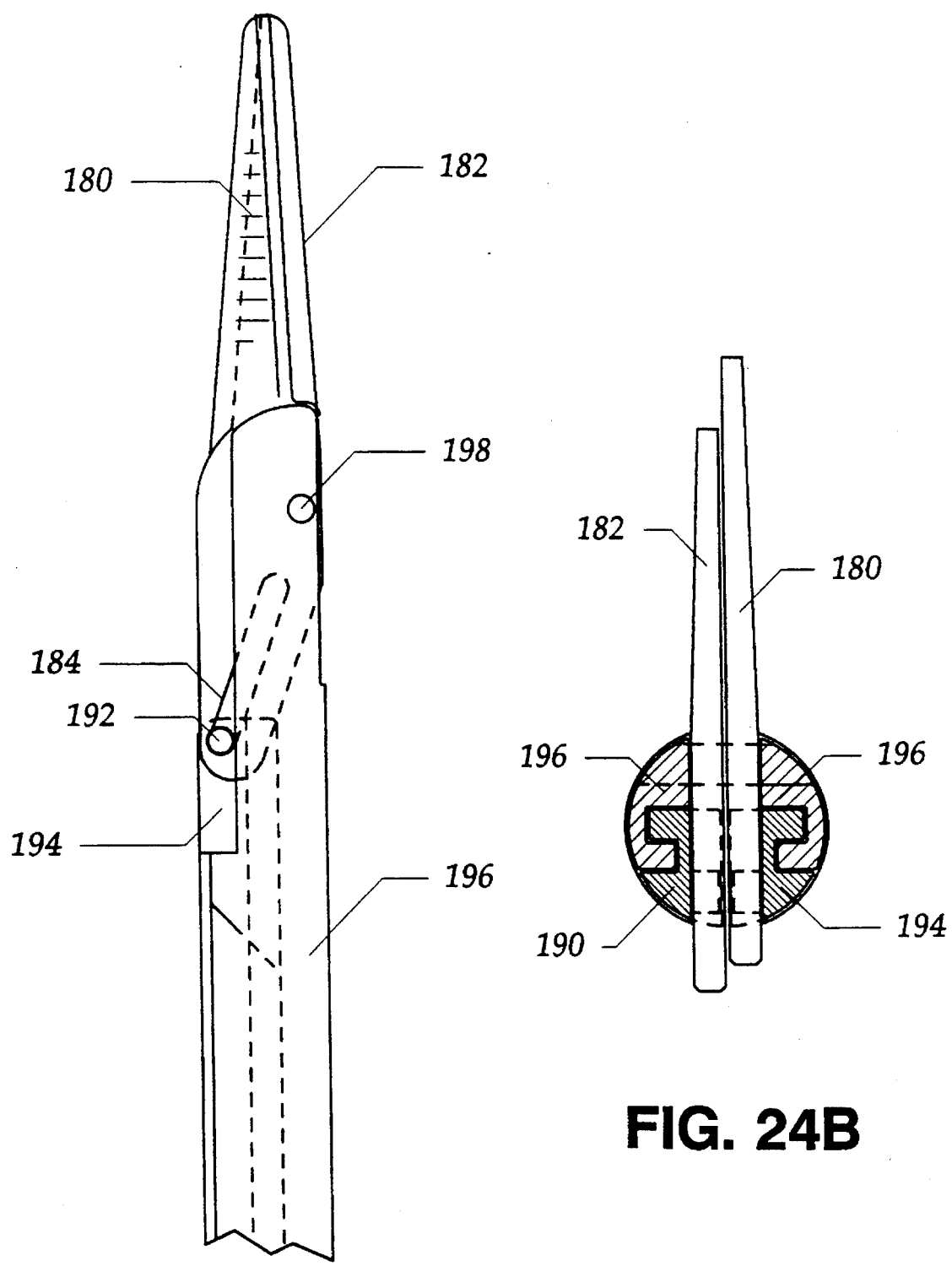
FIG. 24A is a view similar to that of FIG. 23, with the jaws aligned with the barrel and closed.
FIG. 24B is an end elevational view, partially in section, of the end effector shown in FIG. 23 with blades pivoted 45°.

FIGS. 23 and 24A–B depict yet another embodiment of the end effector. As in the previous descriptions, two end effector pieces 180, 182 are attached to fork 196 by way of a transverse pin 198 and pivot freely on the pin 198. The proximal end of each end effector piece has an elongated slot 184, 186 which engages two clevis pins 192, 188 attached to the distal end of two elongated control rods 190 (in FIG. 24B) and 194. The two linkage geometries are mirror images of one another. Referring to FIG. 23, moving linkage 194 in the proximal direction, causes pin 192 to slide down slot 184, causing end effector piece 180 to rotate counterclockwise. Pivoting the end effector pair back is accomplished by pushing both control rods 190 (see FIG. 24B) and 194 in the distal direction. "Snipping" action is achieved by pushing rod 194 while pulling on the opposite rod 190. Pushing the rods to the extreme in the distal direction causes the pins 188, 192 to progress up the slots toward the pivot pin, then down the slots away from the pin, causing the end effector to pivot back more than 120° from straight.

The end effector in the closed and straight position is shown in FIG. 24A. FIG. 24B is an end view of the barrel from the distal end of the instrument and depicts the end effector pieces opened slightly with respect to each other and pivoted about 20° with respect to the barrel. An important feature of this invention is the control rods 190 and 194 which interlock with the tubular barrel and fork 196, allowing longitudinal sliding yet resisting twisting which results from the off-center load imposed by the pins 192, 188 (shown in FIG. 23). An advantage of this embodiment is that because the control rods form a large part of the tubular cross section, they can be strong in both bending and stiff in axial loading. The result is that the mechanical linkages are very robust and resistant to flexing or springiness. Although movement of the rods and end effector pieces is quite non-linear with respect to angular position, this non-linearity is easily overcome by correcting linkages in the handle.

Figure 25:
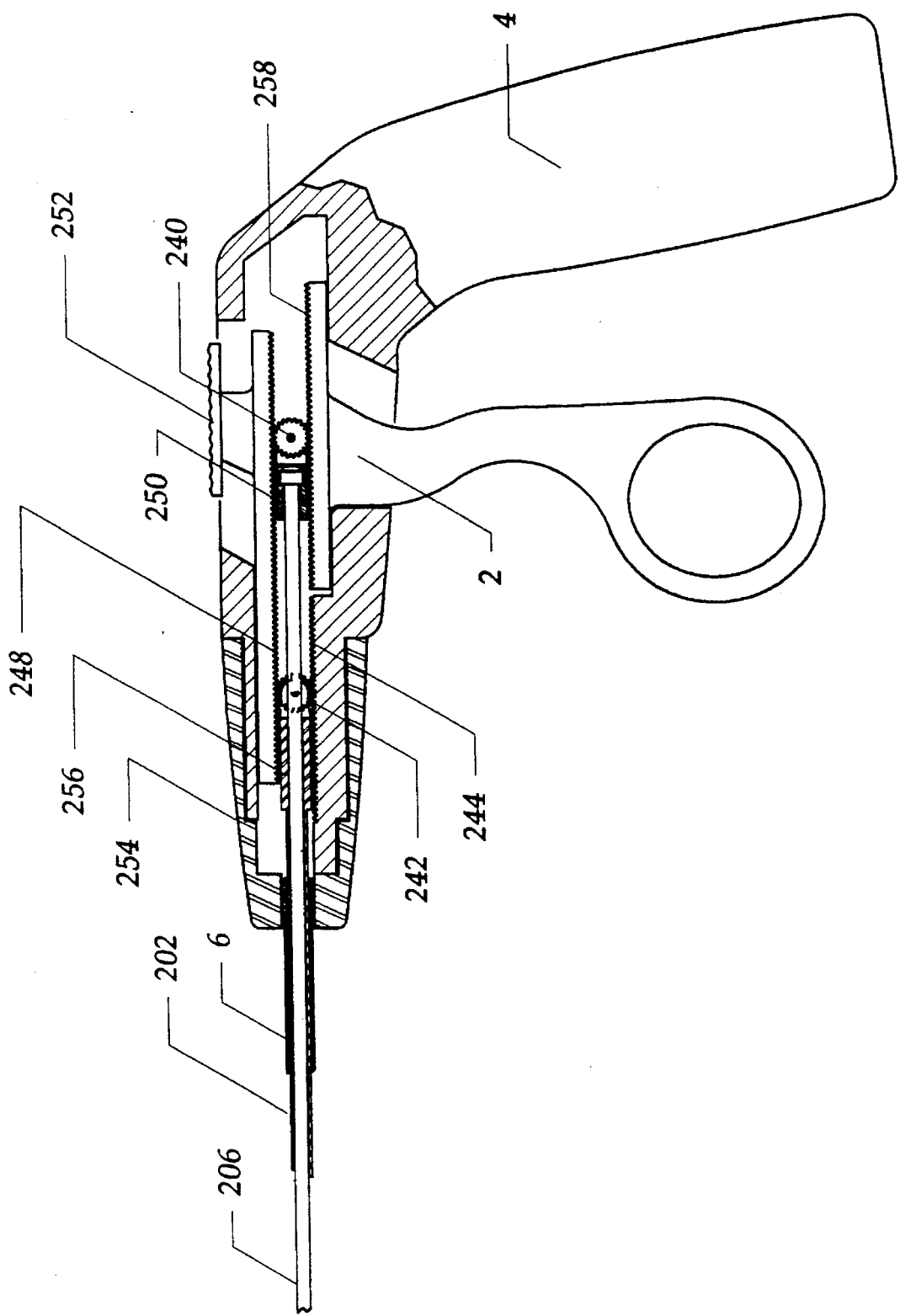
FIG. 25 is an elevational view, partially in section, of a manually operated handle for use with the present invention.

FIGS. 25 and 26A–B depict an embodiment of the present invention comprising an entirely manually operated handle attached to the end effector 8 (in FIG. 3) using a rack and pinion mechanism configured as a linear differential. This embodiment of the present invention uses a tubular barrel 6 and end effector assembly substantially similar to that shown in FIG. 3 and is removably attached to the handle 4. Instead of a removable barrel 6 utilizing standard screw threads, this embodiment could use either threads or bayonet fittings for all three releasable connections. Referring to FIG. 25, the tubular barrel 6 is connected directly to a rotatable knob 254 on the distal end of the handle 4. The inner control rod 206 is releasably coupled to the pinion yoke 250 on which pinion 240 is attached. The outer control rod 202 is also releasably connected to a second pinion yoke 256 on which pinion 242 is attached. Both pinions 240 and 242 are identical and are free to rotate. Rigidly fixed in the handle is a rack 244 which engages the pinion 242. On the opposite side of pinion 242, and also engaging it is a second rack 248 which is slidable in the handle and is moved with a slide lever 252. The second pinion 240 also engages the slidable rack 248, and on the opposite side of this pinion is a third rack 258 which is attached to the trigger 2 and is also slidable with respect to the handle. In FIG. 25, the two racks, 244 and 258 are shown end to end, but they could be placed side by side if shortening the handle is desirable.

FIG. 26A shows the function of pivoting the end effector. Sliding button 252 back in proximal direction as shown by the arrow causes pinions 240 and 242 to roll proximally, exactly the same amount, but half the distance the slide moves. This motion pulls control rods 202 and 206 back, causing the end effector to pivot back proportionally.

FIG. 26B shows the effect of closing the jaws by pulling the trigger. In this case, moving the trigger back causes the pinion 240 attached to control rod 206 to move in the proximal direction without moving pinion 242 or therefore rod 202.

Referring back to FIG. 25, rotation of knob 254 causes rotation of the entire end effector. In this way, the entire functionality of the instrument is manually controlled. The manual instrument potentially offers lower manufacturing costs and a similar degree of functionality and tactile feel to the user.

In the following, and in general reference to FIGS. 27–30, an alternate embodiment of the entire surgical instrument will be described. This alternate instrument design includes an end effector 8, a barrel 12 and a handle 10, each of which will be described in detail below.

Figure 27A:
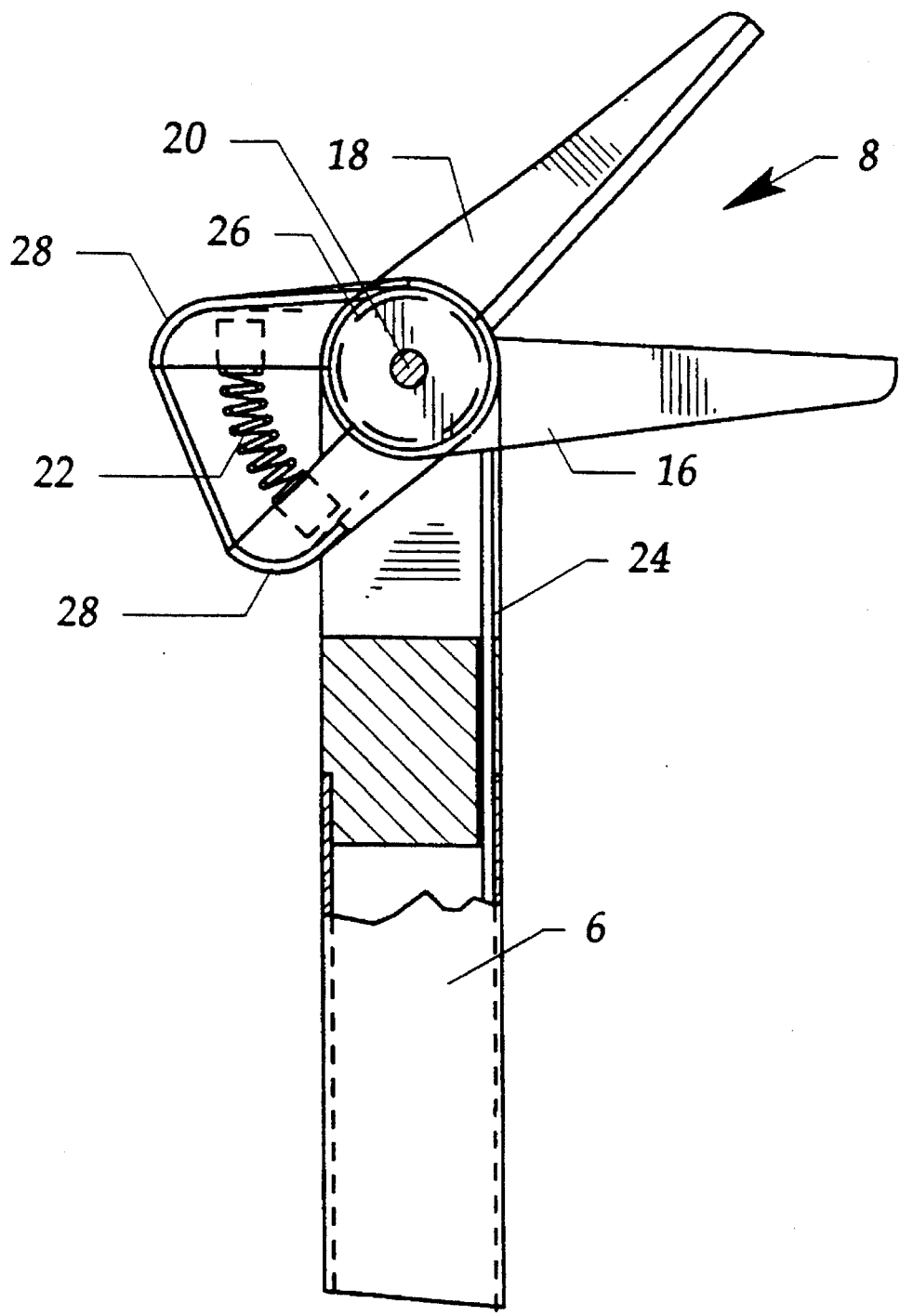
FIG. 27A is an elevational view of another embodiment of an end effector of the present invention.

FIGS. 27A–C show enlarged views of the scissor-like end effector 8 of the alternate instrument design. In FIG. 27A the scissor end effector 8 is open and rotated 45° relative to the barrel 6. The scissor-like working end effector tip 8 comprises two end effector pieces (blades) 16 and 18 pivotally attached to the barrel tube 6 by a pin 20. The end effector pieces 16, 18, as a pair, are rotatable 360° around the pin 20, and each end effector piece 16, 18 is rotatable 45° relative to the other end effector piece from a fully closed position (FIG. 27C) to a fully open position (FIG. 27A). The end effector pieces 16, 18, as shown in FIG. 27C, are parallel to one another, each having an adjacent flat face, which, when the tip 8 is closed, creates a shearing edge. The two end effector pieces 16, 18 are biased toward the open position by a compression spring 22 (or torsion springs, not depicted). Two substantially identical control cords 24, 30, only one of which is shown in FIG. 27A–C for clarity, are provided for closing the end effector pieces 16, 18 relative to one another and for pivoting the end effector pieces 16, 18 relative to the tubular barrel 6. The control cord 24 extends along the longitudinal axis (A in FIG. 27B) of the barrel 6, over a pulley 26, which is free to rotate independently around pin 20, and along the back of the butt or proximal end 28 of the end effector pieces 16, 18. A polished radius is machined in the proximal end 28 of both end effector pieces 16, 18, for receiving the cord 24, which then spans the distance to the opposite end effector piece 18 where it wraps around a similar radius to the back of end effector piece 16, where it is attached. The second cord 30 (shown in FIGS. 28A–D) is similarly disposed, but, at the end effector, in a direction opposite to cord 24. Thus, cord 30 extends along the longitudinal axis of barrel tube 6 over a second pulley (not shown, but identical to pulley 26), which is free to rotate independently around pin 20, and along the back of the proximal end of the end effector piece 18. Cord 30 is received by a polished radius machined in the proximal end of end effector piece 18, spans the distance to the opposite end effector piece 16, where it wraps around a radius, is terminated and fixed in place.

FIG. 27B is a cross-sectional view of the scissor-like end effector 8 wherein the end effector pieces 16, 18 are closed and aligned with the longitudinal axis (A) of the barrel tube 6. FIG. 27B and 27C illustrate that when the working tip 8 is closed, its diameter is no greater than the diameter of the barrel tube 6. In a preferred embodiment, that diameter is such that the instrument may readily pass through a 5 mm trocar sleeve or a laparoscopic port of only 5 mm (sleeve and port not shown). Thus, versatility and 3-dimensional control of the end effector 8 of the invention is achieved without sacrificing the small diameter required for minimally invasive surgical procedures.

FIGS. 28A–D depict the 3-dimensional movement available at the working end effector scissor-like tip 8. Each of the two cords 24, 30 extends parallel to the axis of the barrel 6 (line A) and is attached to one of two nuts 32, 34. The nuts 32, 34 are constrained by appropriate means, such as a key or spline, to prevent them from rotating in the barrel tube 6, but to allow their axial movement generally along the axis of the barrel 6. Each cord 24, 30 is attached to its respective nut 32, 34. Thus, cord 30 is directly connected to nut 34, and cord 24 passes through a hole in nut 34 and is connected to nut 32. A shaft 36 extends generally coaxially relative to barrel tube 6 and is threaded at its distal end. It is threaded with a standard (right hand) thread along a length 38 which exceeds the total desired travel of the cords 24, 30 as the end effector 8 is rotated from one extreme to the other. Equal lengths 38 and 40 of the shaft 36 are threaded in opposite directions. Rotation of shaft 36 in one direction causes nuts 32, 34 to advance together, and rotation in the other, opposite direction causes nuts 32, 34 to drive apart.

FIG. 28B shows the result of retracting the shaft 30 in the proximal direction (i.e., along arrow B toward the handle 4), pulling nuts 32, 34 and, therefore, cords 24, 30 simultaneously. The end effector pieces 16, 18 close relative to one another, but without rotation relative to the barrel tube 6. This is an important aspect of the invention because it allows the user to maintain the working end effector tip 8 at a constant angle relative to the axis of the tubular barrel 6, while still achieving activation of the end effector 8. When both end effector pieces 16, 18 are closed and straight, as shown in FIG. 28B, the profile of the entire device is within the profile required for passage through a relatively small laparoscopic surgical port or to access a tight area.

FIG. 28C shows the pivoting action (arrow C) of the end effector 8 as a result of rotation of shaft 36 inside the barrel tube 6. Rotating shaft 36 relative to barrel tube 6 causes nuts 32, 34 to drive together, pulling on cord 30 while releasing cord 24 exactly the same amount. This results in pivoting the end effector 8 in the plane of the axis of the barrel tube 6. It can also be seen that the pivoting of the end effector 8 is independent of the degree of closure of end effector pieces 16, 18. That is, the pivoting of end effector pieces 16, 18 is independent of how far shaft 36 is retracted in the proximal direction. This is useful because it allows a surgeon to control both closing and pivoting of end effector pieces 16, 18 independently, which allows him to selectively separate or cut tissue.

FIG. 28D shows the rotational action of the end effector 8 as a result of simultaneously rotating both the shaft 36 and barrel 6 (arrows D). When both shaft 36 and barrel 6 are rotated in the same direction at the same rate, the nuts 32, 34 do not advance relative to the barrel 6 and no pivoting of the end effector 8 occurs. The net result is the simultaneous rotation of the barrel 6 and end effector 8 (arrow D). It can also be seen that closing of the end effector pieces 16, 18 is independent of the degree of rotation of the barrel 6 and end effector 8. This mechanism also has the advantage that the system has no orientation preference and the control cords 24, 30 cannot tangle or cross. This advantage is significant for interchangeable end effectors (including the detachable barrel 6 and selected end effector 8), because reattachment (i.e., plugging a selected end effector or barrel 6 into the handle 4) does not require special orientation or locating of engagement structure.

Figure 29A:
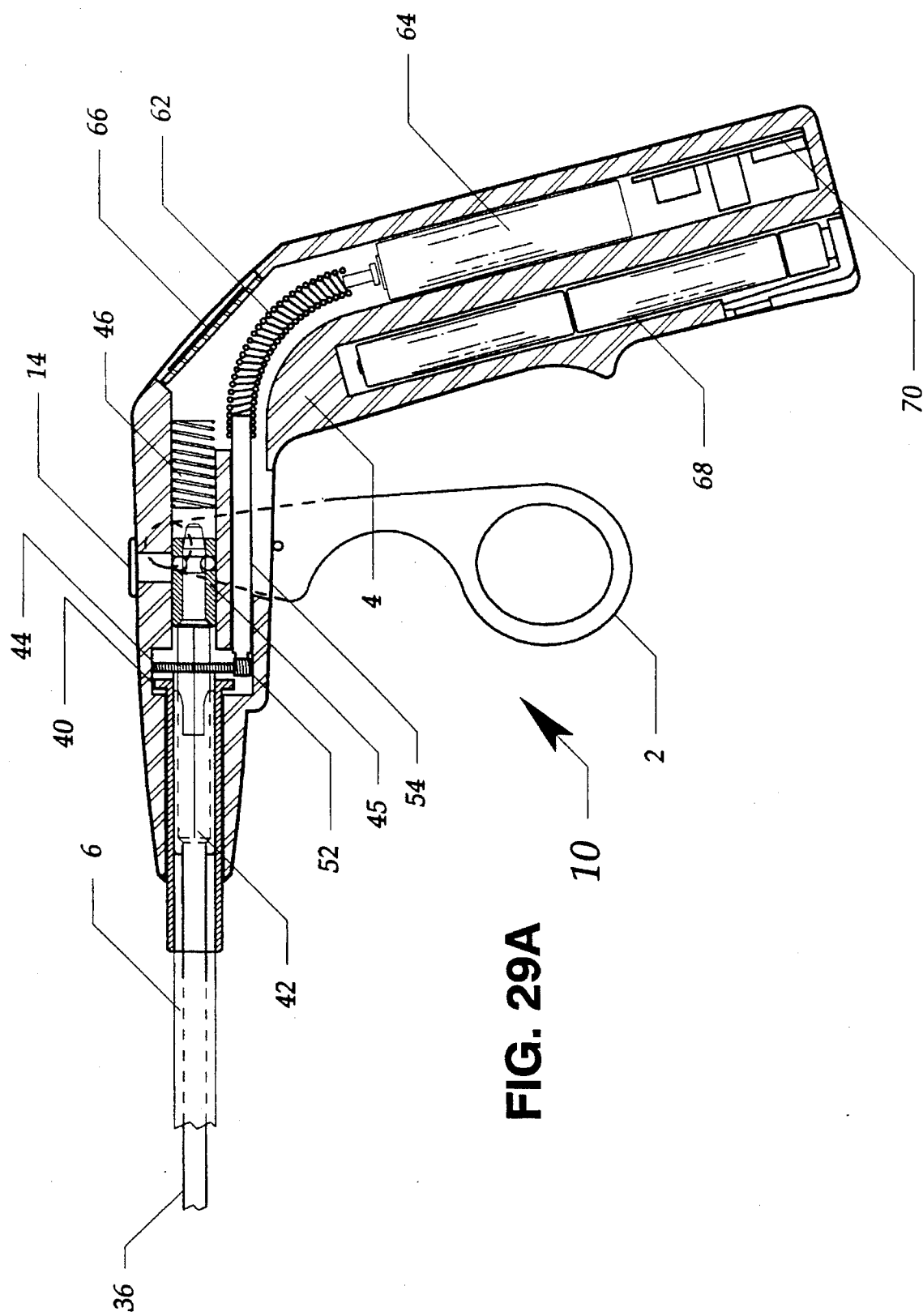
FIG. 29A is an elevational view, partially in section, depicting another embodiment of the handle for use with the present invention, with the barrel rotation mechanism removed for clarity.

Referring to FIG. 29A, details of the internal configuration of the handle 4 are illustrated for the alternate instrument design. This is an embodiment of the present invention wherein closing the end effector is performed manually by retraction of a finger trigger. The barrel tube 6, which may be an integral part of an end effector assembly, is inserted into a receiving hole in handle 4, and is restrained. The proximal end of barrel tube 6 is forked, or fitted with an appropriate connection mechanism, such as a spline, resulting in positive torsional engagement with gear 40. Gear 40 provides for positive rotational driving of the tubular barrel 6 around its longitudinal axis. The proximal end 42 of shaft 36 is adapted (e.g., square or splined) to engage with gear 44, but slides through gear 40 to allow positive rotational driving of shaft 36, independently of gear 40 and the barrel 6. The shaft 36 is biased in the distal direction relative to the barrel 6. The shaft 36 extends through a collar 45 and is positively connected with it, whereby pulling of collar 45 in the proximal direction moves the shaft 36 in the like direction. The collar 45 is biased in the distal direction by a spring 46 and is connected to trigger 2 by a fork assembly (not shown) which allows free rotation of the shaft 36 and spline 42, but also enables the retraction of shaft 36. Pulling the trigger 2 causes closing of the end effector pieces 16, 18 (see FIG. 27A), and the amount of closure is directly proportional to the travel of the trigger 2.

Figure 29B:
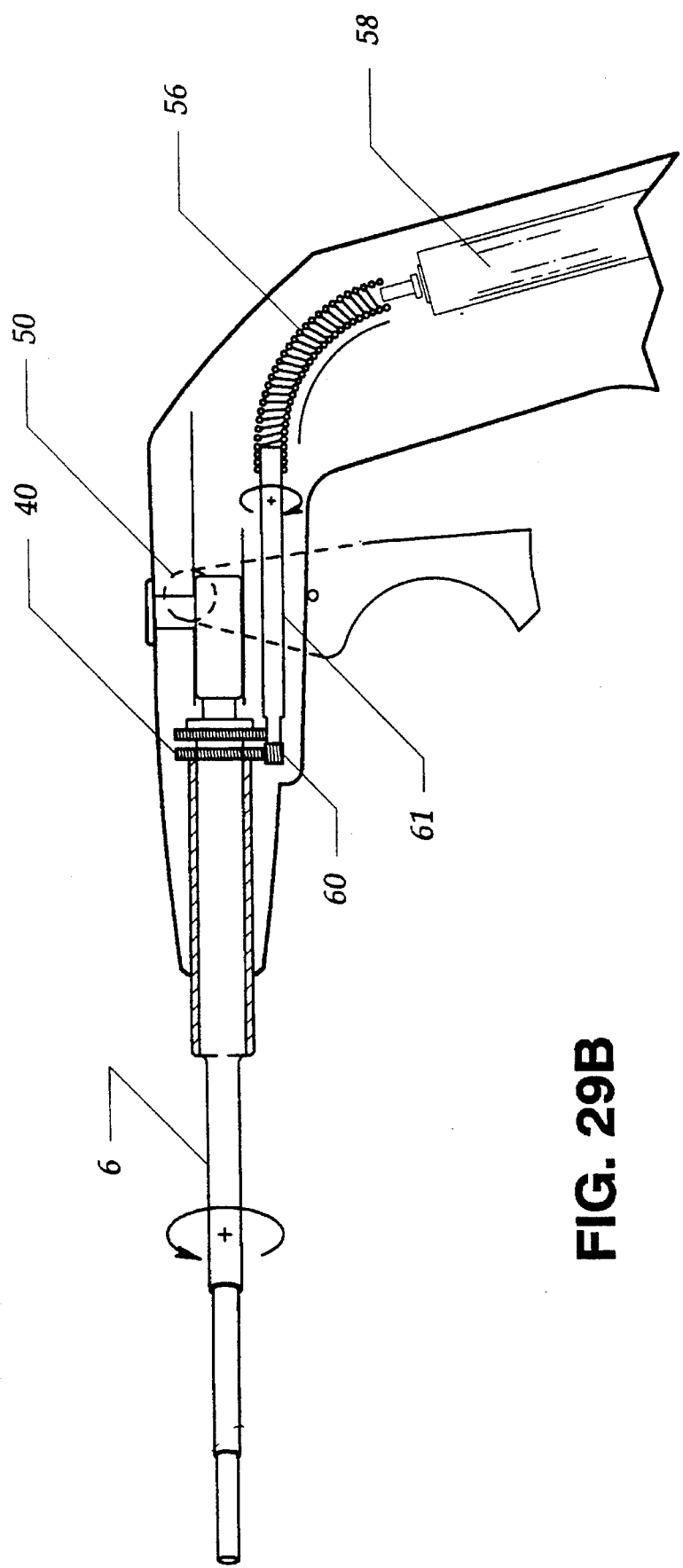
FIG. 29B is an elevational view similar to FIG. 29A showing rotation of the end effector.

With reference to FIG. 29B, gear 40 meshes with pinion 60 on a separate shaft 61, driven through its own right angle drive 56 and gearmotor 58. In this way, gearmotor 58 rotates the tubular barrel 6 of the end effector directly. Referring to FIG. 29A, gear 44 meshes with pinion 52 on shaft 54, driven through gearbox and motor 64. The two discrete motor and gear assemblies allow direct control of each independent axis of movement of the end effector 8. The two are mounted side-by-side in the handle. The motors 58, 64 are controlled by a multi-positional joystick-type or pushbutton control switch 66 mounted on the handle 4 within comfortable reach of a user's thumb. Power for the motors 58, 64 is supplied by an integral, rechargeable or removable battery 68. Position of the end effector is controlled by commercially available, microprocessor-based control electronics 70, whose function and operation is described hereinabove in reference to FIGS. 7–17.

Figure 30A:
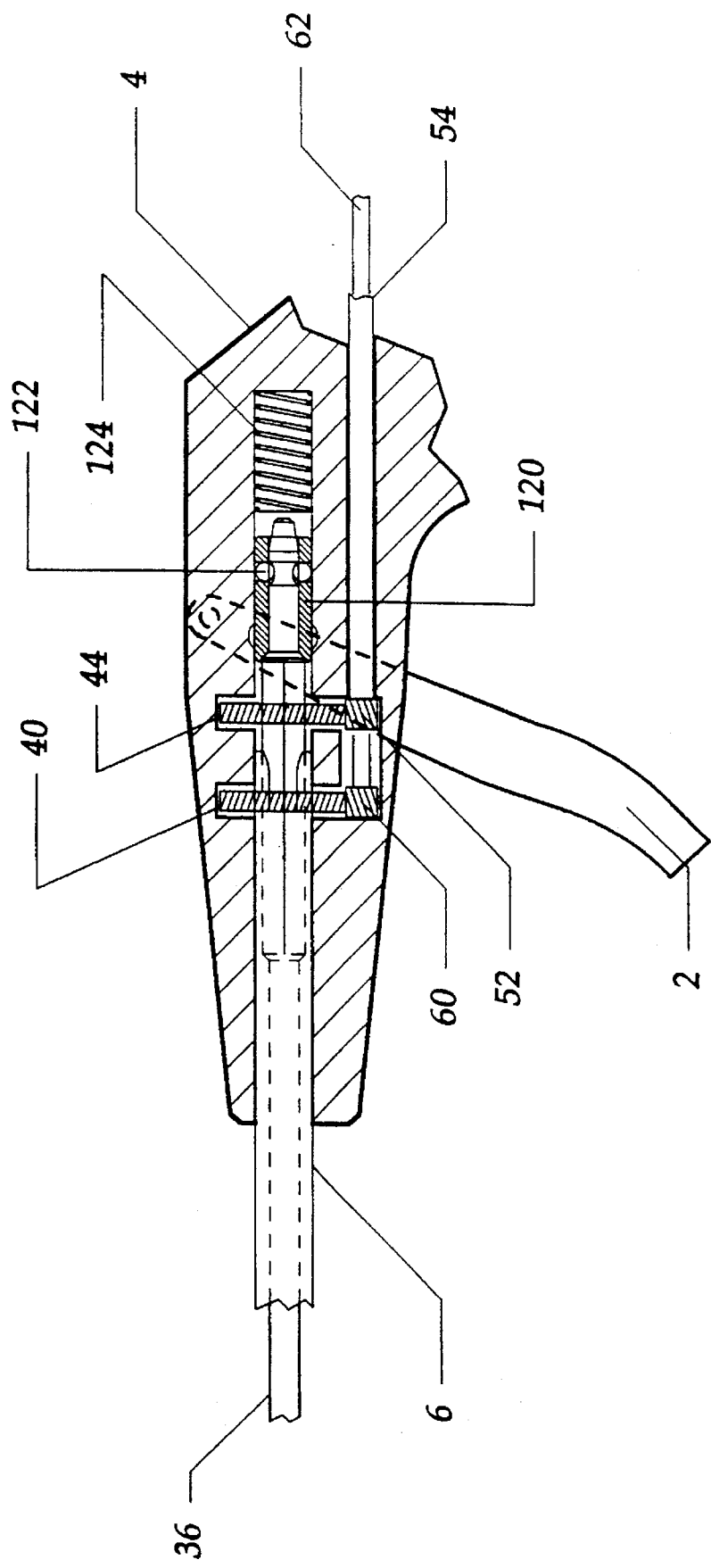
FIG. 30A is a fragmentary sectional view of a modified handle embodiment showing a coupling mechanism for attaching the end effector and barrel to the handle.
Figure 30B:
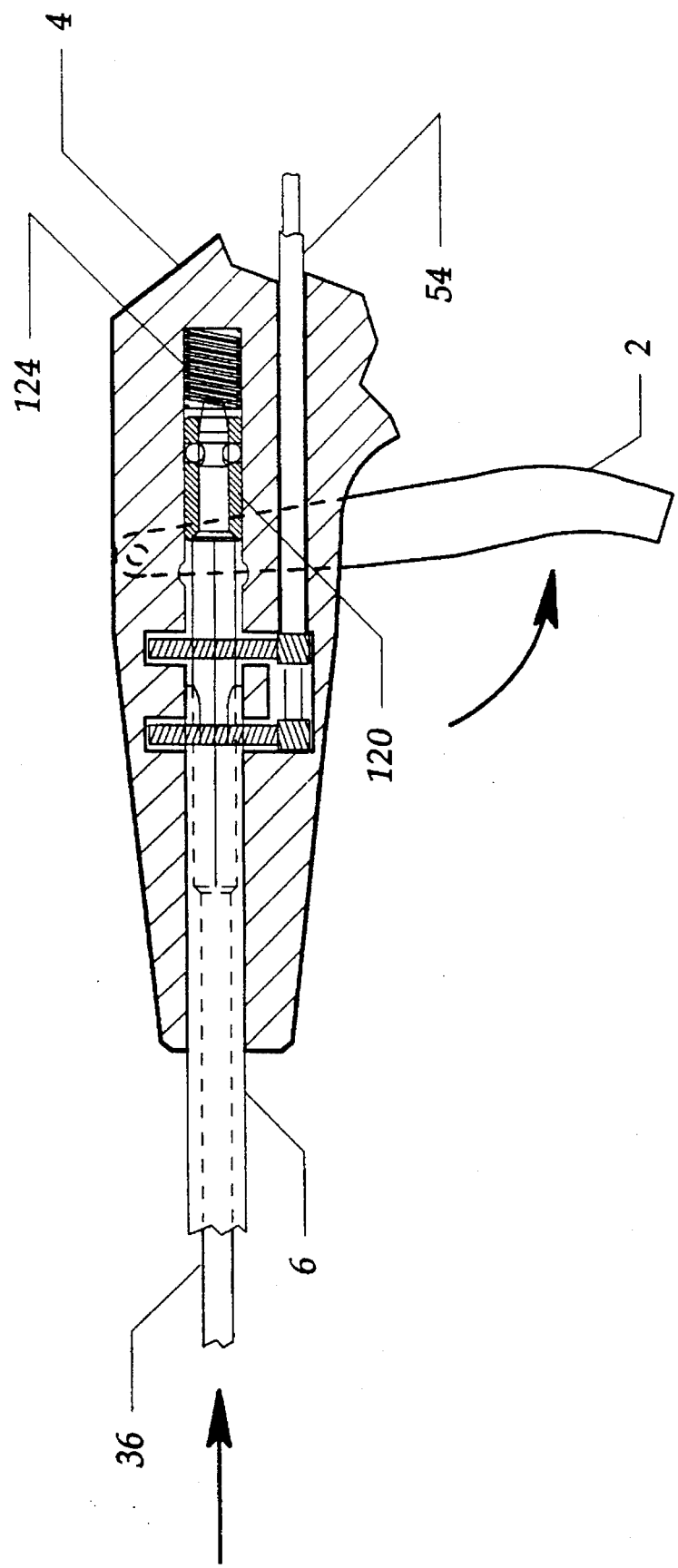
FIG. 30B is a sectional view of the embodiment depicted in FIG. 30A, with the operating trigger in another position.
Figure 30C:
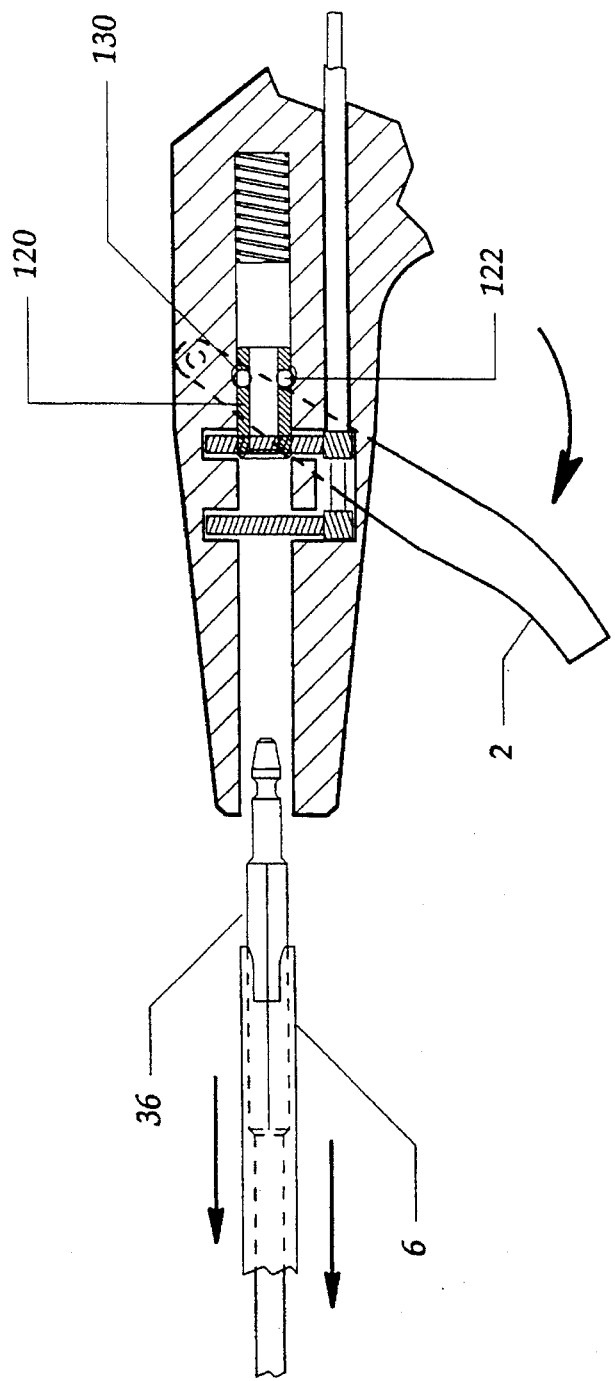
FIG. 30C is a sectional view of the handle depicted in FIGS. 30A and 30B, with the operating trigger in a third position.
Figure 30D:
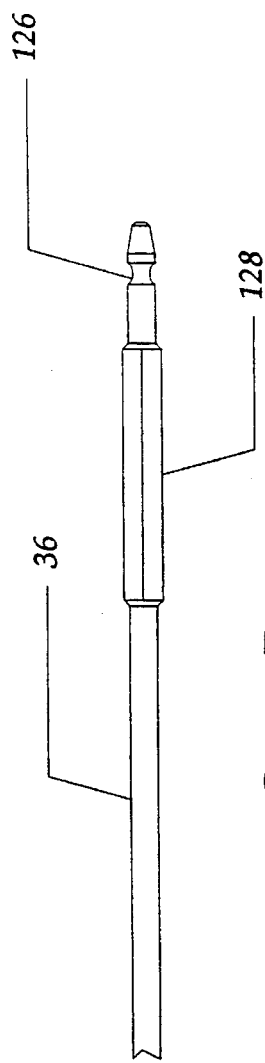
FIG. 30D is an elevational view of a portion of the operating shaft of the present invention.

Referring to FIGS. 30A–D, the mechanism for attaching and detaching the barrel 6 from the handle 4 is depicted for the alternate instrument design. Specifically, in FIG., 30A the shaft 36 is retained in a generally cylindrical locking collar 120 slidably mounted in the handle 4. The collar 120 contains, operably and slidably, a spring 124, a set of detent balls 122 captured in a holes in the collar and a trigger pin (not shown). The shaft 36 and barrel 6 are held in the handle 4 by the balls 122 which releasably engage in a detent ring 126 adjacent to the proximal end of the shaft 36 (see FIG. 30D, depicting details of the shaft 36, including the splined or square portion thereof), thereby locking the shaft 36 to the collar 120 axially, while allowing the shaft 36 to rotate freely. Referring to FIG. 30B, retraction of the shaft 36, and the resultant closing of the end effector tip 8, is accomplished by moving the trigger 2 in the proximal direction, retracting the collar 120, operably coupled to the trigger by a clevis pin (not shown).

With reference to FIG. 30C, moving the trigger 2 in the opposite, distal direction, beyond its normal range of travel for opening and closing the end-effector tip 8, enables the barrel and end effector assembly to be removed from the handle 4. This movement of the trigger 2 slides the collar 120 against a shoulder on the shaft 36 (FIG. 30D), pushing the barrel 6 and shaft 36 in the distal direction, out of the handle 4. When the trigger 2 is moved to a fully unlocked or release position, the collar 120 is moved in the distal direction until the balls 122 are released radially outwardly into a ball receiving detent ring 130 (best seen in FIG. 30C) on the inside of the bore centered in the handle, freeing the shaft 36, together with the barrel 6 and end effector 8, from the handle 4. Replacing the same or a different end effector assembly (referring to barrel 6 and an integral tip 8) is accomplished by pushing the new assembly into the handle 4 in the proximal direction.

Referring back to FIG. 29A, an alternative detent mechanism may be used for securing the barrel tube 6 and the shaft 36 it carries to handle 4. By depressing the button 14, a sliding dog (not shown) is disengaged, allowing the barrel tube 6 and shaft 36 to be removed from handle 4 similar to the action shown in FIGS. 30C. In this manner, multiple tip assemblies (including the barrel 6 and a selected end effector) may be used with a single handle 4 and be safely and operably secured to the handle 4.

FIGS. 31A–C and 32A–B show alternative embodiments of the scissor-like end effector tip 8 depicted in FIG. 27A–C.

FIG. 31A shows an end effector 9 similar to that shown in FIG. 27A, wherein two end effector pieces 80, 82 are operated or closed by a pair of cords (not shown) in a manner identical to that described above with reference to FIG. 27A. The principal difference in the two designs is that, as shown in FIG. 31A, another pair of cords 84, 86 (only cord 84 is shown) is used to open the end effector pieces 80, 82 instead of relying on a spring 22 to urge them apart, i.e., open, and end effector pieces 80, 82 have levers 81, 83. Cord 84 extends axially down barrel tube 6, wraps around pulley 26, extends along the backside of the lever on end effector piece 82 and connects to the lever on end effector piece 80. Pulling on cord 84 pulls the levers together, opening the end effector pieces 80, 82. One advantage is that the cords 84, 86 (not shown) enable positive opening of the end effector pieces 80, 82, whereby opening may be accomplished with greater force than is possible with the spring alone.

Figure 32C:
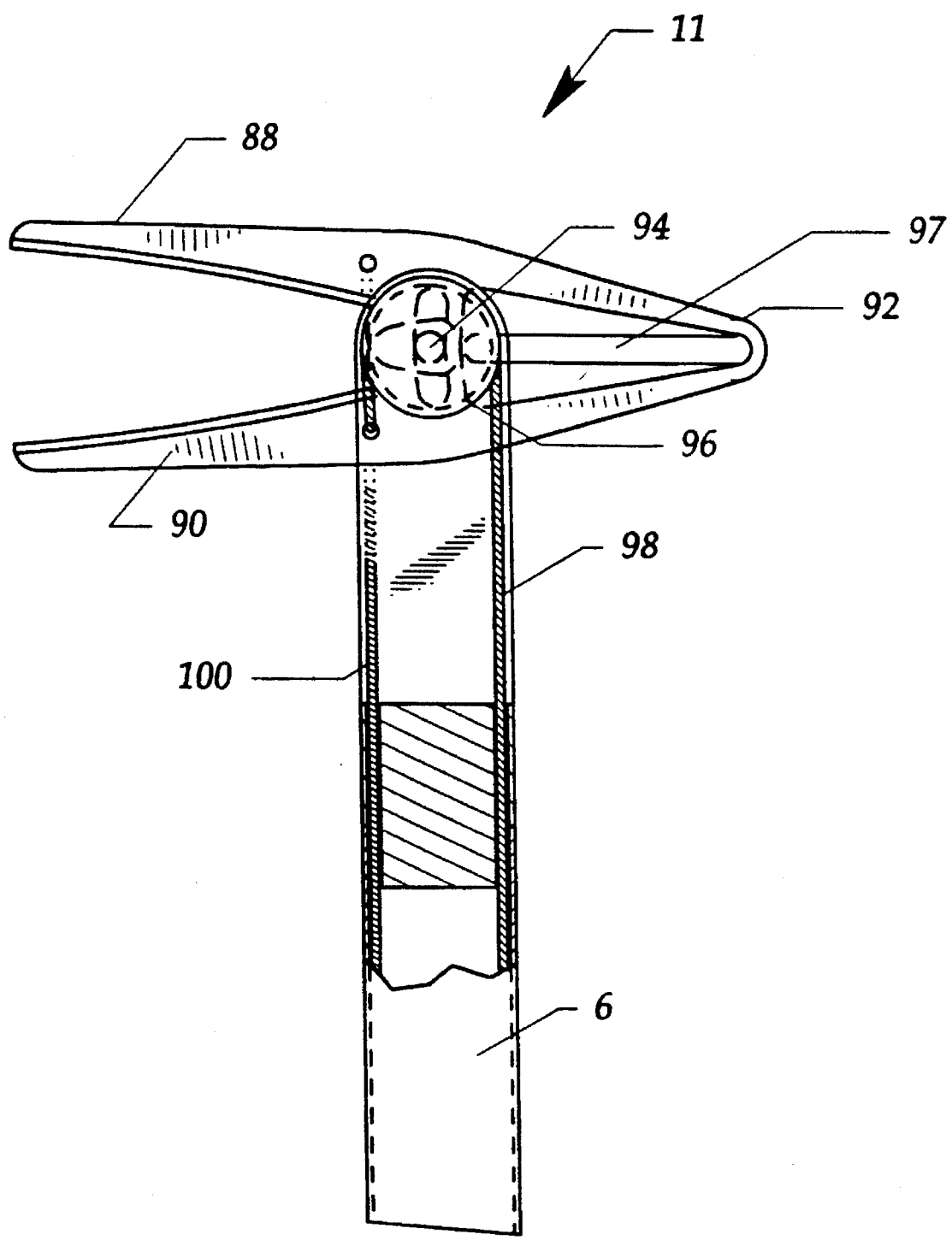
FIG. 32C is a view similar to that of FIG. 32A, depicting the pivoting movement of the end effector.

FIGS. 32A–C shows an alternative scissor-like tip embodiment 11 which offers the advantages similar to those provided by the scissor-like design shown in FIG. 27A–C, however with fewer parts. FIG. 32A shows two end effector pieces 88, 90 which are ground to shear against one another. They are biased into the open position (FIG. 32A) by an integral spring 92 which connects the end effector pieces 88, 90 together. Each of the end effector pieces 88, 90 has a curved slot 93 through which pin 94 passes. The end effector pieces or jaws 88, 90 are located by pulley 96 and its "tail" 97 which protrudes in the proximal direction into the bend of the spring 92. The pulley 96 and "tail" 97 rotate together around pin 94 fixed in the end of the tubular barrel 6. This rotation causes pivoting of the end effector piece assembly around pin 94. Cord 98 wraps around the pulley 96 on one side of the pair of end effector pieces 88, 90 and attaches to end effector piece 88 on the opposite side. Similarly, another cord 100 runs in the opposite direction around the other pulley (96 in FIG. 32B) and attaches to the opposite end effector piece 90. Just as illustrated in FIG. 27, pulling on one cord while releasing the other causes rotation of the end effector pieces 88, 90 in that direction. FIG. 32C shows the end effector pieces 88, 90 rotated 90° (cord 100, the far cord, is hidden where it attaches to end effector piece 88). Pulling on both cords simultaneously causes closure of the end effector pieces 88, 90 and generates a cutting or shearing action. The advantage of this design is that the spring 92 biasing the end effector pieces 88, 90 open is an integral pad of the end effector pieces 88, 90 and, thus, there are only two moving pads (excluding the cords 98, 100) in this embodiment of the end effector 11.

Another variation of the present handle and operating mechanism embodiment of the present invention includes another servo motor which automatically opens and closes the end effector tip 8, as well as providing automatic powered functioning such as vibration. The motor may be controlled by the microprocessor 70 described above. Referring back to FIG. 30A, the third motor, gearbox, and gearing mechanism engage the collar 120 which is threaded on its outer, generally cylindrical surface and meshes with a complementary threaded gear (not shown). The gear is driven by a pinion operably coupled to an augmented motor and gearbox drive assembly. Driving the gear in one direction, causes the retraction of the collar 120 and shaft 36, closing the end effector tip 8. Driving the gear in the opposite direction moves the collar 120 in the distal direction, pushing the shaft 36 (and the barrel 6) out of the handle 4. Disengagement is accomplished as before, i.e., when the balls 122 are released into the expanded ring in the inside diameter of the collar 120.

Although the trigger 2 is substantially the same as that depicted in FIG. 29, in this embodiment it is basically a multi-position switch biased in the distal direction. At least five positions are provided for controlling the motor. Each position is indexed, providing tactical or audible feedback to the user. One position, a fully released or open position (position 1), corresponds to a control signal sent to the microprocessor to move the motor at high speed until the end effector tip 8 is fully open and held open. Another position (position 5), the trigger's proximal position, provides a signal to the microprocessor to operate the motor to close the end effector 8 at high speed and hold it closed. Intermediate positions at 25%, 50% and 75% (positions 2, 3 and 4, respectively) of trigger travel correspond to slow opening of the end effector, motor disconnect to fix the end effector in its current position and slow closure of the end effector, respectively. Additionally, the trigger may be adapted to be movable vertically to provide a "lock-out" feature, immobilizing the end effector 8 in any position.

When the trigger 2 is moved off the neutral position, i.e., either pulled or released, the microprocessor may be used to set the voltage to maintain a set speed. If the trigger is held as outlined above, for example in the 75% pulled position, the motor continues to close the end effector until it begins to slow down. At this point the microprocessor 70 automatically increases the voltage and thereby current, to maintain the desired speed. This continues until the motor is stalled at full current, translating to maximum closing force at the end effector. The microprocessor maintains full current on the motor until the motor is driven to the position corresponding to the end effector fully closed. At this point power is removed from the motor. This feature minimizes heat build up in the motor and current drain on the battery, prolonging the time between charges.

For example, assuming the end effector pieces or jaws of an end effector are fully open initially, moving the trigger from position 1, through position 2 and into neutral position 3, no end effector movement will occur. When position 4 is reached, the end effector pieces begin to close slowly and, in position 5, they will close rapidly to full closure. Assuming initially fully closed end effector pieces and reversed sequential movement of the trigger, reversed movement of the end effector pieces will occur. Thus, for rapid snipping, the trigger is moved rapidly between positions 1 and 5; for slow snipping, the trigger is moved between positions 4 and 2. Beginning with closed end effector pieces or jaws enables tissue spreading.

The operational options and parameters of the instrument of the present invention are increased by incorporating the electrical motors and control devices described above. Controlling the additional motors and the additional functions provided by the motors, such as vibration or oscillation of the end effector tip, is facilitated by using a microprocessor 70. This is particularly true when it is desired to include electronically controlled reciprocating movement of the end effector, vibration of the end effector tip, or another complex movement or motion involving coordinated actuation. Additionally, proportional control in one or more directions or dimensions may be a desired attribute. For example, the harder the user pushes on the control button or trigger, the greater force with which the end effector tip closes and opens. Similarly, the harder the user pushes on a switch, the more rapidly the end effector closes or opens. Because of its flexibility, and dedicated control functionality, a microprocessor is particularly well-suited to achieve control of the servo motors for applications such as these. In any of the embodiments disclosed herein, microprocessor 70 may be used to monitor both voltage and current through the drive motors, as well as monitoring and regulating speeds, motor temperatures, and battery charge states.

The instrument of the present invention is designed for endoscopic, particularly laparoscopic, use. However, there are many other applications for this invention. For example, the interchangeable tips and operating linkages of the present invention may be incorporated into surgical instruments such as needle holders, staplers, lasers, balloon catheters, atherectomy devices, or endoscopes. An electro-cautery feature may be added to any embodiment of the present invention. Placement of catheters such as pacemaker leads, pulmonary monitoring catheters (Swan-Ganz type), angiographic catheters, etc. could be facilitated by using the present invention. Additionally, a chip camera could be added to the end effector tip for site visualization and visual placement, particularly for the placement of stents and stent graft combinations.

While specific embodiments of the present invention have been disclosed and described, it will be understood by those skilled in the art that various changes in form and detail may be made without departing from the spirit and scope of the invention.

What is claimed is:

1. A surgical instrument for use in endoscopy comprising:
   a tubular member having a proximal end and a distal end;
   an end effector pivotally attached directly to the distal end of the tubular member, the end effector comprising a first piece and a second piece;
   linkage extending through the tubular member, the linkage comprising:
      a first elongated member operably connected to the first end effector piece; and
      a second elongated member operably connected to the second end effector piece; and
   a handle attached to the proximal end of the tubular member, the handle comprising:
      a first control means for causing translational movement of the first elongated member relative to the second elongated member, thereby causing the first end effector piece to pivot relative to the second end effector piece; and
      a second control means independent of the first control means, the second control means for causing relative translational movement between the tubular member and both the first and second elongated members without significant relative translational movement between the first and second elongated members, thereby causing the first and second end effector pieces to pivot simultaneously in the same direction.

2. The surgical instrument according to claim 1, wherein the linkage further comprises a tension and compression member, the tension member operably connecting the first elongated member with the first end effector piece, the compression member connecting the second elongated member with the second end effector piece.

3. The surgical instrument according to claim 2, wherein said tension and compression member includes a sheath and a core slidably received in said sheath.

4. The surgical apparatus of claim 3, wherein the sheath is the compression member.

5. The surgical apparatus of claim 3, wherein the sheath comprises a generally tubular body with a lumen.

6. The surgical apparatus of claim 5, wherein the body is formed by a tightly coiled wire.

7. The surgical apparatus of claim 5, wherein the body is formed of a material selected from the group consisting of super-elastic metals and metallic alloys.

8. The surgical apparatus of claim 7, wherein the body is formed of a super-elastic metallic material containing nickel and titanium.

9. The surgical apparatus of claim 7, wherein the core is formed by a length of wire.

10. The surgical apparatus of claim 3, wherein the core is the tension member.

11. The surgical instrument of claim 1, wherein the first and second elongated members each comprise:
   a proximal nut portion disposed within the handle; and
   a distal portion nonrotationally disposed primarily within the tubular member, the elongated member distal portions having screw threads at their proximal ends for releasably and operably coupling the elongated member distal portions to their respective proximal nut portions.

12. The surgical instrument of claim 1, wherein the first and second elongated members are generally concentric with respect to each other.

13. The surgical instrument of claim 1, wherein the first and second elongated members are axially movable in the tubular member.

14. The surgical instrument of claim 1, wherein the handle carries an axially rotatable element operably connected with the tubular member via a bayonet fitting, the axially rotatable element for rotating the tubular member and attached end effector, the rotation being about the axis of the tubular member and relative to the handle.

15. The surgical instrument according to claim 1, wherein:
   the first control means comprises a trigger member;
   the second control means comprises a manually operated slide switch; and
   the handle further comprises a third control means operably connected to the tubular member, the third control means for rotating the tubular member and attached end effector and comprising a rotatable knob, the rotation of the tubular member and end effector being about the axis of the tubular member and relative to the handle.

16. The surgical instrument of claim 1, wherein the first control means comprises a trigger operator.

17. The surgical instrument of claim 1, wherein the second control means comprises a touch-sensitive switch operator.

18. The surgical instrument of claim 1, wherein:
   the handle further comprises a third control means for rotating the tubular member and attached end effector, the rotation being about the axis of the tubular member and relative to the handle; and
   the second and third control means comprise a touch-sensitive switch operator.

19. The surgical instrument of claim 18, wherein the rotation and the simultaneous pivoting of both pieces of the end effector are motor-driven.

20. The surgical instrument of claim 2 or 19, wherein the surgical instrument includes a microprocessor.

21. The surgical instrument of claim 20, wherein the microprocessor is part of an electrical circuit including drive motors connected to and controlled by said microprocessor.

22. The surgical instrument of claim 1, wherein:
   the first control means comprises a trigger operator; and
   the second control means comprises a touch-sensitive switch operator.

23. The surgical instrument of claim 1, wherein each of the two pieces of the end effector is serrated to form a dissector.

24. The surgical instrument of claim 1, wherein the end effector is a grasper.

25. The surgical instrument according to claim 1, wherein each piece of the end effector has an end with an opening for receiving a connector carried adjacent to the distal end of the first and second elongated members.

26. The surgical instrument according to claim 1, wherein the first and second elongated members are of a hexagonal cross-sectional shape so that they are restrained from rotating relative to each other and to the tubular member, and further wherein the first and second elongated members are each releasably connected to the handle by way of bayonet fittings.

27. The surgical instrument according to claim 26, wherein the first and second elongated members each comprise:

a proximal nut portion disposed within the handle; and a distal portion nonrotationally disposed primarily within the tubular member, the elongated member distal portions having screw threads at their proximal ends for releasably and operably coupling the elongated member distal portions to their respective proximal nut portions.

28. The surgical instrument according to claim 27, wherein:

the proximal nut portion of the first elongated member is rotatably mounted in the handle;

the proximal nut portion of the second elongated member is operably coupled to the first proximal nut portion for rotational movement therewith, the second proximal nut portion further being movable axially relative to the first proximal nut portion;

operation of the second control means rotates both elongated member proximal nut portions, thereby translating both elongated member distal portions relative to the tubular member, thereby causing both end effector pieces to pivot simultaneously in the same direction; and operation of the first control means causes axial movement of the second elongated member proximal nut portion relative to the first elongated member proximal nut portion, thereby causing relative translational movement between the elongated member distal portions and one end effector piece to pivot relative to the other.

29. The surgical instrument according to claim 28, wherein the second control means comprises an electric motor for rotating the elongated member proximal nut portions.

30. The surgical instrument according to claim 28, wherein the second control means comprises a manually operated controller for rotating the elongated member proximal nut portions.

31. The surgical instrument according to claim 28, wherein:

each of the elongated members has a rack at its distal end;

each of the end effector pieces has a pinion that engages its respective elongated member rack, wherein translational movement of either elongated member relative to the tubular member causes the respective end effector piece to pivot.

32. The surgical instrument according to claim 31, wherein:

the simultaneous pivoting of the two end effector pieces away from the axis of the tubular member is accomplished by moving the first and second elongated members in the distal direction;

the simultaneous pivoting of the two end effector pieces toward the axis of the tubular member is accomplished by moving the first and second elongated members in the proximal direction; and relative movement between the end effector pieces is accomplished by moving the first and second elongated members relative to one another.

33. The surgical instrument according to claim 1, wherein the handle further comprises a rack and pinion mechanism for translating the elongated members within the tubular member.

34. The surgical instrument according to claim 33, said rack and pinion mechanism comprising:

a pinion attached to the proximal end of each elongated member;

a first rack fixed in the handle and engaging the pinion of one of the elongated members;

a second rack movable relative to the first rack and engaging the pinions of both elongated members; and a third rack movable relative to the first rack and engaging the pinion of the elongated member not engaged by the first rack.

35. The surgical instrument according to claim 34, wherein:

the second control means moves the second rack, thereby translating both elongated members and pivoting both end effector pieces simultaneously in the same direction; and the first control means moves the third rack, thereby translating one elongated member relative to the other resulting in the pivoting of one end effector piece relative to the other.

36. The surgical instrument according to claim 35, wherein:

the first control means comprises a trigger for moving the third rack; and the second control means comprises a slide operator for moving the second rack.

37. A surgical instrument for use in endoscopy comprising:

a tubular member having a proximal end and a distal end;

an end effector pivotally attached directly to the distal end of the tubular member, the end effector comprising a first piece and a second piece, each piece having a pinion at its proximal end;

linkage extending through the tubular member, the linkage comprising:

a first elongated member having, at its distal end, a rack for engaging the pinion of the first end effector piece, wherein relative movement between the first elongated member and the tubular member causes the first end effector piece to pivot; and a second elongated member having a rack at its distal end for engaging the pinion of the second end effector piece, wherein relative movement between the second elongated member and the tubular member causes the second end effector piece to pivot; and a handle attached to the proximal end of the tubular member, the handle comprising:

a first control means for causing translational movement of the first elongated member relative to the second elongated member, thereby causing the first end effector piece to pivot relative to the second end effector piece; and a second control means independent of the first control means, the second control means for causing relative translational movement between the tubular member and both the first and second elongated members without significant relative translational movement between the first and second elongated members, thereby causing the first and second end effector pieces to pivot simultaneously in the same direction.

38. The surgical instrument according to claim 37, wherein the first and second elongated members are of a hexagonal cross-sectional shape so that they are restrained from rotating relative to each other and to the tubular member, and further wherein the first and second elongated members are each releasably connected to the handle by way of bayonet fittings.

39. The surgical instrument according to claim 39, wherein the first and second elongated members each comprise:

a proximal nut portion disposed within the handle; and a distal portion nonrotationally disposed primarily within the tubular member, the elongated member distal portions having screw threads at their proximal ends for releasably and operably coupling the elongated member distal portions to their respective proximal nut portions.

40. The surgical instrument according to claim 39, wherein:

the proximal nut portion of the first elongated member is rotatably mounted in the handle;

the proximal nut portion of the second elongated member is operably coupled to the first proximal nut portion for rotational movement therewith, the second proximal nut portion further being movable axially relative to the first proximal nut portion;

operation of the second control means rotates both elongated member proximal nut portions, thereby translating both elongated member distal portions relative to the tubular member, thereby causing both end effector pieces to pivot simultaneously in the same direction; and operation of the first control means causes axial movement of the second elongated member proximal nut portion relative to the first elongated member proximal nut portion, thereby causing relative translational movement between the elongated member distal portions and one end effector piece to pivot relative to the other.

41. The surgical instrument according to claim 40, wherein the second control means comprises an electric motor for rotating the elongated member proximal nut portions.

42. The surgical instrument according to claim 41, wherein the second control means comprises a manually operated controller for rotating the elongated member proximal nut portions.

43. The surgical instrument according to claim 37, wherein:

the simultaneous pivoting of the two end effector pieces away from the axis of the tubular member is accomplished by moving the first and second elongated members in the distal direction;

the simultaneous pivoting of the two end effector pieces toward the axis of the tubular member is accomplished by moving the first and second elongated members in the proximal direction; and relative movement between the end effector pieces is accomplished by moving the first and second elongated members relative to one another.

44. The surgical instrument according to claim 37, wherein the handle further comprises a rack and pinion mechanism for translating the elongated members within the tubular member.

45. The surgical instrument according to claim 44, wherein said rack and pinion mechanism comprises:

a pinion attached to the proximal end of each elongated member;

a first rack fixed in the handle and engaging the pinion of one of the elongated members;

a second rack movable relative to the first rack and engaging the pinions of both elongated members; and a third rack movable relative to the first rack and engaging the pinion of the elongated member not engaged by the first rack.

46. The surgical instrument according to claim 45, wherein:

the second control means moves the second rack, thereby translating both elongated members and pivoting both end effector pieces simultaneously in the same direction; and the first control means moves the third rack, thereby translating one elongated member relative to the other resulting in the pivoting of one end effector piece relative to the other.

47. The surgical instrument according to claim 46, wherein:

the first control means comprises a trigger for moving the third rack; and the second control means comprises a slide operator for moving the second rack.

48. An endoscopic surgical instrument comprising:

a tubular member having a distal end and a proximal end;

an end effector pivotally attached directly to the distal end of the tubular member, the end effector comprising a first piece and a second piece, each piece having an opening on its proximal end;

linkage extending through the tubular member, the linkage comprising:

a first elongated member having, at its distal end, a pin for engaging the opening in the first end effector piece, wherein relative movement between the first elongated member and the tubular member causes the first end effector piece to pivot; and a second elongated member having, at its distal end, a pin for engaging the opening in the second end effector piece, wherein relative movement between the second elongated member and the tubular member causes the second end effector piece to pivot; and a handle attached to the proximal end of the tubular member, the handle comprising:

a first control means for causing translational movement of the first elongated member relative to the second elongated member, thereby causing the first end effector piece to pivot relative to the second end effector piece; and a first control means for causing relative translational movement between the first and second elongated members, thereby causing the first and second elongated members without significant relative translational movement between the first and second elongated members, thereby causing the first and second end effector pieces to pivot simultaneously in the same direction.

* * * * *